(12) United States Patent
Ni et al.

(10) Patent No.: US 6,605,271 B2
(45) Date of Patent: Aug. 12, 2003

(54) T1 RECEPTOR-LIKE LIGAND II AND USES THEREOF

(75) Inventors: Jian Ni, Rockville, MD (US); Reiner L. Gentz, Rockville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/731,924

(22) Filed: Dec. 8, 2000

(65) Prior Publication Data

US 2002/0142461 A1 Oct. 3, 2002

Related U.S. Application Data

(60) Continuation-in-part of application No. 09/317,641, filed on May 25, 1999, which is a division of application No. 08/916,442, filed on Aug. 22, 1997.
(60) Provisional application No. 60/024,348, filed on Aug. 23, 1996, and provisional application No. 60/169,979, filed on Dec. 10, 1999.

(51) Int. Cl.[7] .............................................. A61K 38/19
(52) U.S. Cl. ........................ 424/85.1; 530/350; 530/351
(58) Field of Search .......................... 424/85.1; 530/350, 530/351; 435/69.7, 4, 335

(56) References Cited

U.S. PATENT DOCUMENTS

| | | | |
|---|---|---|---|
| 5,576,191 A | 11/1996 | Gayle et al. | ............... 435/69.1 |
| 5,767,065 A | 6/1998 | Mosley et al. | ................ 514/2 |

FOREIGN PATENT DOCUMENTS

WO    WO 94/17187    8/1994

OTHER PUBLICATIONS

Thomassen et al. Role of cell type–specific promoter in the developmental regulation of T1, and interleukin 1 receptor homogogue. 1995. Cell Growth and Differentiation, 6(2): 179–84.*

Bergers, G. et al., "Alternative promoter usage of the Fos–responsive gene Fit–1 generates mRNA isoforms coding for either secreted or membrane–bound proteins related to the IL–1 receptor," *EMBO J. 13*:1176–1188, IRL Press Limited (1994).

Bird, T.A. et al., "Evidence that MAP (Mitogen–Activated Protein) Kinase Activation may be a Necessary but Not Sufficient Signal for a Restricted Subset of Responses in IL–1–Treated Epidermoid Cells," *Cytokine 4*:429–440, Academic Press (1992).

Cleary, M.L. et al., "Cloning and Structural Analysis of cDNAs for bcl–2 and a Hybrid bcl–2/Immunoglobulin Transcript Resulting from the t(14;18) Translocation," *Cell 47*:19–28, Cell Press (1986).

Eldon, E. et al., "The Drosophila 18 wheeler is required for morphogenesis and has striking similarities to Toll," *Development 120*:885–899, Company Of Biologists Limited (1994).

Fleischmann, R.D. et al., "Whole–Genome Random Sequencing and Assembly of *Haemophilus influenzae* Rd,"*Science 269*:496–512, Association for the Advancement of Science (Jul. 1995).

Gay, N.J. and F.J. Keith, "Drosophila Toll and IL–1 receptor," *Nature 351*:355–356, Macmillan Publishers Ltd. (1991).

Gayle, M.A. et al., "Cloning of a Putative Ligand for the T1/ST2 Receptor," *J. Biol. Chem. 271*:5784–5789, American Society for Biochemistry and Molecular Biology, Inc. (Mar. 1996).

Greenfeder, S.A. et al., "Molecular Cloning and Characterization of a Second Subunit of the Interleukin 1 Receptor Complex," *J. Biol. Chem. 270*:13757–13765, American Society for Biochemistry and Molecular Biology, Inc. (Jun. 1995).

Hashimoto, C. et al., "The Toll Gene of Drosophila, Required for Dorsal–Ventral Embryonic Polarity, Appears to Encode a Transmembrane Protein," *Cell 52*:269–279, Cell Press (1988).

Hopp, T.P., "Evidence from sequence information that the interleukin–1 receptor is a transmembrane GTPase," *Protein Science 4*:1851–1859, Cold Spring Harbor Laboratory Press (Sep. 1995).

Klemenz, R. et al., "Serum– and oncoprotein–mediated induction of a gene with sequences similarity to the gene encoding carcinoembryonic antigen," *Proc. Natl. Acad. Sci. USA 86*:5708–5712, National Academy of Sciences of the USA (1989).

Kumar, S. et al., "ST2/T1 Protein Functionally Binds to Two Secreted Proteins from Balb/c 3T3 and Human Umbilical Vein Endothelial Cells but Does Not Bind Interleukin 1," *J. Biol. Chem. 270*:27905–27013, American Society for Biochemistry and Molecular Biology, Inc. (Nov. 1995).

Lord, K.A. et al., "Nucleotide sequence and expression of a cDNA encoding MyD88, a novel myeloid differentiation primary response gene induced by IL6," *Oncogene 5*:1095–1097, McMillan Press (1990).

(List continued on next page.)

Primary Examiner—Lorraine Spector
Assistant Examiner—Dong Jiang
(74) Attorney, Agent, or Firm—Human Genome Sciences, Inc.

(57) ABSTRACT

The present invention relates to a novel T1 Receptor (T1R)-like ligand II protein. In particular, isolated nucleic acid molecules are provided encoding the T1R-like ligand II protein. T1R-like ligand II polypeptides are also provided, as are recombinant vectors and host cells for expressing the same. This invention further relates to pharmaceutical compositions and formulations comprising T1R-like ligand II. Also provided are methods of using T1R-like ligand II polynucleotides, polypeptides, antibodies or agonists/antagonists for therapeutic and diagnostic purposes. Diagnostic kits are further provided.

58 Claims, 5 Drawing Sheets

OTHER PUBLICATIONS

Mitcham, J.L. et al., "T1/ST2 Signaling Establishes It as a Member of an Expanding Interleukin–1 Receptor Family," *J. Biol. Chem.* 271:5777–5783, American Society for Biochemistry and Molecular Biology, Inc. (Mar. 1996).

Nomura, N. et al., "Prediction of the Coding Sequences of Unidentified Human Genes. I. The Coding Sequences of 40 New Genes (KIAA0001–KIAA0040) Deduced by Analysis of Randomly Sampled cDNA Clones from Human Immature Myeloid Cell Line KG–1", *DNA Res.* 1:27–35, Kazusa DNA Research Institute And Universal Academy Press (1994).

Ostrowski, J. et al., "A Serine/Threonine Kinase Activity Is Closely Associated with a 65–kDa Phosphoprotein Specifically Recognized by the κB Enhancer Element," *J. Biol. Chem.* 266:12722–12733, American Society for Biochemistry and Molecular Biology, Inc. (1991).

Parnet, P. et al., "IL–1Rrp Is a Novel Receptor–like Molecule Similar to the Type I Interleukin–1 Receptor and Its Homologues T1/ST2 and IL–1R AcP," *J. Biol. Chem.* 271:3967–3970, American Society for Biochemistry and Molecular Biology, Inc. (Feb. 1996).

Reikerstorfer, A. et al., "Low Affinity Binding of Interleukin–1β and Intracellular Signaling via NF–κB Identify Fit–1 as a Distant Member of the Interleukin–1 Receptor Family," *J. Biol. Chem.* 270:17645–17648, American Society for Biochemistry and Molecular Biology, Inc. (Jul. 1995).

Schneider, D.S. et al., "Dominant and recessive mutations define functional domains of Toll, a transmembrane protein required for dorsal–ventral polarity in the Drosophila embryo," *Genes & Dev.* 5:797–807, Cold Spring Harbor Laboratory Press (1991).

Sims, J.E. et al., "cDNA Expression Cloning of the IL–1 Receptor, a Member of the Immunoglobulin Superfamily," *Science* 241:585–589, Association for the Advancement of Science (1988).

Sims, J.E. et al., "Genomic Organization of the Type I and Type II IL–1 Receptors," *Cytokine* 7:483–490, Academic Press (Aug. 1995).

Stamnes, M.A. et al., "An Integral Membrane Component of Coatomer–coated Transport Vesicles Defines a Family of Proteins Involved in Budding," *Proc. Natl. Acad. Sci. USA* 92:8011–8015, National Academy of Sciences of the USA (Aug. 1995).

Tominaga, S., "A putative protein of a growth specific cDNA from BALB/c–3T3 cells is highly similar to the extracellular portion of mouse interleukin 1 receptor," *FEBS Lett.* 258:301–304, Elsevier Science Publishers B.V. (1989).

Yanigisawa, K. et al., "Presence of a novel primary response gene ST2L, encoding a product highly similar to the interleukin 1 receptor type 1," *FEBS Lett.* 318:83–87, Elsevier Science Publishers B.V. (1993).

International Search Report for Applications No. PCT/US96/13768, mailed Jan., 1997.

Database EST–STS on MASPAR search, WashU–Merck EST Project (St Louis MO, USA) No. H50051, from Hillier et al., "yo26g04.r1 *Homo sapiens* cDNA clone 179094 5'," (Sep. 1995).

Database EST–STS on MASPAR search, WashU–Merck EST Project (St Louis MO, USA) No. T48838, from Hillier et al., "yb05e06.r1 *Homo sapiens* cDNA clone 70306 5'," (Feb. 1995).

Database EST–STS on MASPAR search, Research Institute, Otsuka Pharmaceutical Co. Ltd. (Kagasuno Kawauchi–cho Tokushima, Japan) No. D81710, from Fujiwara et al., "Human fetal brain cDNA 5'–end GEN–401D07" (Nov. 1995).

Genbank Report, Accession No. AA013099, submitted by Hillier et al. (Nov. 1996).

Genbank Report, Accession No. AA251084, submitted by National Cancer Institute, Cancer Genome Anatomy Project (CGAP) (Aug. 1997).

Genbank Report, Accession No. R58562, submitted by Hwang et al. (May 1996).

Genbank Report, Accession No. N28878, submitted by Hillier et al. (Jan. 1996).

Genbank Report, Accession No. AA019348, submitted by Hillier et al. (Aug. 1996).

Genbank Report, Accession No. N49615, submitted by Hillier et al. (Feb. 1996).

Genbank Report, Accession No. AA112675, submitted by Hillier et al. (Aug. 1997).

Genbank Report, Accession No. AA082161, submitted by Hillier et al. (Jul. 1997).

Genbank Report, Accession No. H03613, submitted by Hillier et al. (Jun. 1995).

Genbank Report, Accession No. R54717, submitted by Hillier et al. (May 1995).

Genbank Report, Accession No. H27167, submitted by Hillier et al. (Jul. 1995).

Genbank Report, Accession No. AA188741, submitted by Hillier et al. (Jan. 1997).

NCBI Entrez, GenBank Report, Accession No. R54718, from Hillier, L. et al. (May 1995).

NCBI Entrez, GenBank Report, Accession No. H03503, from Hillier, L. et al. (Jun. 1995).

NCBI Entrez, GenBank Report, Accession No. H27168, from Hillier, L. et al. (Jul. 1995).

NCBI Entrez, GenBank Report, Accession No. N21637, from Hillier, L. et al. (Dec. 1995).

NCBI Entrez, GenBank Report, Accession No. N34911, from Hillier, L. et al. (Jan. 1996).

NCBI Entrez, GenBank Report, Accession No. N45687, from Hillier, L. et al. (Feb. 1996).

NCBI Entrez, GenBank Report, Accession No. N46921, from Hillier, L. et al. (Feb. 1996).

NCBI Entrez, GenBank Report, Accession No. W58982, from Marra, M. et al. (Jun. 1996).

NCBI Entrez, GenBank Report, Accession No. AA003600, from Marra, M. et al. (Jul. 1996).

NCBI Entrez, GenBank Report, Accession No. C16937, from Fujiwara, T. et al. (Sep. 1996).

NCBI Entrez, GenBank Report, Accession No. AA089688, from Liew, C.C. (Oct. 1996).

Genbank Report, Accession No. AA094735, submitted by Liew, C.C. (Oct. 1996).

NCBI Entrez, GenBank Report, Accession No. AA097327, from Marra, M. et al. (Feb. 1997).

NCBI Entrez, GenBank Report, Accession No. AA097350, from Marra, M. et al. (Feb. 1997).

NCBI Entrez, GenBank Report, Accession No. AA186155, from Marra, M. et al. (Feb. 1997).

NCBI Entrez, GenBank Report, Accession No. AA288199, from Marra, M. et al. (Apr. 1997).

NCBI Entrez, GenBank Report, Accession No. AA381943, from Adams, M.D. et al. (Apr. 1997).

Genbank Report, Accession No. AA285143, submitted by National Cancer Institute, Cancer Genome Anatomy Project (CGAP) (Aug. 1997).

NCBI Entrez, GenBank Report, Accession No. AA413599, from Marra, M. et al. (Aug. 1997).

NCBI Entrez, GenBank Report, Accession No. AA393405, from Hillier, L. et al. (Aug. 1997).

NCBI Entrez, GenBank Report, Accession No. AA397587, from Hillier, L. et al. (Aug. 1997).

NCBI Entrez, GenBank Report, Accession No. AA400773, from Hillier, L. et al. (Aug. 1997).

NCBI Entrez, GenBank Report, Accession No. AA251721, from NCI–CGAP (Aug. 1997).

NCBI Entrez, GenBank Report, Accession No. AA287714, from NCI–CGAP (Aug. 1997).

NCBI Entrez, GenBank Report, Accession No. AA287713, from NCI–CGAP (Aug. 1997).

NCBI Entrez, GenBank Report, Accession No. AA421135, from Hillier, L. et al. (Nov. 1997).

NCBI Entrez, GenBank Report, Accession No. AA668793, from NCI–CGAP (Nov. 1997).

NCBI Entrez, GenBank Report, Accession No. AA694551, from NCI–CGAP (1998).

NCBI Entrez, GenBank Report, Accession No. AA743312, from NCI–CGAP (1998).

Pir56 database, Accession No. S54622, de Haan et al. (Jul. 1995).

* cited by examiner

```
                10                      30                      50
                 .                       .                       .
CACGAGGACAACAGTACCTGACGCCTCTTTCAGCCCGGGATCGCCCCAGCAGGGATGGGC
                                                            M  G 70                      90                     110
                 .                       .                       .
GACAAGATCTGGCTGCCCTTCCCCGTGCTCCTTCTGGCCGCTCTGCCTCCGGTGCTGCTG
 D  K  I  W  L  P  F  P  V  L  L  L  A  A  L  P  P  V  L  L 130                     150                     170
                 .                       .                       .
CCTGGGGCGGCCGGCTTCACACCTTCCCTCGATAGCGACTTCACCTTTACCCTTCCCGCC
 P  G  A  A  G  F  T  P  S  L  D  S  D  F  T  F  T  L  P  A 190                     210                     230
                 .                       .                       .
GGCCAGAAGGAGTGCTTCTACCAGCCCATGCCCCTGAAGGCCTCGCTGGAGATCGAGTAC
 G  Q  K  E  C  F  Y  Q  P  M  P  L  K  A  S  L  E  I  E  Y 250                     270                     290
                 .                       .                       .
CAAGTTTTAGATGGAGCAGGATTAGATATTGATTTCCATCTTGCCTCTCCAGAAGGCAAA
 Q  V  L  D  G  A  G  L  D  I  D  F  H  L  A  S  P  E  G  K 310                     330                     350
                 .                       .                       .
ACCTTAGTTTTTGAACAAAGAAAATCAGATGGAGTTCACACTGTAGAGACTGAAGTTGGT
 T  L  V  F  E  Q  R  K  S  D  G  V  H  T  V  E  T  E  V  G 370                     390                     410
                 .                       .                       .
GATTACATGTTCTGCTTTGACAATACATTCAGCACCATTTCTGAGAAGGTGATTTTCTTT
 D  Y  M  F  C  F  D  N  T  F  S  T  I  S  E  K  V  I  F  F 430                     450                     470
                 .                       .                       .
GAATTAATCCTGGATAATATGGGAGAACAGGCACAAGAACAAGAAGATTGGAAGAAATAT
 E  L  I  L  D  N  M  G  E  Q  A  Q  E  Q  E  D  W  K  K  Y 490                     510                     530
                 .                       .                       .
ATTACTGGCACAGATATATTGGATATGAAACTGGAAGACATCCTGGAATCCATCAACAGC
 I  T  G  T  D  I  L  D  M  K  L  E  D  I  L  E  S  I  N  S 550                     570                     590
                 .                       .                       .
ATCAAGTCCAGACTAAGCAAAAGTGGGCACATACAAACTCTGCTTAGAGCATTTGAAGCT
 I  K  S  R  L  S  K  S  G  H  I  Q  T  L  L  R  A  F  E  A
```

FIG.1A

```
           610                  630                   650
            .                    .                     .
CGTGATCGAAACATACAAGAAAGCAACTTTGATAGAGTCAATTTCTGGTCTATGGTTAAT
 R   D   R   N   I   Q   E   S   N   F   D   R   V   N   F   W   S   M   V   N 670                  690                   710
            .                    .                     .
TTAGTGGTCATGGTGGTGGTGTCAGCCATTCAAGTTTATATGCTGAAGAGTCTGTTTGAA
 L   V   V   M   V   V   V   S   A   I   Q   V   Y   M   L   K   S   L   F   E 730                  750                   770
            .                    .                     .
GATAAGAGGAAAAGTAGAACTTAAAACTCCAAACTAGAGTACGTAACATTGAAAAATGAG
 D   K   R   K   S   R   T   *

790                  810                   830
            .                    .                     .
GCATAAAAATGCCATAAACTGTTACAGTCCAGACCATTAATGGTCTTCTCCAAAATATTT 850                  870                   890
            .                    .                     .
TGAGATATAAAAGTAGGAAACAGGTATAATTTTAATGTGAAAATTAAGTCTTCACTTTCT 910                  930                   950
            .                    .                     .
GTGCAAGTAATCCTGCTGATCCAGTTGTACTTAAGTGTGTAACAGGAATATTTTGCAGAA 970                  990                  1010
            .                    .                     .
TATAGGTTTAACTGAATGAAGCCATATTAATAACTGCATTTTCCTAACTTTGAAAAATTT 1030                 1050                  1070
            .                    .                     .
TGCAAATGTCTTAGGTGATTTAAATAAATGAGTATTGGGCCTAATTGCAACACCAGTCTG 1090                 1110                  1130
            .                    .                     .
TTTTTAACAGGTTCTATTACCCAGAACTTTTTTGTAAATGCGGCAGTTACAAATTAACTG 1150                 1170                  1190
            .                    .                     .
TGGAAGTTTTCAGTTTTAAGTTATAAATCACCTGAGAATTACCTAATGATGGATTGAATA 1210                 1230
            .                    .
AATCTTTAGACTACAAAAAAAAAAAAAAAAAAAAAAAAAAAAA
```

FIG.1B

```
  1   .MGDKIWLPFPVLLLAALPPVLLPGAAGFTPSLDSDFTFTLPAGQKECFY   49
       |:.    |:::::||  :||| : |:||  .|   |::|||  ||||.|:|||
  1   MMAAGAALALALWLL..MPPVEV.GGAGPPPIQDGEFTFLLPAGRKQCFY   47

50   QPMPLKASLEIEYQVLDGAGLDIDFHLASPEGKTLVFEQRKSDGVHTVE.   98
       |. |  .||||.||||::||||||:||  .||:|   || |  ||.|||||||
 48   QSAPANASLETEYQVIGGAGLDVDFTLESPQGVLLVSESRKADGVHTVEP   97

99   TEVGDYMFCFDNTFSTISEKVIFFELILDNMGEQAQEQEDWKKYITGTDI   148
       ||.|||.:||||.|||||||::|||||:|.:.:: :| |:|  . :.....::
 98   TEAGDYKLCFDNSFSTISEKLVFFELIFDSLQDD.EEVEGWAEAVEPEEM   146

149   LDMKLEDILESINSIKSRLSKSGHIQTLLRAFEARDRNIQESNFDRVNFW   198
       ||:|:|||  |||:.::.||.:|::::|||||||||||||:||:|::|||||
147   LDVKMEDIKESIETMRTRLERSIQMLTLLRAFEARDRNLQEGNLERVNFW   196

199   SMVNLVVMVVVSAIQVYMLKSLFEDKRKSRT.   229
       | ||:.|:::|..:||: ||.:|:|||- .||
197   SAVNVAVLLLVAVLQVCTLKRFFQDKRPVPT.   227
```

FIG.2

T1 RECEPTOR-LIKE LIGAND II AND USES THEREOF

CROSS-REFERENCE TO RELATED APPLICATIONS

The present application is a Continuation-in-Part of U.S. application Ser. No. 09/317,641, filed May 25, 1999, which is a Divisional of U.S. application Ser. No. 08/916,442, filed Aug. 22, 1997, which claims priority benefit of U.S. application Ser. No. 60/024,348, filed Aug. 23, 1996. The present application also claims priority benefit of U.S. Application No. 60/169,979, filed Dec. 10, 1999. All of said applications are herein incorporated by reference.

BACKGROUND OF THE INVENTION

1. Field of the Invention

The present invention relates to a novel T1Receptor (T1R)-like ligand II protein. In particular, isolated nucleic acid molecules are provided encoding the T1R-like ligand II protein. T1R-like ligand II polypeptides are also provided, as are recombinant vectors and host cells for expressing the same. This invention further relates to pharmaceutical compositions and formulations comprising T1R-like ligand II. Also provided are methods of using T1R-like ligand II polynucleotides, polypeptides, antibodies or agonists/antagonists for therapeutic and diagnostic purposes. Diagnostic kits are further provided.

2. Related Art

Interleukin-1 (IL-1).

Interleukin-1 (IL-1α and IL-1β) is a "multifunctional" cytokine that affects nearly every cell type, and often in concert with other cytokines or small mediator molecules. (Dinarello, C. A., *Blood* 87:2095-2147 (Mar. 15, 1996).) There are three members of the IL-1 gene family: IL-1α, IL-1β, and IL-1 receptor antagonist (IL-1Ra). IL-1α and IL-1β are agonists and IL-1Ra is a specific receptor antagonist. IL-1α and β are synthesized as precursors without leader sequences. The molecular weight of each precursor is 31 kD. Processing of IL-1α or IL-1β to "mature" forms of 17 kD requires specific cellular proteases. In contrast, IL-1Ra evolved with a signal peptide and is readily transported out of the cells and termed secreted IL-1Ra (sIL-1Ra).

IL-1 Receptor and Ligands.

The receptors and ligands of the IL-1 pathway have been well defined (for review, see Dinarello, C. A., *FASEB J.* 8:1314-1325 (1994); Sims, J. E. et al., *Interleukin*-1 *signal transduction: Advances in Cell and Molecular Biology of Membranes and Organelles*, Vol.3, JAI Press, Inc., Greenwich, Conn. (1994), pp. 197-222). Three ligands, IL-1α, IL-1β, and IL-1 receptor antagonist (IL-1Ra) bind three forms of IL-1 receptor, an 80-kDa type I IL-1 receptor (IL-IR1) (Sims, J. E. et al., *Science* 241:585-589 (1988)), a 68-kDa type II IL-1 receptor (IL-1RII) (McMahan, C. J. et al., *EMBO J.* 10:2821-2832 (1991)), and a soluble form of the type II IL-1R (sIL-1RII) (Colotta, F. et al., *Science* 261:472-475 (1993)).

The interactions between the IL-1 ligands and receptors play an essential role in the stimulation and regulation of the IL-1 -mediated host response to injury and infection. Cells expressing IL-1RI and treated with IL-1α or IL-1β respond in several specific ways, including stimulating nuclear localization of the rel-related transcription factor, NF-κβ (for review, see Thanos, D. & Maniatis, T., *Cell* 80:529-532 (1996)), activation of protein kinases of the mitogen-activated protein kinase superfamily that phosphorylate residue threonine 669 (Thr-669) of the epidermal growth factor receptor (EGFR) (Guy, G. R. et al., *J. Biol. Chem.* 267:1846-1852(1992); Bird, T. A. et al., *J. Biol. Chem.* 268:22861-22870(1991); Bird, T. A. et al., *J. Biol. chem.* 269:31836-31844 (1994)), and stimulation of transcription of the IL-8 gene (Mukaida, N. et al., *J. Biol. chem.* 265:21128-21133 (1990)).

IL-1RI-like Family.

Many proteins from diverse systems show homology to the cytoplasmic domain of the IL-1RI. This expanding IL-1RI-like family includes mammalian proteins, Drosophila proteins, and a plant (tobacco) protein. (Gay, N. J. & Keith, F. J., *Nature* 351:355-356 (1991); Hashimoto, C. et al., *Cell* 52:269-279 (1988); Schneider, D. S. et al., *Genes & Dev.* 5:797-807 (1991); Edon, E. et al., *Development* 120:885-899 (1994); Mitchan, J. L. et al., *J. Biol. Chem* 271:5777-5782 (Mar. 8, 1996)).

The mammalian IL-1RI-like receptor family members include a murine protein MyD88 (Lord, K. A. et al., *Oncogene* 5:1095-1097 (1990)) and a human gene, rsc786 (Nomura, N. et al., *DNA Res.* 1:27-35 (1994)). Another murine receptor member, T1/ST2, was previously characterized as a novel primary response gene expressed in BALB/c-3T3 cells (Klemenz, R. et al., *Proc. Natl. Acad. Sci. USA* 86:5708-5712 (1989); Tominaga, S., *FEBS Lett.* 258:301-304 (1989); Tominga, S. et al., *FEBS Lett.* 318:83-87 (1993)). The transmembrane protein muIL-1R AcP (Greenfeder, S. A. et al., *J. Biol. Chem.* 270:13757-13765 (1995)) has homology to both the type I and type II IL-1R. IL-1R AcP has recently been shown to increase the affinity of IL-1RI for IL-1β and may be involved in mediating the IL-1 response.

T1 Receptors.

T1/ST2 receptors (hereinafter, "T1 receptors"), as a member of the IL-1 receptor family (Bergers, G., et al., *EMBO J.* 13:1176 (1994)), have various homologs in different species. In the rat, it is called Fit-1, an estrogen-inducible, c-fos-dependent transmembrane protein that shares 26% to 29% amino acid homology to the mouse IL-1RI and II, respectively. In the mouse, the Fit-1 protein is called ST2 and in the human it is called T1. The organization of the two IL-1 receptors and the Fit-1/ST2/T1 genes indicates they are derived from a common ancestor (Sims, J. E., et al., *Cytokine* 7:483 (1995)). Fit-1 exists in two forms: a membrane form (Fit-1M) with a cytosolic domain similarly to that of the IL-1RI and Fit-1S, which is secreted and composed of the extracellular domain of Fit-M.

In many ways, these two forms of the Fit-1 protein are similar to those of the membrane-bound and soluble IL-1RI. It has been shown that the IL-1sRI is derived from proteolytic cleavage of the cell-bound form (Sims, J. E., et al., *Cytokine* 7:483 (1995)). On the other hand, the Fit-1 gene is under the control of two promoters, which results in two isoforms coding for either the membrane or soluble form of the receptor. Two RNA transcripts result from alternative RNA splicing of the 3' end of the gene. Although IL-1β binds weakly to Fit-1 and does not transduce a signal (Reikerstorger, A., et al., *J. Biol. Chem.* 270:17645 (1995)), a chimeric receptor consisting of the extracellular murine IL-1RI fused to the cytosolic Fit-1 transduces an IL-1 signal (Reikerstorger, A., et al., *J. Biol. Chem.* 270:17645 (1995)). The cytosolic portion of Fit-1 align with GTPase-like sequences of IL-1RI (Hopp, T. P., *Protein Sci.* 4:1851 (1995)) (see below).

IL-1 Production in Various Disease States.

Increased IL-1 production has been reported in patients with various viral, bacterial, fungal, and parasitic infections; intravascular coagulation; high-dose IL-2 therapy; solid tumors; leukemias; Alzheimer's disease; HIV-1 infection; autoimmune disorders; trauma (surgery); hemodialysis; ischemic diseases (myocardial infarction); noninfectious hepatitis; asthma; UV radiation; closed head injury; pancreatitis; periodontitis; graft-versus-host disease; transplant rejection; and in healthy subjects after strenuous exercise. There is an association of increased IL-1β production in patients with Alzheimer's disease and a possible role for IL-1 in the release of the amyloid precursor protein (Vasilakos, J. P., et al., *FEBS Lett.* 354:289 (1994)). However, in most conditions, IL-1 is not the only cytokine exhibiting increased production and hence the specificity of the IL-1 findings as related to the pathogenesis of any particular disease is lacking. In various disease states, IL-1, but not IL-1α, is detected in the circulation.

IL-1 in Therapy.

Although IL-1 has been found to exhibit many important biological activities, it is also found to be toxic at doses that are close to therapeutic dosages (Dinarello, C. A., *Blood* 87:2095-2147 (Mar. 15,1996)). In general, the acute toxicities of either isoform of IL-1 were greater after intravenous compared with subcutaneous injection. Subcutaneous injection was associated with significant local pain, erythema, and swelling (Kitamura, T., & Takaku, F., *Exp. Med.* 7:170 (1989); Laughlin, M. J., *Ann. Hematol.* 67:267 (1993)). Patients receiving intravenous IL-1 at doses of 100 ng/kg or greater experienced significant hypotension. In patients receiving IL-1β from 4 to 32 ng/kg subcutaneously, there was only one episode of hypotension at the highest dose level (Laughlin, M. J., *Ann. Hematol.* 67:267 (1993)).

Contrary to IL-1-associated myelostimulation in patients with normal marrow reserves, patients with a plastic anemia treated with 5 daily doses of IL-1α (30 to 100 ng/kg) had no increases in peripheral blood counts or bone marrow cellularity (Walsh, C. E., et al., *Br. J. Haematol* 80:106 (1992)). IL-1 has been administered to patients undergoing various regiments of chemotherapy to reduce the nadir of neutropenia and thrombocytopenia.

Daily treatment with 40 ng/kg IL-1α from day 0 to day 13 of autologous bone marrow or stem cells resulted in an earlier recovery of neutropenia (median, 12 days; P<0.001) (Weisdorf, D., et al., *Blood* 84:2044 (1994)). After 14 days of treatment, the bone marrow was significantly enriched with committed myeloid progenitor cells. Similar results were reported in patients with AML receiving 50 ng/kg/d of IL-1β for 5 days starting at the time of transplantation with purged or nonpurged bone marrow (Nemunaitis, J., et al., *Blood* 83:3473 (1994)). Injecting humans with low doses of either IL-1α or IL-1β confirms the impressive pyrogenic and hypotension-inducing properties of the molecules.

Amelioration of Disease using Soluble IL-1Receptors.

Administration of murine IL-1sRI to mice has increased the survival of heterotopic heart allografts and reduced the hyperplastic lymph node response to allogeneic cells (Fanslow, W. C., et al., *Science* 248:739 (1990)). In a rat model of antigen-induced arthritis, local instillation of the murine IL-1sRI reduced joint swelling and tissue destruction (Dower, S. K., et al., *Therapeutic Immunol.* 1:113 (1994)). These data suggest that the amount of IL-1sRI administered in the normal, contralateral joint was acting systemically. In a model of experimental autoimmune encephalitits, the IL-1sRI reduced the severity of this disease (Jacobs, C. A., et al., *J. Immunol.* 146:2983 (1991)).

SUMMARY OF THE INVENTION

The present invention provides isolated nucleic acid molecules comprising a polynucleotide encoding a human T1 receptor-(T1R-)like ligand II polypeptide having the amino acid sequence in FIGS. 1A–1B (SEQ ID NO:2). The T1R-like ligand II contains an open reading frame encoding a polypeptide of about 229 amino acid residues including an N-terminal methionine, a leader sequence of about 26 amino acid residues, an extracellular mature domain of about 168 residues, a transmembrane domain of about 23 residues and an intracellular domain of about 12 amino acid residues, and a deduced molecular weight of about 26 kDa. The 203 amino acid sequence of the expected mature T1R-like ligand II protein is shown in SEQ ID NO:2 (amino acid residues 1-203).

The invention also provides isolated nucleic acid molecules encoding an T1R-like ligand II having an amino acid sequence encoded by the cDNA of the clone deposited as ATCC Deposit No. 97655 on Jul. 12, 1996. Preferably, the nucleic acid molecule will encode the mature polypeptide encoded by the above-described deposited cDNA.

Thus, one aspect of the invention provides an isolated nucleic acid molecule comprising a polynucleotide having a nucleotide sequence selected from the group consisting of: (a) a nucleotide sequence encoding the T1R-like ligand II polypeptide having the complete amino acid sequence in SEQ ID NO:2; (b) a nucleotide sequence encoding the T1R-like ligand II polypeptide having the complete amino acid sequence in SEQ ID NO:2 but minus the N-terminal methionine residue; (c) a nucleotide sequence encoding the mature T1R-like ligand II polypeptide having the amino acid sequence at positions from about I to about 203 in SEQ ID NO:2; (d) a nucleotide sequence encoding the T1R-like ligand II polypeptide having the complete amino acid sequence encoded by the cDNA clone contained in ATCC Deposit No. 97655; (e) a nucleotide sequence encoding the mature T1R-like ligand II polypeptide having the amino acid sequence encoded by the cDNA clone contained in ATCC Deposit No. 97655; and (f) a nucleotide sequence complementary to any of the nucleotide sequences in (a), (b), (c), (d), or (e) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), or (f), above, or a polynucleotide which hybridizes under stringent hybridization conditions to a polynucleotide in (a), (b), (c), (d), (e), or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a T1R-like ligand II polypeptide having an amino acid sequence in (a), (b), (c), (d), or (e), above.

The present invention also relates to recombinant vectors which include the isolated nucleic acid molecules of the present invention, host cells containing the recombinant vectors, and the production of T1R-like ligand II polypeptides or fragments thereof by recombinant techniques.

The invention further provides an isolated T1R-like ligand II polypeptide having an amino acid sequence selected from the group consisting of: (a) the amino acid sequence of the T1R-like ligand II polypeptide having the complete 229 amino acid sequence, including the leader sequence shown in SEQ ID NO:2; (b) the amino acid sequence of the T1R-like ligand II polypeptide having the complete 229 amino acid sequence, including the leader sequence shown in SEQ ID NO:2 but minus the N-terminal methionine residue; (c) the amino acid sequence of the mature T1R-like ligand II polypeptide (without the leader) having the amino acid sequence at positions 1 to 203 in SEQ ID NO:2; (d) the amino acid sequence of the T1R-like ligand II polypeptide having the complete amino acid sequence, including the leader, encoded by the cDNA clone contained in ATCC Deposit No. 97655; and (e) the amino acid sequence of the mature T1R-like ligand II polypeptide having the amino acid sequence encoded by the cDNA clone contained in ATCC Deposit No. 97655. The polypeptides of the present invention also include polypeptides having an amino acid sequence at least 90% identical, and more preferably 95%, 96%, 97%, 98% or 99% identical to those above.

An additional embodiment of this aspect of the invention relates to a peptide or polypeptide which has the amino acid sequence of an epitope-bearing portion of a T1R-like ligand II polypeptide having an amino acid sequence described in (a), (b), (c), (d), or (e), above. Peptides or polypeptides having the amino acid sequence of an epitope-bearing portion of a T1R-like ligand II polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a T1R-like ligand II polypeptide having an amino acid sequence described in (a), (b), (c), (d), or (e) above.

The invention also relates to fragments of the above-described polypeptides. Preferred polypeptide fragments according to the present invention include a polypeptide comprising: the mature polypeptide (amino acid residues from about 1 to about 203 in SEQ ID NO:2), the extracellular domain (amino acid residues from about 1 to about 168 in SEQ ID NO:2), the transmembrane domain (amino acid residues from about 169 to about 191 in SEQ ID NO:2), the intracellular domain (amino acid residues from about 192 to about 203 in SEQ ID NO:2), or the extracellular and intracellular domain with all or part of the transmembrane domain deleted.

In addition, the invention provides for fusion polypeptides of T1R-like ligand II which may be generated through the techniques of gene-shuffling, motif-shuffling, exon-shuffling and/or codon-shuffling.

The invention further provides for proteins containing polypeptide sequences encoded by the polynucleotides of the invention. The proteins may be in the form of monomers or multimers. The preparation of these proteins and compositions (preferably pharmaceutical compositions) containing these proteins are also provided.

In another embodiment, the invention provides transgenic animals which express the polypeptides and proteins of the invention.

In yet another embodiment, chromosome assays are provided which allow for chromosome identification. Nucleic acids of the invention can be used to specifically target and hybridize to a particular location on an individual human chromosome. Once a sequence has been mapped to a precise chromosome location, the physical position of the sequence on the chromosome can be correlated with genetic map data.

In another embodiment, the invention provides for antisense and ribozyme antagonists of T1R-like ligand II.

It is believed that biological activities of the T1R-like ligand II of the present invention may be similar to the biological activities of the T1R ligand and IL-1. Significantly, higher or lower levels of T1R-like ligand II may be detected in tissues or bodily fluids (e.g., serum, plasma, urine, synovial fluid or spinal fluid) taken from an individual having a T1R ligand- or IL-1-related disorder, relative to a "normal" T1R-like ligand II gene expression level, i.e., the expression level in tissue or bodily fluids from an individual not having the T1R ligand- or IL-1-related disorder. Thus, detecting expression of T1R-like ligand II gene expression according to the present invention is a diagnostic marker. Accordingly, the invention provides for diagnostic kits used to detect levels of T1R-like ligand II expression.

The invention also provides methods for producing and isolating antibodies that bind specifically to an T1R-like ligand II polypeptide having an amino acid sequence as described herein. Such antibodies are useful diagnostically or therapeutically as described herein.

The invention is further related to a method for treating an individual in need of an increased or decreased level of T1R-like ligand II activity in the body, comprising administering to such an individual a composition comprising a T1R-like ligand II polypeptide or an inhibitor thereof.

As such, pharmaceutical compositions of T1R-like ligand II are provided. Formulations of T1R-like ligand II are also provided as are methods for administering therapeutic doses of T1R-like ligand II polynucleotides, polypeptides, antibodies, agonists, antagonists and/or fragments and variants thereof.

Finally, the invention provides for methods of using the polynucleotides encoding T1R-like ligand II polypeptides, antibodies, agonists, antagonists, and/or fragments and variants thereof, in gene therapy.

BRIEF DESCRIPTION OF THE FIGURES

FIGS. 1A–1B shows the nucleotide (SEQ ID NO:1) and deduced amino acid (SEQ ID NO:2) sequences of the T1R-like ligand II protein determined by sequencing the cDNA clone contained in ATCC Deposit No. 97655. The protein has a leader sequence of about 26 amino acid residues (first underlined sequence), an extracellular mature domain of about 168 amino acid residues (sequence between the first and second underlined sequences), a transmembrane domain of about 23 amino acid residues (second underlined sequence), and an intracellular domain of about 12 amino acid residues (the remaining sequence).

FIG. 2 shows the regions of similarity between the amino acid sequences of the T1R-like ligand II and the protein sequence of GenBank accession No. U41804 (SEQ ID NO:3), showing an overall 56% identity.

DETAILED DESCRIPTION OF THE INVENTION

Figure 3:
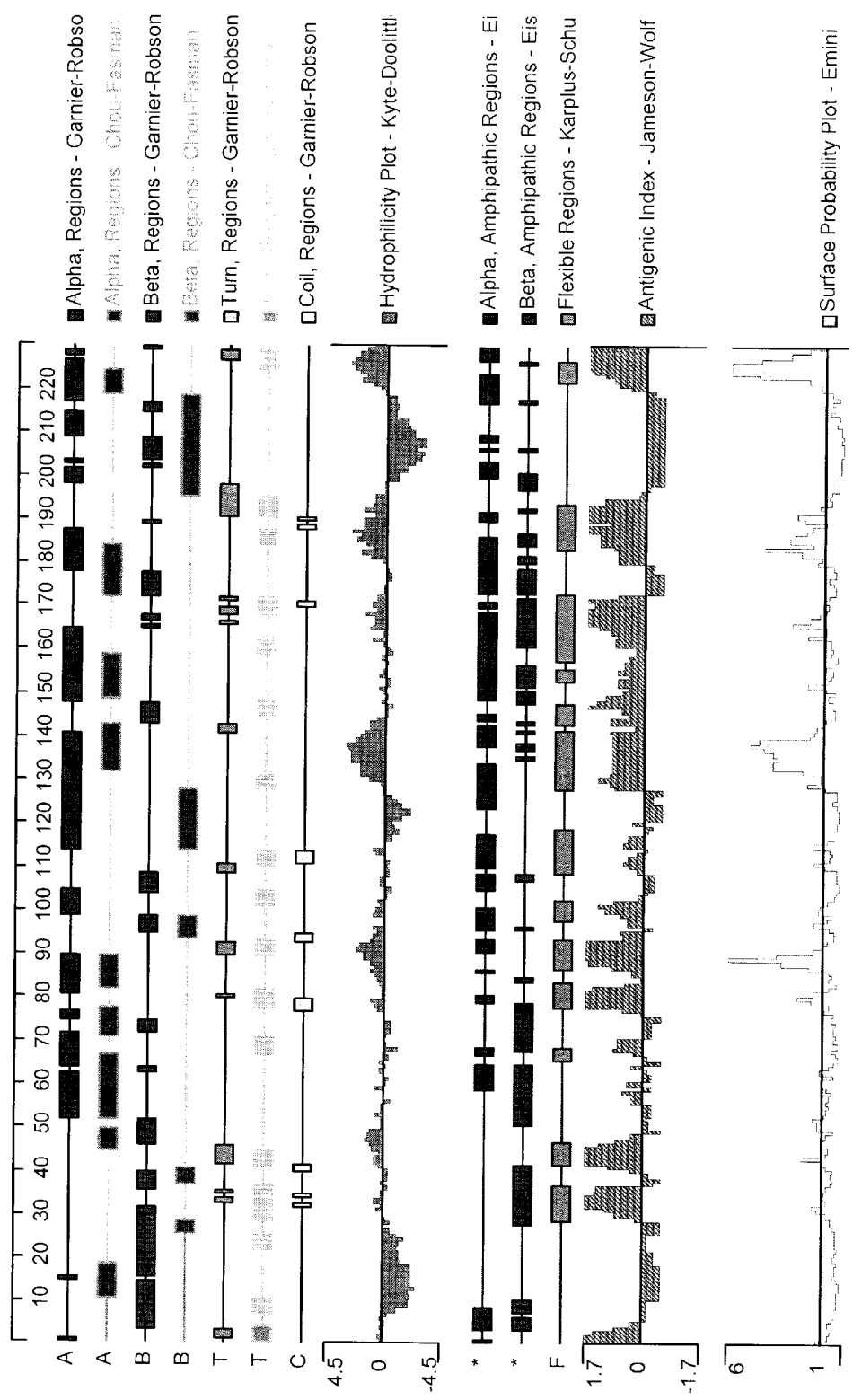
FIG. 3 provides an analysis of the T1R-like ligand II amino acid sequence. Alpha, beta, turn and coil regions; hydrophilicity and hydrophobicity; amphipathic regions; flexible regions; antigenic index and surface probability are shown.

The present invention provides an isolated nucleic acid molecule comprising a polynucleotide encoding a T1R-like ligand II protein having an amino acid sequence shown in FIGS. 1A–1B (SEQ ID NO:2), which was determined by sequencing a cloned cDNA. The T1R-like ligand II protein of the present invention shares sequence homology with the T1R ligand (SEQ ID NO:3).

The nucleotide sequence in FIGS. 1A–1B (SEQ ID NO:1) was obtained by sequencing the HE9BK24 clone, which was deposited on July 12, 1996 at the American Type Culture Collection, Patent Depository, 10801 University Boulevard, Manassas, Va. 20110-2209, and given accession number 97655. The deposited clone is contained in the pBluescript SK(-) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of peptide, polypeptides or proteins encoded by DNA molecules determined herein were expected by translation of a DNA sequence determined as above. Therefore, as is known in the art for any DNA sequence determined by this automated approach, any nucleotide sequence determined herein can contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the expected amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence is replaced by the ribonucleotide uridine (U). For instance, reference to an RNA molecule having the sequence in SEQ ID NO:1 set forth using deoxyribonucleotide abbreviations is intended to indicate an RNA molecule having a sequence in which each deoxynucleotide A, G or C in SEQ ID NO:1 has been replaced by the corresponding ribonucleotide A, G or C, and each deoxynucleotide T has been replaced by a ribonucleotide U.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Using the information provided herein, such as the nucleotide sequence in FIGS. 1A–1B (SEQ ID NO:1), a nucleic acid molecule of the present invention encoding an T1R-like ligand II polypeptide can be obtained using standard cloning and screening procedures, such as those for cloning cDNAs using mRNA as starting material. Illustrative of the invention, the nucleic acid molecule described in FIGS. 1A–1B (SEQ ID NO:1) was discovered in a cDNA library derived from nine week old human embryo tissue. Further, the gene was also found in cDNA libraries derived from the following types of human cells: prostate, anergic T-cell, TF274 stromal, WI 38, Soares breast, and Soares placenta.

The T1R-like ligand II cDNA contains an open reading frame encoding a protein of about 229 amino acid residues whose initiation codon is at positions 55-57 of the nucleotide sequence shown in SEQ ID NO. 1; a predicted leader sequence of about 26 amino acid residues and a deduced molecular weight of about 26 kDa. The amino acid sequence of the mature T1R-like ligand II protein is shown in SEQ ID NO:2 from amino acid residue 1 to residue 203. The mature T1R-like ligand II protein has three main structural domains. These include the extracellular domain, from amino acid residue about I to about 168 in SEQ ID NO:2; the transmembrane domain, from amino acid residue about 169 to about 191 in SEQ ID NO:2; and the intracellular domain, from amino acid residue about 192 to about 203 in SEQ ID NO:2. The T1R-like ligand II protein of the present invention in SEQ ID NO:2 is about 56 % identical and about 75 % similar to the T1R ligand, which can be accessed on GenBank as Accession No. U41804.

As indicated, the present invention also provides the mature form(s) of the T1R-like ligand II protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature T1R-like ligand II polypeptides having the amino acid sequence encoded by the cDNA clone contained in the host identified as ATCC Deposit No. 97655 and as shown in SEQ ID NO:2. By the mature T1R-like ligand II protein having the amino acid sequence encoded by the cDNA clone contained in the host identified as ATCC Deposit 97655 is meant the mature form(s) of the T1R-like ligand II protein produced by expression in a mammalian cell (e.g., COS cells, as described below) of the complete open reading frame encoded by the human DNA sequence of the clone contained in the vector in the deposited host. As indicated below, the mature T1R-like ligand II having the amino acid sequence encoded by the cDNA clone contained in ATCC Deposit No. 97655 may or may not differ from the predicted "mature" T1R-like ligand II protein shown in SEQ ID NO:2 (amino acids from about 1 to about 203) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino acid terminus of the mature protein. The accuracy of predicting the cleavage points of known mammalian secretory proteins for each of these methods is in the range of 75-80%. von Heinje, supra. However, the two methods do not always produce the same predicted cleavage point(s) for a given protein.

As one of ordinary skill would appreciate, due to the possibilities of sequencing errors discussed above, as well as the variability of cleavage sites for leaders in different known proteins, the actual T1R-like ligand II encoded by the deposited cDNA comprises about 229 amino acids, but can be anywhere in the range of 215-245 amino acids; and the deduced leader sequence of this protein is about 26 amino acids, but can be anywhere in the range of about 15 to about 30 amino acids. Further, for example, the exact locations of the T1R-like ligand II protein extracellular, intracellular and transmembrane domains in SEQ ID NO:2 may vary slightly (e.g., the exact amino acid positions may differ by about 1 to about 5 residues compared to that shown in SEQ ID NO:2) depending on the criteria used to define the domain.

As indicated, nucleic acid molecules of the present invention can be in the form of RNA, such as mRNA, or in the form of DNA, including, for instance, cDNA and genomic DNA obtained by cloning or produced synthetically. The DNA can be double-stranded or single-stranded. Single-stranded DNA or RNA can be the coding strand, also known as the sense strand, or it can be the non-coding strand, also referred to as the anti-sense strand.

Isolated nucleic acid molecules of the present invention include DNA molecules comprising an open reading frame (ORF) with an initiation codon at positions 55-57 of the nucleotide sequence shown in FIGS. 1A–1B (SEQ ID NO:1) and further include DNA molecules which comprise a sequence substantially different that all or part of the ORF whose initiation codon is at position 55-57 of the nucleotide sequence in FIGS. 1A–1B (SEQ ID NO:1) but which, due to the degeneracy of the genetic code, still encode the T1R-like ligand II protein or a fragment thereof. Of course, the genetic code is well known in the art. Thus, it would be routine for one skilled in the art to generate the degenerate variants described above.

In another aspect, the invention provides isolated nucleic acid molecules encoding the T1R-like ligand II protein having an amino acid sequence encoded by the cDNA clone contained in the plasmid deposited as ATCC Deposit No. 97655 on Jul. 12, 1996. Preferably, this nucleic acid molecule will encode the mature polypeptide encoded by the above-described deposited cDNA clone.

The invention further provides an isolated nucleic acid molecule having the nucleotide sequence shown in FIGS. 1A–1B (SEQ ID NO:1) or the nucleotide sequence of the T1R-like ligand II cDNA contained in the above-described deposited clone, or having a sequence complementary to one of the above sequences. Such isolated molecules, particularly DNA molecules, are useful as probes for gene mapping by in situ hybridization with chromosomes and for detecting expression of the T1R-like ligand II gene in human tissue, for instance, by Northern blot analysis. As described in detail herein, detecting altered T1R-like ligand II gene expression in certain tissues may be indicative of certain disorders.

The present invention is further directed to fragments of the isolated nucleic acid molecules described herein. By a fragment of an isolated nucleic acid molecule having, for example, the nucleotide sequence of the deposited cDNA ATCC No. 97655, a nucleotide sequence encoding the polypeptide sequence encoded by the deposited cDNA, a nucleotide sequence encoding the polypeptide sequence depicted in FIGS. 1A–1B (SEQ ID NO:2), the nucleotide sequence shown in FIGS. 1A–1B (SEQ ID NO:1), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, 600 or 650 nt in length. These fragments have numerous uses which include, but are not limited to, diagnostic probes and primers as discussed herein. Of course, larger fragments, such as those of 700-1244 nt in length are also useful according to the present invention as are fragments corresponding to most, if not all, of the nucleotide sequences of the deposited cDNA ATCC No. 97655 or as shown in FIGS. 1A–1B (SEQ ID NO:1). By a fragment at least 20 nt in length, for example, is intended fragments which include 20 or more contiguous bases from, for example, the nucleotide sequence of the deposited cDNA, or the nucleotide sequence as shown in FIG. 1 (SEQ ID NO:1).

Since the gene has been deposited and the nucleotide sequence shown in FIGS. 1A–1B (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Representative examples of T1R-like ligand II polynucleotide fragments of the invention include, for example, fragments that comprise, or alternatively, consist of, a sequence from about nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, and/or 1151 to 1210 of SEQ ID NO:1, or the complementary strand thereto, or the cDNA contained in the deposited plasmid. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding: a polypeptide comprising the T1R-like ligand II extracellular domain (amino acid residues from about 1 to about 168 in SEQ ID NO:2); a polypeptide comprising the T1R-like ligand II transmembrane domain (amino acid residues from about 169 to about 191 in SEQ ID NO:2); a polypeptide comprising the T1R-like ligand II intracellular domain (amino acid residues from about 192 to about 203 in SEQ ID NO:2); and a polypeptide comprising the T1R-like ligand II extracellular and intracellular domains having all or part of the transmembrane domain deleted. Further preferred nucleic acid fragments of the present invention include nucleic acid molecules encoding epitope-bearing portions of the T1R-like ligand II protein. In particular, isolated nucleic acid molecules are provided encoding polypeptides comprising the following amino acid residues in SEQ ID NO:2, which the present inventors have determined are hydrophilic regions of the T1R-like ligand II protein: a polypeptide comprising amino acid residues from about 17 to about 26 in SEQ ID NO:2; a polypeptide comprising amino acid residues from about 56 to about 72 in SEQ ID NO:2; a polypeptide comprising amino acid residues from about 103 to about 120 in SEQ ID NO:2; a polypeptide comprising amino acid residues from about 136 to about 149 in SEQ ID NO:2; and a polypeptide comprising amino acid residues from about 155 to about 171 in SEQ ID NO:2. Methods for determining other such epitope-bearing portions of the T1R-like ligand II protein are described in detail herein.

Preferably, the polynucleotide fragments of the invention encode a polypeptide which demonstrates a T1R-like ligand II functional activity. By a polypeptide demonstrating a T1R-like ligand II "functional activity" is meant, a polypeptide capable of displaying one or more known functional activities associated with a full-length (complete) or soluble T1R-like ligand II protein. Such functional activities include, but are not limited to, biological activity (e.g., ability to regulate (e.g., stimulate) hematopoiesis in vitro or in vivo), antigenicity [ability to bind (or compete with a T1R-like ligand II polypeptide for binding) to an anti-T1R-like ligand II antibody], immunogenicity (ability to generate antibody which binds to a T1R-like ligand II polypeptide), ability to form multimers with T1R-like ligand II polypeptides of the invention, and ability to bind to a receptor or ligand for a T1R-like ligand II polypeptide.

The functional activity of T1R-like ligand II polypeptides, and fragments, variants derivatives, and analogs thereof, can be assayed by various methods.

For example, in one embodiment where one is assaying for the ability to bind or compete with full-length T1R-like ligand II polypeptide for binding to anti-T1R-like ligand II antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a T1R-like ligand II polypeptide ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94-123. In another embodiment, physiological correlates of T1R-like ligand II binding to its substrates (signal transduction) can be assayed.

In addition, assays described herein and otherwise known in the art may routinely be applied to measure the ability of T1R-like ligand II polypeptides and fragments, variants derivatives and analogs thereof to elicit T1R-like ligand II related biological activity [e.g., to regulate (e.g., to stimulate or inhibit) hematopoiesis in vitro or in vivo]. For example, techniques known in the art (such as for example assaying for thymidine incorporation), may be applied or routinely modified to assay for the ability of the compositions of the invention to inhibit proliferation of hematopoietic cells.

Other methods will be known to the skilled artisan and are within the scope of the invention.

In addition, the present inventors have identified nucleic acid molecules having nucleotide sequences related to extensive portions of SEQ ID NO:1 which have been determined from the following related cDNA clone: HPVAA83R (SEQ ID NO:11).

The following public ESTs are related to extensive portions of SEQ ID NO:1: GenBank accession No. AA013099 (SEQ ID NO:12), GenBank accession No. AA251084 (SEQ ID NO:13), GenBank accession No. R58562 (SEQ ID NO:14), GenBank accession No. N28878 (SEQ ID NO:15), GenBank accession No. AA019348 (SEQ ID NO:16), GenBank accession No. N49615 (SEQ ID NO:17), GenBank accession No. AA112675 (SEQ ID NO:18), GenBank accession No. AA082161 (SEQ ID NO:19), GenBank accession No. H03613 (SEQ ID NO:20), GenBank accession No. R54717 (SEQ ID NO:21), GenBank accession No. H27167 (SEQ ID NO:22), GenBank accession No. AA188741 (SEQ ID NO:23), GenBank accession No. AA094735 (SEQ ID NO:24) and GenBank accession No. AA285143 (SEQ ID NO:25).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97655. By "stringent hybridization conditions" is intended overnight incubation at 42° C. in a solution comprising: 50% formamide, 5× SSC (750 mM NaCl, 75 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1× SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably at least about 30-70 nt of the reference polynucleotide. These are useful as diagnostic probes and primers as discussed above and in more detail herein.

Of course, polynucleotides hybridizing to a larger portion of the reference polynucleotide (e.g., the deposited cDNA clone), for instance, a portion 100, 150, 200, 250, 300, 350, 400, 450, 500, 550, 600, or 650 nt in length, or even to the entire length of the reference polynucleotide, also are useful as probes according to the present invention, as are polynucleotides corresponding to most, if not all, of the nucleotide sequence of the deposited cDNA or the nucleotide sequence as shown in FIGS. 1A–1B (SEQ ID NO:1). By a portion of a polynucleotide of "at least nt in length," for example, is intended 20 or more contiguous nucleotides from the nucleotide sequence of the reference polynucleotide, (e.g., the deposited cDNA or the nucleotide sequence as shown in FIGS. 1A–1B (SEQ ID NO:1)). As indicated, such portions are useful diagnostically either as a probe according to conventional DNA hybridization techniques or as primers for amplification of a target sequence by the polymerase chain reaction (PCR), as described, for instance, in Sambrook, J. et al., eds., *Molecular Cloning, A Laboratory Manual,* 2nd. edition, Cold Spring Harbor Laboratory Press, Cold Spring Harbor, N.Y. (1989).

Since an T1R-like ligand II cDNA clone has been deposited and its determined nucleotide sequence is provided in FIGS. 1A–1B (SEQ ID NO:1), generating polynucleotides which hybridize to a portion of the T1R-like ligand II cDNA molecule would be routine to the skilled artisan. For example, restriction endonuclease cleavage or shearing by sonication of the T1R-like ligand II cDNA clone could easily be used to generate DNA portions of various sizes which are polynucleotides that hybridize to a portion of the T1R-like ligand II cDNA molecule. Alternatively, the hybridizing polynucleotides of the present invention could be generated synthetically according to known techniques.

Of course, a polynucleotide which hybridizes only to a poly A sequence (such as the 3' terminal poly(A) tract of the T1R-like ligand II cDNA shown in FIGS. 1A–1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule contain a poly (A) stretch or the complement thereof (e.g., practically any double-stranded cDNA clone).

As indicated, nucleic acid molecules of the present invention which encode the T1R-like ligand II can include, but are not limited to, those encoding the amino acid sequence of the mature polypeptide, by itself, the coding sequence for the mature polypeptide and additional sequences, such as those encoding the about 26 amino acid leader sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing— including splicing and polyadenylation signals, e.g., ribosome binding and stability of mRNA; an additional coding sequence which codes for additional amino acids, such as those which provide additional functionalities. Thus, the sequence encoding the polypeptide can be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are publicly and/or commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin (HA) protein, which has been described by Wilson et al., *Cell* 37:767 (1984). Other such fusion proteins include the T1R-like ligand II protein or a fragment thereof fused to Fc at the N- or C-terminus.

The present invention further relates to variants of the nucleic acid molecules of the present invention, which encode portions, analogs or derivatives of the T1R-like ligand II protein. Variants can occur naturally, such as a natural allelic variant. By an "allelic variant" is intended one of several alternate forms of a gene occupying a given locus on a chromosome of an organism. Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells et al., Philos. Trans. R. Soc. London SerA 317:415 (1986)).

Such variants include those produced by nucleotide substitutions, deletions or additions. The substitutions, deletions or additions can involve one or more nucleotides. The variants can be altered in coding or non-coding regions or both. Alterations in the coding regions can produce conservative or non-conservative amino acid substitutions, deletions or additions. Especially preferred among these are silent substitutions, additions and deletions, which do not alter the properties and activities of the T1R-like ligand II or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 203 in SEQ ID NO:2; (d) a nucleotide sequence encoding the polypeptide having the amino acid sequence encoded by the cDNA clone contained in ATCC Deposit No. 97655; (e) a nucleotide sequence encoding the mature T1R-like ligand II polypeptide having the amino acid sequence encoded by the cDNA clone contained in ATCC Deposit No. 97655; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a T1R-like ligand II polypeptide is intended that the nucleotide sequence of the polynucleotide is identical to the reference sequence except that the polynucleotide sequence may include up to five mutations per each 100 nucleotides of the reference nucleotide sequence encoding the T1R-like ligand II polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence may be inserted into the reference sequence. These mismatches of the reference sequence can occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire T1R-like ligand II encoding nucleotide sequence shown in FIGS. 1A–1B (SEQ ID NO:1) or any T1R-like ligand II polynucleotide fragment (e.g., a polynucleotide encoding the amino acid sequence of any of the T1R-like ligand II—and/or C-terminal deletions described herein), variant, derivative or analog, as described herein.

As a practical matter, whether any particular nucleic acid molecule is at least 90%, 95%, 96%, 97%, 98% or 99% identical to, for instance, the encoding nucleotide sequence shown in FIGS. 1A–1B (SEQ ID NO:1), or to the nucleotide sequence of the deposited cDNA plasmid, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty= 1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequences disclosed herein, (e.g., encoding a polypeptide having the amino acid sequence of an N and/or C terminal deletion disclosed herein, such as, for example, a nucleic acid molecule encoding amino acids -26 to 203 of SEQ ID NO:2), irrespective of whether they encode a polypeptide having T1R-like ligand II functional activity. This is because even where a particular nucleic acid molecule does not encode a polypeptide having T1R-like ligand II functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having T1R-like ligand II functional activity include, inter alia, (1) isolating a T1R-like ligand II gene or allelic or splice variants thereof in a cDNA library; (2) in situ hybridization (e.g., "FISH") to metaphase chromosomal spreads to provide precise chromosomal location of the T1R-like ligand II gene, as described in Verma et al., Human Chromosomes: A Manual of Basic Techniques, Pergamon Press, New York (1988); and (3) Northern Blot analysis for detecting T1R-like ligand II mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having T1R-like ligand II functional activity. By "a polypeptide having T1R-like ligand II functional activity" is intended polypeptides exhibiting activity similar, but not necessarily identical, to a functional activity of the T1R-like ligand II polypeptides of the present invention (e.g., complete (full-length) T1R-like ligand II, mature T1R-like ligand II and soluble T1R-like Ligand II (e.g., having sequences contained in the extracellular domain of T1R-like ligand II) as measured, for example, in a particular immunoassay or biological assay. For example, a T1R-like ligand II functional activity can routinely be measured by determining the ability of a T1R-like ligand II polypeptide to bind a T1R-like ligand II ligand. T1R-like ligand II functional activity may also be measured by determining the ability of a polypeptide, such as cognate ligand which is free or expressed on a cell surface, to induce hematopoiesis in cells expressing the polypeptide.

T1R-like ligand II activity can be further assayed using known receptor binding assays (Mitcham, J. L. et al., *J. Biol. Chem.* 271:5777-5783 (1996); and Gayle, M. A. et al., *J. Biol. Chem.* 271:5784-5789 (1996)). These assays include an NF-κB gel shift assay, an in vitro Thr-669 kinase assay, and an IL-8 promoter activation assay.

To perform these assays, it is first necessary to transfect mammalian cells with an expression vector containing the cDNA for a suitable receptor. For example, an expression vector containing the cDNA for the T1/ST2 receptor can be used. This cDNA can be obtained as described (Klemenz, R. et al., *Proc. Natl. Acad. Sci. U.S.A.* 86:5708-5712 (1989); Tominaga, S., *FEBS Lett.* 258:301-304; Bergers, G. et al. *EMBO J.* 13:1176-1188)). Alternatively, T1/ST2 cDNA can be amplified using the polymerase chain reaction. A commercially available cDNA library, prepared from mRNA from a suitable tissue or cell type (such as NIH-3T3 cells (Klemenz, R. et al., *Proc. Natl. Acad. Sci. U.S.A.* 86:5708-5712 (1989)), can be used as template. Using any of several transfection methods well known to those of ordinary skill in the art, a suitable cell line (e.g., COS 7 cells) can be transfected with the T1/ST2 expression plasmid. Expression of the receptor can be verified by radioimmunoassay (see Mitcham, J. L. et al., *J. Biol. Chem.* 271:5777-5783 (1996)). One to three days post-transfection, confluent transfected COS7 cells are stimulated with 1-10 ng of T1R-like ligand II protein for 15 minutes to 20 hours. Duration of stimulation by T1R-like ligand II protein will vary, depending on which assay is used, and can be determined using only routine experimentation.

To perform the NF-κB assay, nuclear extracts from transfected cells are prepared immediately after stimulation (Ostrowski, J. et al., *J. Biol. Chem.* 266: 12722-12733 (1991)). A double-stranded synthetic oligonucleotide probe (5' TGACAGAGGGACTTTCCGAGAGGA 3 ' (SEQ ID NO:10)) containing the NF-κB enhancer element from the immunoglobulin κ light chain is 5'-end labeled by phosphorylation with [$\gamma$-$^{32}$P]ATP. Nuclear extracts (10 $\mu$g) are incubated with radiolabeled probe for 20 minutes at room temperature, and protein-DNA complexes are resolved by electrophoresis in a 0.5× TBE, 10% polyacrylamide gel.

To perform the in vitro Thr-669 kinase assay, cytoplasmic extracts of transfected cells are prepared immediately after stimulation (Bird, T. A. et al., *Cytokine* 4:429-440 (1992)). 10 $\mu$l of cell extract is added to 20 $\mu$l of reaction mixture containing 20 mM HEPES buffer (pH 7.4), 15 mM MgC$_2$, 15 $\mu$M ATP, 75 $\mu$Ci/ml [$\gamma$-$^{32}$P]ATP, and 750 $\mu$M substrate peptide (residues 663-673 of EGFR). Blanks are incubated with distilled H$_2$O in place of the peptide. After incubation at 30° C. for 20 minutes, the reactions are terminated by addition of formic acid. Reactions are cleared by centrifugation, and 30 $\mu$l of supernatant are spotted on phosphocellulose paper discs. After washing (three times with 75 mM orthophosphoric acid) and drying, peptide-incorporated counts are determined by monitoring Cerenkov counts. Results are expressed as the ratio of Thr-669 kinase activity detected in nonstimulated cells compared to activity detected in stimulated cells.

To perform the IL-8 promoter activation assay, COS7 cells (1×10$^5$ cells per well in a multi-well tissue culture plate) are cotransfected with the T1/ST2 receptor expression vector and the pIL8p reporter plasmid (Mitcham, J. L. et al., *J. Biol. Chem.* 271:5777-5783 (1996)). One day post-transfection, the medium is changed and cells are either stimulated with 1 ng/ml IL-1α or are left stimulated. 12-16 hours post-stimulation, cells are washed twice with binding medium containing 5% (w/v) non-fat dry milk (5% MBM) and blocked with 2 ml of 5% MBM at room temperature for 30 minutes. Cells are then incubated at room temperature for 60-90 minutes with 1.5 ml/well of 5% MBM containing 1 $\mu$g/ml of an anti-IL-2Ra antibody (R&D Systems, Minneapolis, Minn.) with gentle rocking. Cells are washed once with 5% MBM and incubated with 1 ml/well of 5% MBM containing 1:100 dilution of $^{125}$I-goat anti-mouse IgG (Sigma, St. Louis, Mo.) for 60 minutes at room temperature. Wells are washed four times with 5% MBM and twice with phosphate-buffered saline. Wells are stripped by the addition of 1 ml of 0.5 M NaOH, and total counts are determined. Results are expressed as total cpm averaged over two duplicate or three triplicate wells.

Thus, "a polypeptide having T1R-like ligand II protein activity" includes polypeptides that exhibit T1R-like ligand II protein activity in at least one of the above-described assays.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 1A–1B (SEQ ID NO:1), or fragments thereof, will encode polypeptides "having T1R-like ligand II functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having T1R-like ligand II functional activity. This is because the skilled artisan is fully aware of amino acid substitutions that are either less likely or not likely to significantly effect protein function (e.g., replacing one aliphatic amino acid with a second aliphatic amino acid), as further described herein.

For example, guidance concerning how to make phenotypically silent amino acid substitutions is provided in Bowie, J. U. et al., *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of T1R-like ligand II polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia, and pA2 available from Qiagen. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., T1R-like ligand II coding sequence), and/or to include genetic material (e.g., heterologous polynucleotide sequences) that is operably associated with T1R-like ligand II polynucleotides of the invention, and which activates, alters, and/or amplifies endogenous T1R-like ligand II polynucleotides. For example, techniques known in the art may be used to operably associate heterologous control regions (e.g., promoter and/or enhancer) and endogenous T1R-like ligand II polynucleotide sequences via homologous recombination (see, e.g., U.S. Pat. No. 5,641,670; International Publication Number WO 96/29411; International application publication number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

In one embodiment, polynucleotides encoding T1R-like ligand II polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

Thus, the polypeptide may be expressed in a modified form, such as a fusion protein, and may include not only secretion signals but also additional heterologous functional regions. For instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition*, Vol. 852-58 (1995) and K. Johanson et al., *The Journal of Biological Chemistry*, Vol. 270, No. 16, pp 9459-9471 (1995).

The T1R-like ligand II can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

In addition, proteins of the invention can be chemically synthesized using techniques known in the art (e.g., see Creighton, 1983, Proteins: Structures and Molecular Principles, W.H. Freeman & Co., N.Y., and Hunkapiller, M., et al., Nature 310:105-111 (1984)). For example, a peptide corresponding to a fragment of the T1R-like ligand II polypeptides of the invention can be synthesized by use of a peptide synthesizer. Furthermore, if desired, nonclassical amino acids or chemical amino acid analogs can be introduced as a substitution or addition into the T1R-like ligand II polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The T1R-like ligand II proteins of the invention may be modified by either natural processes, such as posttranslational processing, or by chemical modification techniques which are well known in the art. It will be appreciated that the same type of modification may be present in the same or varying degrees at several sites in a given T1R-like ligand II polypeptide. T1R-like ligand II polypeptides may be branched, for example, as a result of ubiquitination, and they may be cyclic, with or without branching. Cyclic, branched, and branched cyclic T1R-like ligand II polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

The invention additionally, encompasses T1R-like ligand II polypeptides which are differentially modified during or after translation, e.g., by glycosylation, acetylation, phosphorylation, amidation, iodination, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of T1R-like ligand II which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Thus, polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptides and Peptides of T1R-like Ligand II

The invention further provides an isolated T1R-like ligand II polypeptide having the amino acid sequence encoded by the deposited cDNA, or the amino acid sequence in FIGS. 1A–1B (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "isolated" polypeptide or protein is intended a polypeptide or protein removed from its native environment. For example, recombinantly produced polypeptides and proteins expressed in host cells are considered isolated for purposes of the invention as are native or recombinant polypeptides and proteins which have been substantially purified by any suitable technique such as, for example, the one-step method described in Smith and Johnson, *Gene* 67:31-40 (1988).

It will be recognized in the art that some amino acid sequence of the T1R-like ligand II can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the T1R-like ligand II which show substantial T1R-like ligand II activity or which include regions of T1R-like ligand II such as the protein portions discussed herein. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the T1R-like ligand II protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the T1R-like ligand II of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given PAPAI polypeptide will not be more than 50, 40, 30, 20, 10, 5, or 3.

Amino acids in the T1R-like ligand II protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vivo proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the T1R-like ligand II polypeptide can be substantially purified by the one-step method described in Smith and Johnson, *Gene* 67.31-40 (1988).

The polypeptides of the present invention include the polypeptide encoded by the deposited cDNA including the leader; the mature polypeptide encoded by the deposited the cDNA minus the leader (i.e., the mature protein); a polypeptide comprising amino acids about -26 to about 203 in SEQ ID NO:2; a polypeptide comprising amino acids about -25 to about 203 in SEQ ID NO:2; a polypeptide comprising amino acids about 1 to about 203 in SEQ ID NO:2; as well as polypeptides at least 90% identical, and more preferably at least 95%, 96%, 97%, 98% or 99% identical to the polypeptide encoded by the deposited cDNA, to the polypeptide of SEQ ID NO :2, and also include portions of such polypeptides with at least 30 amino acids and more preferably at least 50 amino acids.

By a polypeptide having an amino acid sequence at least, for example, 95% "identical" to a reference amino acid sequence of a T1R-like ligand II polypeptide is intended that the amino acid sequence of the polypeptide is identical to the reference sequence except that the polypeptide sequence may include up to five amino acid alterations per each 100 amino acids of the reference amino acid of a T1R-like ligand II. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–1B (SEQ ID NO:2), the amino acid sequence encoded by the deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal rsidues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In another embodiment of the present invention, there are provided fragments of the polypeptides described herein. Preferred fragments include: the extracellular domain (amino acid residues from about 1 to about 168 in SEQ ID NO:2); the transmembrane domain (amino acid residues from about 169 to about 191 in SEQ ID NO:2); the intracellular domain (amino acid residues from about 192 to about 203 in SEQ ID NO:2); and the intracellular domain with all or part of the transmembrane domain deleted.

For many proteins, it is well known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other T1R-like Receptor ligand functional activities (e.g., biological activities (e.g., ability to regulate hematopoiesis), ability to multimerize, ability to bind T1R-like ligand II polypeptide ligand) may still be retained. For example, the ability of shortened T1R-like ligand II mutants to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an T1R-like ligand II mutant with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the T1R-like ligand II amino acid sequence shown in FIGS. 1A–1B (i.e., SEQ ID NO:2), up to the Lys residue at position number 198 and polynucleotides encoding such polypeptides.

In particular, the present invention provides polypeptides comprising the amino acid sequence of residues n to 202 of SEQ ID NO:2, where n is an integer from 2 to 198 corresponding to the position of the amino acid residue in SEQ ID NO:2. Preferably, N-terminal deletions of the T1R-like ligand II polypeptide of the invention shown as SEQ ID NO:2 include polypeptides comprising, or alternatively consisting of, an amino acid sequence selected from amino acid residues: F-2 to T-203; T-3 to T-203; P-4 to T-203; S-5 to T-203; L-6 to T-203; D-7 to T-203; S-8 to T-203; D-9 to T-203; F-10 to T-203; T-I 1 to T-203; F-12 to T-203; T-13 to T-203; L-14 to T-203; P-15 to T-203; A-16 to T-203; G-17 to T-203; Q-18 to T-203; K-19 to T-203; E-20 to T-203; C-21 to T-203; F-22 to T-203; Y-23 to T-203; Q-24 to T-203; P-25 to T-203; M-26 to T-203; P-27 to T-203; L-28 to T-203; K-29 to T-203; A-30 to T-203; S-31 to T-203; L-32 to T-203; E-33 to T-203; I-34 to T-203; E-35 to T-203; Y-36 to T-203; Q-37 to T-203; V-38 to T-203; L-39 to T-203; D-40 to T-203; G-41 to T-203; A-42 to T-203; G-43 to T-203; L-44 to T-203; D-45 to T-203; I-46 to T-203; D-47 to T-203; F-48 to T-203; H-49 to T-203; L-50 to T-203; A-51 to T-203; S-52 to T-203; P-53 to T-203; E-54 to T-203; G-55 to T-203; K-56 to T-203; T-57 to T-203; L-58 to T-203; V-59 to T-203; F-60 to T-203; E-61 to T-203; Q-62 to T-203; R-63 to T-203; K-64 to T-203; S-65 to T-203; D-66 to T-203; G-67 to T-203; V-68 to T-203; H-69 to T-203; T-70 to T-203; V-71 to T-203; E-72 to T-203; T-73 to T-203; E-74 to T-203; V-75 to T-203; G-76 to T-203; D-77 to T-203; Y-78 to T-203; M-79 to T-203; F-80 to T-203; C-81 to T-203; F-82 to T-203; D-83 to T-203; N-84 to T-203; T-85 to T-203; F-86 to T-203; S-87 to T-203; T-88 to T-203; I-89 to T-203; S-90 to T-203; E-91 to T-203; K-92 to T-203; V-93 to T-203; I-94 to T-203; F-95 to T-203; F-96 to T-203; E-97 to T-203; L-98 to T-203; I-99 to T-203; L-100 to T-203; D-101 to T-203; N-102 to T-203; M-103 to T-203; G-104 to T-203; E-105 to T-203; Q-106 to T-203; A-107 t T-203; Q-108 to T-203; I-109 to T-203; Q-110 to T-203; E-111 to T-203; D-112 to T-203; W-113 to T-203; K-114 to T-203; K-115 to T-203; Y-116 to T-203; I-117 to T-203; T-118 to T-203; G-119 to T-203; T-120 to T-203; D-121 to T-203; I-122 to T-203; L-123 to T-203; D-124 to T-203; M-125 to T-203; K-126 to T-203; L-127 to T-203; E-128 to T-203; D-129 to T-203; I-130 to T-203; L-131 to T-203; E-132 to T-203; S-133 to T-203; I-134 to T-203; N-135 to T-203; S-136 to T-203; I-137 to T-203; K-138 to T-203; S-139 to T-203; R-140 to T-203; L-141 to T-203; S-142 to T-203; K-143 to T-203; S-144 to T-203; G-145 to T-203; H-146 to T-203; I-147 to T-203; Q-148 to T-203; T-149 to T-203; L-150 to T-203; L-151 to T-203; R-152 to T-203; A-153 to T-203; F-154 to T-203; E-155 to T-203; A-156 to T-203; R-157 to T-203; D-158 to T-203; R-159 to T-203; N-160 to T-203; I-161 to T-203; Q-162 to T-203; E-163 to T-203; S-164 to T-203; N-165 to T-203; F-166 to T-203; D-167 to T-203; R-168 to T-203; V-169 to T-203; N-170 to T-203; F-171 to T-203; W-172 to T-203; S-173 to T-203; M-174 to T-203; V-175 to T-203; N-176 to T-203; L-177 to T-203; V-178 to T-203; V-179 to T-203; M-180 to T-203; V-181 to T-203; V-182 to T-203; V-183 to T-203; S-184 to T-203; A-185 to T-203; I-186 to T-203; Q-187 to T-203; V-188 to T-203; Y-189 to T-203; M-190 to T-203; L-191 to T-203; K-192 to T-203; S-193 to T-203; L-194 to T-203; F-195 to T-203; E-196 to T-203; D-197 to T-203; and K-198 to T-203; of SEQ ID NO:2. Polynucleotides encoding these polypeptides are also encompassed by the invention.

Additionally, N-terminal deletions of the T1R-like ligand II polypeptide of the invention shown as SEQ ID NO:2 also include polypeptides comprising, or alternatively consisting of, an amino acid sequence selected from amino acid residues: F-2 to R-168; T-3 to R-168; P-4 to R-168; S-5 to R-168; L-6 to R-168; D-7 to R-168; S-8 to R-168; D-9 to R-168; F-10 to R-168; T-11 to R-168; F-12 to R-168; T-13 to R-168; L-14 to R-168; P-15 to R-168; A-16 to R-168; G-17 to R-168; Q-18 to R-168; K-19 to R-168; E-20 to R-168; C-21 to R-168; F-22 to R-168; Y-23 to R-168; Q-24 to R-168; P-25 to R-168; M-26 to R-168; P-27 to R-168; L-28 to R-168; K-29 to R-168; A-30 to R-168; S-31 to R-168; L-32 to R-168; E-33 to R-168; I-34 to R-168; E-35 to R-168; Y-36 to R-168; Q-37 to R-168; V-38 to R-168; L-39 to R-168; D-40 to R-168; G-41 to R-168; A-42 to R-168; G-43 to R-168; L-44 to R-168; D-45 to R-168; I-46 to R-168; D-47 to R-168; F-48 to R-168; H-49 to R-168; L-50 to R-168; A-51 to R-168; S-52 to R-168; P-53 to R-168; E-54 to R-168; G-55 to R-168; K-56 to R-168; T-57 to R-168; L-58 to R-168; V-59 to R-168; F-60 to R-168; E-61 to R-168; Q-62 to R-168; R-63 to R-168; K-64 to R-168; S-65 to R-168; D-66 to R-168; G-67 to R-168; V-68 to R-168; H-69 to R-168; T-70 to R-168; V-71 to R-168; E-72 to R-168; T-73 to R-168; E-74 to R-168; V-75 to R-168; G-76 to R-168; D-77 to R-168; Y-78 to R-168; M-79 to R-168; F-80 to R-168; C-81 to R-168; F-82 to R-168; D-83 to R-168; N-84 to R-168; T-85 to R-168; F-86 to R-168; S-87 to R-168; T-88 to R-168; I-89 to R-168; S-90 to R-168; E-91 to R-168; K-92 to R-168; V-93 to R-168; I-94 to R-168; F-95 to R-168; F-96 to R-168; E-97 to R-168; L-98 to R-168; I-99 to R-168; L-100 to R-168; D-101 to R-168; N-102 to R-168; M-103 to R-168; G-104 to R-168; E-105 to R-168; Q-106 to R-168; A-107 to R-168; Q-108 to R-168; E-109 to R-168; Q-110 to R-168; E-111 to R-168; D-112 to R-168; W-113 to R-168; K-114 to R-168; K-115 to R-168; Y-116 to R-168; I-117 to R-168; T-118 to R-168; G-119 to R-168; T-120 to R-168; D-121 to R-68; I-122 to R-168; L-123 to R-168; D-124 to R-168; M-125 to R-168; K-126 to R-168; L-127 to R-168; E-128 to R-168; D-129 to R-168; I-130 to R-168; L-131 to R-168; E-132 to R-168; S-133 to R-168; I-134 to R-168; N-135 to R-168; S-136 to R-168; I-137 to R-168; K-138 to R-168; S-139 to R-168; R-140 to R-168; L-141 to R-168; S-142 to R-168; K-143 to R-168; S-144 to R-168; G-145 to R-168; H-146 to R-168; I-147 to R-168; Q-148 to R-168; T-149 to R-168; L-150 to R-168; L-151 to R-168; R-152 to R-168; A-153 to R-168; F-154 to R-168; E-155 to R-168; A-156 to R-168; R-157 to R-168; D-158 to R-168; R-159 to R-168; N-160 to R-168; I-161 to R-168; Q-162 to R-168; and E-163 to R-168; of SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities (e.g., ability to regulate hematopoiesis), ability to multimerize, ability to bind T1R-like ligand II polypeptide ligand) may still be retained. For example the ability of the shortened T1R-like ligand II mutant to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an T1R-like ligand II mutant with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the T1R-like ligand II polypeptide shown in SEQ ID NO:2, up to the Leu residue at position number 6, and polynucleotides encoding such polypeptides.

In particular, the present invention provides polypeptides comprising the amino acid sequence of residues 1 to m of FIGS. 1A–1B (i.e., SEQ ID NO:2), where m is an integer from 6 to 202 corresponding to the position of the amino acid residue in SEQ ID NO:2.

Preferably, C-terminal deletions of the T1R-like ligand II polypeptide of the invention shown as SEQ ID NO:2 include polypeptides comprising, or alternatively consisting of, an amino acid sequence selected from amino acid residues: G-1 to R-202; G-1 to S-201; G-1 to K-200; G-1 to R-199; G-1 to K-198; G-1 to D-197; G-1 to E-196; G-1 to F-195; G-1 to L-194; G-1 to S-193; G-1 to K-192; G-1 to L-191; G-1 to M-190; G-1 to Y-189; G-1 to V-188; G-1 to Q-187; G-1 to I-186; G-1 to A-185; G-1 to S-184; G-1 to V-183; G-1 to V-182; G-1 to V-181; G-1 to M-180; G-1 to V-179; G-1 to V-178; G-1 to L-177; G-1 to N-176; G-1 to V-175; G-1 to M-174; G-1 to S-173; G-1 to W-172; G-1 to F-171; G-1 to N-170; G-1 to V-169; G-1 to R-168; G-1 to D-167; G-1 to F-166; G-1 to N-165; G-1 to S-164; G-1 to E-163; G-1 to Q-162; G-1 to 1-161; G-1 to N-160; G-1 to R-159; G-1 to D-158; G-1 to R-157; G-1 to A-156; G-1 to E-155; G-1 to F-154; G-1 to A-153; G-1 to R-152; G-1 to L-151; G-1 to L-150; G-1 to T-149; G-1 to Q-148; G-1 to 1-147; G-1 to H-146; G-1 to G-145; G-1 to S-144; G-1 to K-143; G-1 to S-142; G-1 to L-141; G-Ito R-140; G-1 to S-139; G-1 to K-138; G-1 to 1-137; G-1 to S-136; G-1 to N-135; G-1 to I-134; G-1 to S-133; G-1 to E-132; G-1 to L-131; G-1 to 1-130; G-1 to D-129; G-1 to E-128; G-1 to L-127; G-1 to K-126; G-1 to M-125; G-1 to D-124; G-1 to L-123; G-1 to 1-122; G-1 to D-121; G-Ito T-120; G-1 to G-119; G-1 to T-118; G-1 to I-117; G-1 to Y-116; G-1 to K-115; G-1 to K-114; G-1 to W-113; G-1 to D-112; G-1 to E-111; G-1 to Q-110; G-1 to E-109; G-1 to Q-108; G-1 to A-107; G-1 to Q-106; G-1 to E-105; G-1 to G-104; G-1 to M-103; G-1 to N-102; G-1 to D-101; G-1 to L-100; G-1 to I-99; G-1 to L-98; G-1 to E-97; G-1 to F-96; G-1 to F-95; G-1 to I-94; G-1 to V-93; G-1 to K-92; G-1 to E-91; G-1 to S-90; G-1 to 1-89; G-1 to T-88; G-1 to S-87; G-1 to F-86; G-1 to T-85; G-1 to N-84; G-1 to D-83; G-1 to F-82; G-1 to C-81; G-1 to F-80; G-1 to M-79; G-1 to Y-78; G-1 to D-77; G-1 to G-76; G-1 to V-75; G-1 to E-74; G-1 to T-73; G-1 to E-72; G-1 to V-71; G-1 to T-0; G-1 to H-69; G-1 to V-68; G-1 to G-67; G-1 to D-66; G-1 to S-65; G-1 to K-64; G-1 to R-63; G-1 to Q-62; G-1 to E-61; G-1 to F-60; G-1 to V-59; G-1 to L-58; G-1 to T-57; G-Ito K-56; G-1 to G-55; G-1 to E-54; G-1 to P-53; G-1 to S-52; G-1 to A-51; G-1 to L-50; G-1 to H-49; G-1 to F-48; G-1 to D-47; G-1 to 1-46; G-1 to D-45; G-1 to L-44; G-1 to G-43; G-1 to A-42; G-1 to G-41; G-1 to D-40; G-1 to L-39; G-1 to V-38; G-1 to Q-37; G-1 to Y-36; G-1 to E-35; G-1 to I-34; G-1 to E-33; G-1 to L-32; G-1 to S-31; G-1 to A-30; G-1 to K-29; G-1 to L-28; G-1 to P-27; G-1 to M-26; G-1 to P-25; G-1 to Q-24; G-1 to Y-23; G-1 to F-22;

G-1 to C-21; G-1 to E-20; G-1 to K-19; G-1 to Q-18; G-1 to G-17; G-1 to A-16; G-1 to P-15; G-1 to L-14; G-1 to T-13; G-Ito F-12; G-1 to T-11; G-1 to F-10; G-1 to D-9; G-1 to S-8; G-1 to D-7; and G-1 to L-6; of SEQ ID NO:2. Polynucleotides encoding these polypeptides are also encompassed by the invention.

The invention also provides polypeptides having one or more amino acids deleted from both the amino and the carboxyl termini of an T1R-like ligand II polypeptide, which may be described generally as having residues n-m of SEQ ID NO:2, where n and m are integers as described above.

The present application is also directed to proteins containing polypeptides at least 90%, 95%, 96%, 97%, 98% or 99% identical to the T1R-like ligand II polypeptide sequence set forth herein as n to m. In preferred embodiments, the application is directed to proteins containing polypeptides at least 90%, 95%, 96%, 97%, 98% or 99% identical to polypeptides having the amino acid sequence of the specific T1R-like ligand II N- and C-terminal deletions recited herein. Polynucleotides encoding these polypeptides are also encompassed by the invention.

In certain preferred embodiments, T1R-like ligand II proteins of the invention comprise fusion proteins as described above wherein the T1R-like ligand II polypeptides are those described as n to m herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Polypeptide fragments of the present invention include polypeptides comprising or alternatively, consisting of, an amino acid sequence contained in SEQ ID NO:2, encoded by the cDNA contained in the deposited plasmid, or encoded by nucleic acids which hybridize (e.g., under stringent hybridization conditions) to the nucleotide sequence contained in the deposited plasmid, or shown in FIGS. 1A–1B (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: −25 to −1, 1 to 50, 51 to 100, 101 to 130, 131 to 169, 170 to 191, and/or 192 to 203 of SEQ ID NO:2. Moreover, polypeptide fragments can be at least 10, 20, 30, 40, 50, 60, 70, 80, 90, 100, 110, 120, 130, 140, 150, 175 or 200 amino acids in length. Polynucleotides encoding these polypeptides are also encompassed by the invention.

Among the especially preferred fragments of the invention are fragments characterized by structural or functional attributes of T1R-like ligand II. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) T1R-like ligand II (SEQ ID NO:2). Certain preferred regions are those set out in FIG. 3 and include, but are not limited to, regions of the aforementioned types identified by analysis of the amino acid sequence depicted in FIGS. 1A–1B (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of T1R-like ligand II. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of T1R-like ligand II.

The data representing the structural or functional attributes of T1R-like ligand II set forth in FIG. 3 and/or Table 2, as described herein, was generated using the various modules and algorithms of the DNA*STAR set on default parameters. In a preferred embodiment, the data presented in columns VIII, IX, XIII, and XIV of Table I can be used to determine regions of T1R-like ligand II which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table 2, be represented or identified by using tabular representations of the data presented in FIG. 3. The DNA* STAR computer algorithm used to generate FIG. 3 (set on the original default parameters) was used to present the data in FIG. 3 in a tabular format (See Table 2). The tabular format of the data in FIG. 3 may be used to easily determine specific boundaries of a preferred region.

The above-mentioned preferred regions set out in FIG. 3 and in Table 2 include, but are not limited to, regions of the aforementioned types identified by analysis of the amino acid sequence set out in FIGS. 1A–1B. As set out in FIG. 3 and in Table 2, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | T | . | 0.16 | -0.67 | * | . | . | 2.03 | 1.23 |
| Gly | 2 | . | . | . | . | T | T | . | 0.26 | -0.41 | * | . | . | 2.20 | 0.67 |
| Asp | 3 | . | . | . | . | T | T | . | -0.17 | 0.07 | . | . | . | 1.38 | 0.55 |
| Lys | 4 | . | . | . | B | . | . | T | . | 0.01 | 0.33 | * | * | . | 0.76 | 0.46 |
| Ile | 5 | . | . | . | B | . | . | . | -0.30 | 0.14 | * | * | . | 0.34 | 0.72 |
| Trp | 6 | . | . | . | B | . | . | . | 0.09 | 0.50 | * | * | . | -0.18 | 0.37 |
| Leu | 7 | . | . | . | B | . | . | T | . | -0.42 | 0.93 | * | . | . | -0.20 | 0.29 |
| Pro | 8 | . | . | . | B | . | . | T | . | -1.23 | 1.57 | * | * | . | -0.20 | 0.31 |
| Phe | 9 | . | . | . | B | . | . | T | . | -2.09 | 1.57 | . | * | . | -0.20 | 0.24 |
| Pro | 10 | . | . | . | B | . | . | T | . | -2.01 | 1.34 | . | * | . | -0.20 | 0.24 |
| Val | 11 | . | A | B | . | . | . | . | -2.31 | 1.34 | . | . | . | -0.60 | 0.13 |
| Leu | 12 | . | A | B | . | . | . | . | -2.09 | 1.41 | . | . | . | -0.60 | 0.15 |
| Leu | 13 | . | A | B | . | . | . | . | -2.69 | 1.13 | . | . | . | -0.60 | 0.10 |
| Leu | 14 | . | A | B | . | . | . | . | -2.20 | 1.39 | . | . | . | -0.60 | 0.11 |
| Ala | 15 | A | A | . | . | . | . | . | -2.20 | 1.17 | . | . | . | -0.60 | 0.20 |
| Ala | 16 | . | A | B | . | . | . | . | -2.20 | 0.91 | . | . | . | -0.60 | 0.38 |
| Leu | 17 | . | A | B | . | . | . | . | -2.20 | 0.87 | . | . | . | -0.60 | 0.34 |
| Pro | 18 | . | A | B | . | . | . | . | -2.20 | 0.87 | . | . | . | -0.60 | 0.28 |
| Pro | 19 | . | . | B | . | . | . | . | -1.60 | 1.06 | . | . | . | -0.40 | 0.23 |
| Val | 20 | . | . | B | . | . | . | . | -1.36 | 0.99 | . | . | . | -0.40 | 0.43 |
| Leu | 21 | . | . | B | . | . | . | . | -1.36 | 0.73 | . | . | . | -0.40 | 0.27 |
| Leu | 22 | . | . | B | . | . | T | . | -1.13 | 0.80 | . | . | . | -0.20 | 0.18 |
| Pro | 23 | . | . | B | . | . | T | . | -1.27 | 0.87 | . | . | . | -0.20 | 0.24 |
| Gly | 24 | . | . | B | . | . | T | . | -1.76 | 0.66 | . | . | . | -0.20 | 0.29 |
| Ala | 25 | . | . | B | . | . | T | . | -1.21 | 0.76 | . | . | . | -0.20 | 0.31 |
| Ala | 26 | . | . | B | B | . | . | . | -0.61 | 0.56 | . | . | . | -0.60 | 0.29 |
| Gly | 27 | . | . | B | B | . | . | . | -0.10 | 0.56 | . | . | . | -0.60 | 0.45 |
| Phe | 28 | . | . | B | B | . | . | . | -0.70 | 0.51 | . | * | . | -0.60 | 0.59 |
| Thr | 29 | . | . | B | . | . | T | . | -0.36 | 0.70 | . | * | F | 0.20 | 0.48 |
| Pro | 30 | . | . | B | . | . | T | . | -0.07 | 0.20 | . | * | F | 0.75 | 0.82 |
| Ser | 31 | . | . | B | . | . | T | . | 0.52 | 0.16 | . | * | F | 1.15 | 1.27 |
| Leu | 32 | . | . | . | . | . | T | C | 0.17 | -0.63 | . | * | F | 2.50 | 1.46 |
| Asp | 33 | . | . | . | . | T | T | . | 0.56 | -0.33 | . | * | F | 2.50 | 0.82 |
| Ser | 34 | . | . | . | . | . | T | C | 0.17 | -0.27 | . | * | F | 2.05 | 0.88 |
| Asp | 35 | . | . | . | . | T | T | . | 0.07 | 0.13 | . | * | F | 1.40 | 0.93 |
| Phe | 36 | . | . | B | . | . | T | . | -0.44 | -0.07 | . | * | F | 1.35 | 0.80 |
| Thr | 37 | . | . | B | B | . | . | . | 0.16 | 0.61 | . | * | . | -0.35 | 0.49 |
| Phe | 38 | . | . | B | B | . | . | . | -0.43 | 0.66 | . | * | . | -0.60 | 0.46 |
| Thr | 39 | . | . | B | B | . | . | . | -0.48 | 1.16 | . | * | . | -0.26 | 0.53 |
| Leu | 40 | . | . | . | B | . | . | C | -0.48 | 0.80 | . | * | . | 0.28 | 0.37 |
| Pro | 41 | . | . | . | . | . | T | C | 0.27 | 0.71 | . | * | . | 1.02 | 0.73 |
| Ala | 42 | . | . | . | . | T | T | . | 0.58 | -0.07 | . | . | F | 2.76 | 1.01 |
| Gly | 43 | . | . | . | . | T | T | . | 0.61 | -0.56 | . | . | F | 3.40 | 2.13 |
| Gln | 44 | . | . | . | . | T | T | . | 0.22 | -0.67 | . | . | F | 2.91 | 0.74 |
| Lys | 45 | . | A | . | . | T | . | . | 0.79 | -0.31 | . | . | F | 1.87 | 0.63 |
| Glu | 46 | . | A | B | . | . | . | . | 1.00 | -0.06 | . | . | F | 1.28 | 1.00 |
| Cys | 47 | . | A | B | . | . | . | . | 1.38 | -0.09 | . | . | . | 0.79 | 1.00 |
| Phe | 48 | . | A | B | . | . | . | . | 1.12 | -0.06 | . | . | . | 0.30 | 0.77 |
| Tyr | 49 | . | A | B | . | . | . | . | 0.91 | 0.56 | . | . | . | -0.60 | 0.44 |
| Gln | 50 | . | . | B | . | . | . | . | 0.06 | 0.99 | . | . | . | -0.25 | 1.27 |
| Pro | 51 | . | . | B | . | . | . | . | 0.10 | 1.10 | . | * | . | -0.25 | 1.21 |
| Met | 52 | A | A | . | . | . | . | . | 0.18 | 0.31 | . | * | . | -0.15 | 1.55 |
| Pro | 53 | A | A | . | . | . | . | . | 0.58 | 0.06 | . | * | . | -0.30 | 0.90 |
| Leu | 54 | A | A | . | . | . | . | . | 0.01 | 0.04 | . | * | . | -0.30 | 0.78 |
| Lys | 55 | A | A | . | . | . | . | . | 0.01 | 0.30 | . | * | . | -0.30 | 0.65 |
| Ala | 56 | A | A | . | . | . | . | . | -0.67 | -0.31 | . | * | . | 0.30 | 0.73 |
| Ser | 57 | A | A | . | . | . | . | . | -0.07 | -0.06 | . | * | . | 0.30 | 0.62 |
| Leu | 58 | A | A | . | . | . | . | . | -0.10 | -0.74 | * | * | . | 0.60 | 0.54 |
| Glu | 59 | A | A | . | . | . | . | . | 0.71 | 0.01 | * | * | . | -0.30 | 0.83 |
| Ile | 60 | A | A | . | . | . | . | . | -0.19 | -0.09 | * | * | . | 0.45 | 1.08 |
| Glu | 61 | A | A | . | . | . | . | . | -0.41 | 0.17 | * | * | . | -0.30 | 0.97 |
| Tyr | 62 | A | A | . | . | . | . | . | -0.11 | 0.17 | * | * | . | -0.30 | 0.46 |
| Gln | 63 | . | A | B | . | . | . | . | 0.36 | 0.17 | * | * | . | -0.15 | 1.10 |
| Val | 64 | A | A | . | . | . | . | . | -0.23 | -0.09 | * | * | . | 0.30 | 0.63 |
| Leu | 65 | A | A | . | . | . | . | . | 0.31 | 0.41 | . | . | . | -0.60 | 0.41 |
| Asp | 66 | A | A | . | . | . | . | . | -0.50 | 0.09 | . | . | F | -0.15 | 0.23 |
| Gly | 67 | A | . | . | . | . | T | . | -0.26 | 0.37 | * | . | F | 0.25 | 0.26 |
| Ala | 68 | A | . | . | . | . | T | . | -1.14 | -0.27 | * | * | F | 0.85 | 0.52 |
| Gly | 69 | A | . | . | . | . | T | . | -0.29 | -0.27 | . | * | . | 0.70 | 0.22 |
| Leu | 70 | A | . | . | . | . | T | . | -0.18 | -0.27 | . | * | . | 0.70 | 0.37 |
| Asp | 71 | A | A | . | . | . | . | . | -0.21 | 0.09 | . | * | . | -0.30 | 0.32 |
| Ile | 72 | . | A | B | . | . | . | . | -0.68 | 0.09 | . | * | . | -0.30 | 0.44 |
| Asp | 73 | . | A | B | . | . | . | . | -0.68 | 0.34 | . | * | . | -0.30 | 0.44 |
| Phe | 74 | . | A | B | . | . | . | . | -0.63 | 0.16 | . | * | . | -0.30 | 0.26 |
| His | 75 | A | A | . | . | . | . | . | -0.03 | 0.54 | . | * | . | -0.60 | 0.50 |
| Leu | 76 | A | A | . | . | . | . | . | -0.03 | 0.29 | . | * | . | 0.04 | 0.47 |
| Ala | 77 | . | A | . | . | . | . | C | 0.51 | 0.29 | . | * | . | 0.58 | 0.93 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 78 | . | . | . | . | . | T | C | 0.56 | -0.07 | . | * | F | 2.07 | 0.68 |
| Pro | 79 | . | . | . | . | . | T | C | 0.94 | -0.57 | * | . | F | 2.86 | 1.64 |
| Glu | 80 | . | . | . | . | T | T | . | 0.17 | -0.77 | * | . | F | 3.40 | 2.35 |
| Gly | 81 | A | . | . | . | . | T | . | 0.12 | -0.59 | . | . | F | 2.66 | 1.45 |
| Lys | 82 | A | A | . | . | . | . | . | 0.01 | -0.33 | . | . | F | 1.47 | 0.69 |
| Thr | 83 | A | A | . | . | . | . | . | 0.31 | 0.03 | . | . | F | 0.53 | 0.35 |
| Leu | 84 | A | A | . | . | . | . | . | 0.52 | 0.03 | . | * | . | 0.04 | 0.61 |
| Val | 85 | A | A | . | . | . | . | . | 0.63 | 0.00 | . | . | . | -0.30 | 0.53 |
| Phe | 86 | A | A | . | . | . | . | . | 1.02 | 0.00 | * | . | . | -0.30 | 0.71 |
| Glu | 87 | A | A | . | . | . | . | . | 0.68 | -0.49 | . | . | F | 0.94 | 1.73 |
| Gln | 88 | A | A | . | . | . | . | . | 0.99 | -0.79 | . | . | F | 1.58 | 3.13 |
| Arg | 89 | A | A | . | . | . | . | . | 1.46 | -1.43 | . | . | F | 1.92 | 6.03 |
| Lys | 90 | . | . | . | . | T | T | . | 1.46 | -1.79 | . | . | F | 3.06 | 3.44 |
| Ser | 91 | . | . | . | . | T | T | . | 2.12 | -1.14 | * | . | F | 3.40 | 1.48 |
| Asp | 92 | . | . | . | . | T | T | . | 1.81 | -1.04 | * | . | F | 3.06 | 1.03 |
| Gly | 93 | . | . | . | . | . | T | C | 0.96 | -0.56 | * | . | F | 2.37 | 0.74 |
| Val | 94 | . | . | . | B | . | . | C | 0.84 | 0.09 | . | . | . | 0.58 | 0.41 |
| His | 95 | . | . | B | B | . | . | . | 0.49 | -0.30 | . | . | . | 0.64 | 0.43 |
| Thr | 96 | . | . | B | B | . | . | . | 0.79 | 0.19 | * | * | . | -0.30 | 0.62 |
| Val | 97 | . | . | B | B | . | . | . | -0.07 | -0.24 | * | . | . | 0.45 | 1.45 |
| Glu | 98 | . | . | B | B | . | . | . | -0.07 | -0.24 | * | . | F | 0.45 | 0.79 |
| Thr | 99 | A | . | . | . | . | . | . | 0.79 | -0.31 | * | . | F | 0.65 | 0.54 |
| Glu | 100 | A | . | . | . | . | . | . | 0.58 | -0.80 | * | . | F | 1.10 | 1.22 |
| Val | 101 | A | . | . | . | . | T | . | 0.29 | -0.69 | . | . | F | 1.30 | 1.10 |
| Gly | 102 | A | . | . | . | . | T | . | 0.44 | -0.07 | . | . | F | 0.85 | 0.76 |
| Asp | 103 | A | . | . | . | . | T | . | -0.22 | 0.23 | . | . | . | 0.10 | 0.38 |
| Tyr | 104 | A | . | B | . | . | T | . | -0.61 | 0.80 | . | . | . | -0.20 | 0.27 |
| Met | 105 | . | . | B | . | . | . | . | -0.61 | 0.94 | * | . | . | -0.40 | 0.24 |
| Phe | 106 | . | . | B | . | . | . | . | 0.24 | 0.51 | * | . | . | -0.40 | 0.24 |
| Cys | 107 | . | . | B | . | . | . | . | 0.28 | 0.91 | * | * | . | -0.40 | 0.24 |
| Phe | 108 | . | . | B | . | . | . | . | -0.42 | 0.64 | * | * | . | -0.40 | 0.36 |
| Asp | 109 | . | . | . | . | T | . | . | -0.48 | 0.81 | . | . | F | 0.15 | 0.36 |
| Asn | 110 | . | . | . | . | T | T | . | -0.19 | 0.41 | * | . | F | 0.35 | 0.89 |
| Thr | 111 | . | . | . | . | . | T | C | -0.38 | 0.33 | * | . | F | 0.60 | 1.49 |
| Phe | 112 | . | . | . | . | . | T | C | -0.01 | 0.23 | * | . | F | 0.45 | 0.62 |
| Ser | 113 | . | . | . | . | . | T | C | 0.69 | 0.61 | * | . | F | 0.15 | 0.52 |
| Thr | 114 | A | . | . | B | . | . | . | 0.73 | 0.21 | * | . | F | -0.15 | 0.62 |
| Ile | 115 | A | . | . | B | . | . | . | -0.12 | -0.27 | * | . | F | 0.60 | 1.44 |
| Ser | 116 | A | . | . | B | . | . | . | -0.70 | -0.41 | * | . | F | 0.45 | 0.80 |
| Glu | 117 | A | . | . | B | . | . | . | -0.70 | -0.11 | * | . | F | 0.45 | 0.39 |
| Lys | 118 | A | . | . | B | . | . | . | -1.10 | 0.19 | . | . | F | -0.15 | 0.48 |
| Val | 119 | A | . | . | B | . | . | . | -0.79 | 0.29 | . | . | . | -0.30 | 0.31 |
| Ile | 120 | A | . | . | B | . | . | . | -0.71 | -0.10 | . | . | . | 0.30 | 0.31 |
| Phe | 121 | A | . | . | B | . | . | . | -1.30 | 0.59 | . | . | . | -0.60 | 0.13 |
| Phe | 122 | A | . | . | B | . | . | . | -2.11 | 1.27 | . | . | . | -0.60 | 0.12 |
| Glu | 123 | A | . | . | B | . | . | . | -2.16 | 1.31 | . | . | . | -0.60 | 0.14 |
| Leu | 124 | A | . | . | B | . | . | . | -1.30 | 0.63 | * | . | . | -0.60 | 0.27 |
| Ile | 125 | A | . | . | B | . | . | . | -1.01 | 0.24 | * | . | . | -0.30 | 0.51 |
| Leu | 126 | A | . | . | B | . | . | . | -0.66 | 0.07 | * | . | . | -0.30 | 0.29 |
| Asp | 127 | A | . | . | B | . | . | . | 0.04 | 0.50 | * | . | . | -0.60 | 0.35 |
| Asn | 128 | A | . | . | . | . | T | . | 0.04 | -0.19 | * | . | F | 0.85 | 0.86 |
| Met | 129 | A | . | . | . | . | T | . | 0.27 | -0.47 | * | . | F | 1.00 | 1.81 |
| Gly | 130 | A | . | . | . | . | T | . | 1.16 | -0.66 | * | . | F | 1.30 | 1.09 |
| Glu | 131 | A | . | . | . | . | T | . | 1.97 | -0.26 | * | . | F | 1.00 | 1.18 |
| Gln | 132 | A | A | . | . | . | . | . | 1.97 | -0.66 | * | . | F | 0.90 | 2.06 |
| Ala | 133 | A | A | . | . | . | . | . | 1.97 | -0.87 | * | . | F | 0.90 | 3.61 |
| Gln | 134 | A | A | . | . | . | . | . | 2.57 | -1.30 | . | . | F | 0.90 | 3.61 |
| Glu | 135 | A | A | . | . | . | . | . | 2.62 | -1.30 | . | * | F | 0.90 | 3.48 |
| Gln | 136 | A | A | . | . | . | . | . | 2.67 | -0.79 | . | . | F | 0.90 | 3.62 |
| Glu | 137 | A | A | . | . | . | . | . | 2.71 | -1.29 | . | * | F | 0.90 | 4.18 |
| Asp | 138 | A | A | . | . | . | . | . | 3.06 | -1.69 | * | * | F | 0.90 | 4.83 |
| Trp | 139 | A | A | . | . | . | . | . | 2.17 | -0.93 | * | . | F | 0.90 | 4.37 |
| Lys | 140 | A | A | . | . | . | . | . | 1.86 | -0.64 | * | . | F | 0.90 | 1.77 |
| Lys | 141 | . | A | . | . | T | . | . | 1.51 | -0.16 | * | * | F | 1.00 | 1.53 |
| Tyr | 142 | . | A | . | . | T | . | . | 1.20 | 0.27 | * | . | . | 0.25 | 1.44 |
| Ile | 143 | . | . | B | . | . | . | . | 1.20 | -0.16 | . | * | F | 0.97 | 1.04 |
| Thr | 144 | . | . | B | . | . | . | . | 0.60 | -0.16 | * | . | F | 0.99 | 0.87 |
| Gly | 145 | . | . | B | . | . | T | . | -0.26 | 0.53 | * | . | F | 0.46 | 0.39 |
| Thr | 146 | . | . | B | . | . | T | . | -0.30 | 0.46 | . | . | F | 0.63 | 0.46 |
| Asp | 147 | . | . | B | . | . | T | . | -0.66 | -0.23 | * | . | F | 1.70 | 0.53 |
| Ile | 148 | A | . | . | . | . | T | . | 0.28 | -0.10 | * | * | . | 1.38 | 0.53 |
| Leu | 149 | A | A | . | . | . | . | . | -0.22 | -0.53 | * | * | . | 1.11 | 0.73 |
| Asp | 150 | A | A | . | . | . | . | . | 0.12 | -0.33 | * | . | . | 0.64 | 0.36 |
| Met | 151 | A | A | . | . | . | . | . | 0.43 | -0.33 | * | . | . | 0.47 | 0.89 |
| Lys | 152 | A | A | . | . | . | . | . | -0.46 | -1.01 | * | * | . | 0.75 | 1.81 |
| Leu | 153 | A | A | . | . | . | . | . | -0.38 | -1.01 | * | * | F | 0.75 | 0.76 |
| Glu | 154 | A | A | . | . | . | . | . | 0.43 | -0.33 | * | * | F | 0.45 | 0.63 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 155 | A | A | . | . | . | . | . | 0.13 | -0.94 | * | * | F | 0.75 | 0.55 |
| Ile | 156 | A | A | . | . | . | . | . | -0.16 | -0.56 | * | * | . | 0.60 | 0.89 |
| Leu | 157 | A | A | . | . | . | . | . | -0.20 | -0.56 | * | . | . | 0.60 | 0.36 |
| Glu | 158 | A | A | . | . | . | . | . | 0.31 | -0.16 | * | . | F | 0.45 | 0.35 |
| Ser | 159 | A | . | . | . | . | T | . | -0.58 | 0.23 | * | . | F | 0.25 | 0.66 |
| Ile | 160 | A | . | . | . | . | T | . | -0.53 | 0.23 | * | . | F | 0.25 | 0.56 |
| Asn | 161 | A | . | . | . | . | T | . | 0.06 | -0.46 | * | * | F | 0.85 | 0.65 |
| Ser | 162 | A | . | . | . | . | T | . | 0.98 | -0.07 | * | * | F | 0.85 | 0.65 |
| Ile | 163 | A | . | . | . | . | . | . | 0.17 | -0.46 | * | * | F | 0.80 | 1.82 |
| Lys | 164 | A | . | . | . | . | . | . | 0.17 | -0.46 | * | * | F | 0.99 | 0.93 |
| Ser | 165 | . | . | B | . | . | . | . | 1.10 | -0.47 | * | * | F | 1.33 | 0.93 |
| Arg | 166 | . | . | . | . | T | . | . | 0.80 | -0.86 | * | * | F | 2.52 | 2.66 |
| Leu | 167 | . | . | B | . | . | . | . | 0.76 | -1.16 | * | * | F | 2.46 | 1.78 |
| Ser | 168 | . | . | . | . | T | T | . | 1.61 | -0.73 | * | * | F | 3.40 | 1.32 |
| Lys | 169 | . | . | . | . | T | T | . | 0.68 | -0.61 | . | * | F | 2.91 | 0.91 |
| Ser | 170 | . | . | . | . | . | T | C | 0.98 | 0.07 | * | * | F | 1.47 | 0.78 |
| Gly | 171 | . | . | . | . | T | T | . | 0.56 | -0.21 | . | * | F | 2.08 | 1.00 |
| His | 172 | . | A | B | . | . | . | . | 0.56 | -0.11 | . | . | F | 0.79 | 0.72 |
| Ile | 173 | . | A | B | . | . | . | . | 0.04 | 0.57 | * | * | . | -0.60 | 0.45 |
| Gln | 174 | . | A | B | . | . | . | . | 0.11 | 0.87 | * | * | . | -0.60 | 0.37 |
| Thr | 175 | . | A | B | . | . | . | . | -0.18 | 0.44 | * | * | . | -0.60 | 0.53 |
| Leu | 176 | . | A | B | . | . | . | . | -0.53 | 0.44 | * | * | . | -0.60 | 0.77 |
| Leu | 177 | . | A | B | . | . | . | . | -0.50 | 0.54 | * | * | . | -0.60 | 0.39 |
| Arg | 178 | A | A | . | . | . | . | . | -0.20 | 0.14 | * | * | . | -0.30 | 0.46 |
| Ala | 179 | A | A | . | . | . | . | . | -0.09 | 0.16 | * | . | . | -0.30 | 0.57 |
| Phe | 180 | A | A | . | . | . | . | . | 0.22 | -0.53 | * | * | . | 0.75 | 1.35 |
| Glu | 181 | A | A | . | . | . | . | . | 1.14 | -1.21 | * | * | . | 0.75 | 1.15 |
| Ala | 182 | A | A | . | . | . | . | . | 1.96 | -1.21 | * | . | . | 0.75 | 2.22 |
| Arg | 183 | A | A | . | . | . | . | . | 0.96 | -1.31 | * | . | F | 0.90 | 4.13 |
| Asp | 184 | A | . | . | . | . | T | . | 1.54 | -1.41 | * | * | F | 1.30 | 1.67 |
| Arg | 185 | A | . | . | . | . | T | . | 2.24 | -1.01 | * | * | F | 1.30 | 2.87 |
| Asn | 186 | A | . | . | . | . | T | . | 1.94 | -1.51 | . | * | F | 1.30 | 2.54 |
| Ile | 187 | A | . | . | . | . | T | . | 2.53 | -1.13 | . | . | F | 1.64 | 2.03 |
| Gln | 188 | . | . | . | . | . | . | C | 1.72 | -0.73 | . | . | F | 1.98 | 1.67 |
| Glu | 189 | . | . | B | . | . | . | . | 1.72 | 0.06 | . | . | F | 1.07 | 0.90 |
| Ser | 190 | . | . | . | . | . | . | C | 1.72 | -0.34 | * | . | F | 2.36 | 2.14 |
| Asn | 191 | . | . | . | . | T | T | . | 0.87 | -1.03 | * | . | F | 3.40 | 2.42 |
| Phe | 192 | . | . | . | . | T | T | . | 1.76 | -0.79 | . | * | F | 3.06 | 1.04 |
| Asp | 193 | . | . | . | . | T | T | . | 1.06 | -0.39 | . | . | F | 2.42 | 1.25 |
| Arg | 194 | . | . | . | . | T | T | . | 0.77 | 0.01 | . | . | . | 1.18 | 0.67 |
| Val | 195 | . | . | . | B | T | . | . | 0.77 | 0.53 | . | . | . | 0.14 | 0.81 |
| Asn | 196 | . | . | . | B | T | . | . | 0.17 | 0.13 | . | . | . | 0.10 | 0.65 |
| Phe | 197 | . | . | . | B | T | . | . | 0.01 | 0.74 | . | * | . | -0.20 | 0.33 |
| Trp | 198 | A | . | . | B | . | . | . | 0.01 | 1.39 | . | * | . | -0.60 | 0.33 |
| Ser | 199 | A | . | . | B | . | . | . | -0.91 | 1.14 | . | * | . | -0.60 | 0.33 |
| Met | 200 | A | . | . | B | . | . | . | -0.91 | 1.43 | * | * | . | -0.60 | 0.31 |
| Val | 201 | A | . | . | B | . | . | . | -1.77 | 1.29 | * | . | . | -0.60 | 0.22 |
| Asn | 202 | . | . | B | B | . | . | . | -1.67 | 1.01 | * | . | . | -0.60 | 0.12 |
| Leu | 203 | A | . | . | B | . | . | . | -2.23 | 1.24 | * | . | . | -0.60 | 0.12 |
| Val | 204 | . | . | B | B | . | . | . | -2.79 | 1.27 | . | . | . | -0.60 | 0.12 |
| Val | 205 | . | . | B | B | . | . | . | -3.04 | 1.27 | . | . | . | -0.60 | 0.06 |
| Met | 206 | . | . | B | B | . | . | . | -2.49 | 1.51 | * | * | . | -0.60 | 0.05 |
| Val | 207 | . | . | B | B | . | . | . | -3.08 | 1.21 | . | . | . | -0.60 | 0.09 |
| Val | 208 | . | . | B | B | . | . | . | -3.16 | 1.07 | * | . | . | -0.60 | 0.13 |
| Val | 209 | A | . | . | B | . | . | . | -2.30 | 1.11 | * | . | . | -0.60 | 0.09 |
| Ser | 210 | A | . | . | B | . | . | . | -2.30 | 0.90 | . | . | . | -0.60 | 0.21 |
| Ala | 211 | A | . | . | B | . | . | . | -1.94 | 0.90 | . | . | . | -0.60 | 0.21 |
| Ile | 212 | A | . | . | B | . | . | . | -1.69 | 1.01 | . | . | . | -0.60 | 0.44 |
| Gln | 213 | A | . | . | B | . | . | . | -1.64 | 0.99 | . | . | . | -0.60 | 0.32 |
| Val | 214 | A | . | . | B | . | . | . | -0.74 | 1.29 | . | . | . | -0.60 | 0.26 |
| Tyr | 215 | . | . | B | B | . | . | . | -0.74 | 0.79 | . | . | . | -0.60 | 0.75 |
| Met | 216 | . | . | B | B | . | . | . | -0.97 | 0.49 | . | . | . | -0.60 | 0.58 |
| Leu | 217 | A | . | . | B | . | . | . | -0.78 | 0.77 | * | * | . | -0.60 | 0.65 |
| Lys | 218 | A | . | . | B | . | . | . | -0.78 | 0.91 | * | . | . | -0.60 | 0.36 |
| Ser | 219 | A | A | . | . | . | . | . | 0.08 | 0.16 | * | . | . | -0.30 | 0.63 |
| Leu | 220 | A | A | . | . | . | . | . | 0.37 | -0.46 | * | . | . | 0.45 | 1.27 |
| Phe | 221 | A | A | . | . | . | . | . | 1.08 | -1.14 | * | . | . | 0.75 | 1.27 |
| Glu | 222 | A | A | . | . | . | . | . | 1.93 | -1.14 | * | . | F | 0.90 | 1.85 |
| Asp | 223 | A | A | . | . | . | . | . | 1.59 | -1.53 | * | . | F | 1.21 | 4.50 |
| Lys | 224 | A | A | . | . | . | . | . | 2.00 | -1.83 | . | . | F | 1.52 | 6.96 |
| Arg | 225 | A | . | . | . | . | T | . | 2.50 | -2.61 | . | . | F | 2.23 | 7.87 |
| Lys | 226 | A | . | . | . | . | T | . | 2.81 | -2.13 | . | * | F | 2.54 | 6.80 |
| Ser | 227 | . | . | . | . | T | T | . | 2.42 | -1.70 | * | . | . | 3.10 | 4.35 |
| Arg | 228 | A | . | . | . | T | T | . | 2.03 | -1.27 | . | . | . | 2.79 | 2.84 |
| Thr | 229 | . | . | B | . | . | . | . | 1.60 | -0.84 | * | . | . | 1.88 | 1.81 |

Among highly preferred fragments in this regard are those that comprise regions of T1R-like ligand II that combine several structural features, such as several of the features set out above.

The polypeptide of the present invention could be used as a molecular weight marker on SDS-PAGE gels or on molecular sieve gel filtration columns using methods well known to those of skill in the art.

As described in detail herein, the polypeptides of the present invention can be used to raise polyclonal and monoclonal antibodies, which are useful in diagnostic assays for detecting T1R-like ligand II expression as described herein or as agonists and antagonists capable of enhancing or inhibiting T1R-like ligand II protein function. Further, such polypeptides can be used in the yeast two-hybrid system to "capture" T1R-like ligand II binding proteins which are also candidate agonist and antagonist according to the present invention. The yeast two hybrid system is described in Fields and Song, *Nature* 340:245-246 (1989).

The present invention encompasses polypeptides comprising, or alternatively consisting of, an epitope of the polypeptide having an amino acid sequence of SEQ ID NO: 2, or an epitope of the polypeptide sequence encoded by a polynucleotide sequence contained in ATCC deposit No. 97655 or encoded by a polynucleotide that hybridizes to the complement of the sequence of SEQ ID NO: 1 or contained in ATCC deposit No. 97655 under stringent hybridization conditions or lower stringency hybridization conditions as defined herein. The present invention further encompasses polynucleotide sequences encoding an epitope of a polypeptide sequence of the invention (such as, for example, the sequence disclosed in SEQ ID NO:2), polynucleotide sequences of the complementary strand of a polynucleotide sequence encoding an epitope of the invention, and polynucleotide sequences which hybridize to the complementary strand under stringent hybridization conditions or lower stringency hybridization conditions defined herein.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described herein. (See, for example, Geysen et al., *Proc. Natl. Acad. Sci. USA* 81:3998-4002 (1983)). The term "antigenic epitope," as used herein, is defined as a portion of a protein to which an antibody can immunospecifically bind its antigenas determined by any method well known in the art, for example, by the immunoassays described herein. Immunospecific binding excludes non-specific binding but does not necessarily exclude cross-reactivity with other antigens. Antigenic epitopes need not necessarily be immunogenic.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Non-limiting examples of antigenic polypeptides that can be used to generate T1R-like ligand II specific antibodies or fragments, include the following: a polypeptide comprising amino acid residues from about 17 to about 26 in SEQ ID NO:2; a polypeptide comprising amino acid residues from about 56 to about 72 in SEQ ID NO:2; a polypeptide comprising amino acid residues from about 103 to about 120 in SEQ ID NO:2; a polypeptide comprising amino acid residues from about 136 to about 149 in SEQ ID NO:2; and a polypeptide comprising amino acid residues from about 155 to about 171 in SEQ ID NO:2. As indicated above, the inventors have determined that the above polypeptide fragments are antigenic regions of the T1R-like II protein.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, L. A. et al., Cell 37:767-778 (1984) at 777. The anti-peptide antibodies of the invention also are useful for purification of the mimicked protein, for instance, by adsorption chromatography using methods well known in the art.

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids). the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

The epitope-bearing peptides and polypeptides of the invention may be produced by any conventional means for making peptides or polypeptides including recombinant means using nucleic acid molecules of the invention. (See, e.g., Houghten, Proc. Natl. Acad. Sci. USA 82:5131-5135 (1985), further described in U.S. Pat. No. 4,631,211). For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A., *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MB S), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, T1R-like ligand II polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86(1988)). Fusion proteins that have a disulfide-linked dimeric structure due to the IgG part can also be more efficient in binding and neutralizing other molecules than the monomeric T1R-like ligand II protein or protein fragment alone (Fountoulakis et al., *J. Biochem.* 270:3958-3964 (1995)).

The invention further provides for the proteins containing T1R-like ligand II polypeptide sequences encoded by the polynucleotides of the invention.

The T1R-like ligand II polypeptides of the invention may be in monomers or multimers (i.e., dimers, trimers, tetramers, and higher multimers). Accordingly, the present invention relates to monomers and multimers of the T1R-like ligand II proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only T1R-like ligand II proteins of the invention (including T1R-like ligand II fragments, variants, and fusion proteins, as described herein). These homomers may contain T1R-like ligand II proteins having identical or different polypeptide sequences. In a specific embodiment, a homomer of the invention is a multimer containing only T1R-like ligand II proteins having an identical polypeptide sequence. In another specific embodiment, a homomer of the invention is a multimer containing T1R-like ligand II proteins having different polypeptide sequences. In specific embodiments, the multimer of the invention is a homodimer (e.g., containing T1R-like ligand II proteins having identical or different polypeptide sequences) or a homotrimer (e.g., containing T1R-like ligand II proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the T1R-like ligand II gene) in addition to the T1R-like ligand II proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the T1R-like ligand II proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA plasmid). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a T1R-like ligand II fusion protein. In one example, covalent associations are between the heterologous sequence contained in a fusion protein of the invention (see, e.g., U.S. Pat. No. 5,478,925). In a specific example, the covalent associations are between the heterologous sequence contained in a T1R-like ligand II -Fc fusion protein of the invention (as described herein). In another specific example, covalent associations of fusion proteins of the invention are between heterologous polypeptide sequences from another protein that is capable of forming covalently associated multimers, such as for example, oseteoprotegerin (see, e.g., International Publication No. WO 98/49305, the contents of which are herein incorporated by reference in its entirety).

In another embodiment, two or more T1R-like ligand II polypeptides of the invention are joined through peptide linkers. Examples include those peptide linkers described in U.S. Pat. No. 5,073,627 (hereby incorporated by reference). Proteins comprising multiple T1R-like ligand II polypeptides separated by peptide linkers may be produced using conventional recombinant DNA technology.

Another method for preparing multimer T1R-like ligand II polypeptides of the invention involves use of T1R-like ligand II polypeptides fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric T1R-like ligand II proteins are those described in International application publication nunmper WO 94/10308, hereby incorporated by reference. Recombinant fusion proteins comprising a soluble T1R-like ligand II polypeptide fused to a peptide that dimerizes or trimerizes in solution are expressed in suitable host cells, and the resulting soluble multimeric T1R-like ligand II is recovered from the culture supernatant using techniques known in the art.

In another example, proteins of the invention are associated by interactions between Flag(r) polypeptide sequence contained in Flag(r)-T1R-like ligand II fusion proteins of the invention. In a further embodiment, associations proteins of the invention are associated by interactions between heterologous polypeptide sequence contained in Flag(r)-T1R-like ligand II fusion proteins of the invention and anti-Flag(r) antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925. which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The entire disclosure of each document cited in this section on "Polypeptides and Peptides" is hereby incorporated herein by reference.

Fusion Polypeptides

As one of skill in the art will appreciate, and as discussed above, the polypeptides of the present invention can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as modulating the activity of T1R-like ligand II agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments into a desired T1R-like ligand II molecule by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of apolynucleotide encoding a polypeptide of the invention may be recombined with one or more components, motifs, sections, parts, domains, fragments, etc. of one or more heterologous molecules. In preferred embodiments, the heterologous molecules are members of the IL-1R family, for example IL-1RI, IL-1RII, and sIL-1RII.

Transgenic Animals

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-

6152 (1985)), blastocysts or embryos; gene targeting in embryonic stem cells (Thompson et al., Cell 56:313-321 (1989)); electroporation of cells or embryos (Lo, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety. Further, the contents of each of the documents recited in this paragraph is herein incorporated by reference in its entirety.

Further techniques known in the art may be used to introduce the transgene (i.e., nucleic acids of the invention) into animals include, for example, those techniques described in U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of T1R-like ligand II polypeptides, studying conditions and/or disorders associated with aberrant T1R-like ligand II expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e. animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

T1R-like Ligand II Antibodies and Antibody Therapy

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described herein and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or $K_d$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85 %. at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described herein). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4) :1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9) :1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail herein, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronicpolyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 1879-18 (1997); Burton et al., Advances in Immunology 57:191-280 (1994); PCT application No. PCT/GB91/011134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail herein. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska, et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The invention further provides polynucleotides comprising a nucleotide sequence encoding an antibody of the invention and fragments thereof. The invention also encompasses polynucleotides that hybridize under stringent or lower stringency hybridization conditions, e.g., as defined herein, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, NY and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described herein. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed herein, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described herein, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed herein.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5): 155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., herein, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, herein, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fe part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767(1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase: examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, a-interferon, nerve growth factor, platelet derived growth factor, tissue plasminogen activator, anapoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see e.g., Ausubel et al., eds, 1994, Current Protocols in Molecular Biology. Vol. 1, John Wiley & Sons, Inc., New York, which is incorporated by reference herein in its entirety). Exemplary immunoassays are described briefly herein (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 40 C, adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail herein. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or $K_d$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Gene Therapy

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding a T1R-like ligand II polypeptide, antibody, antagonist, agonist, or fragment or variant thereof, said nucleic acid sequences being part of expression vectors that express the T1R-like ligand II polypeptide, a polypeptide fragment, antibody, antagonist, agonist, or variant thereof in a suitable host. In particular, such nucleic acid sequences have promoters operably linked to the coding region, said promoter being inducible or constitutive, and, optionally, tissue-specific. In another particular embodiment, nucleic acid molecules are used in which the coding sequences and any other desired sequences are flanked by regions that promote homologous recombination at a desired site in the genome, thus providing for intrachromosomal expression of the encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody. As mentioned previously, polypeptides, polypeptide fragments, antagonists, agonists, and variants thereof may also be expressed.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding a polypeptide of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the polypeptide to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al. J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434(1991); Rosenfeldet al., Cell 68:143-155(1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method oftransfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. Particularly preferred are CD34+ cells.

In a preferred embodiment, the cell used for gene therapy is auto logous to the patient.

In an embodiment in which recombinant cells are used in gene therapy, nucleic acid sequences are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)). Particularly preferred are CD 34+ cells.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Antisense and Ribozyme Antagonists

In specific embodiments, antagonists according to the present invention are nucleic acids corresponding to the sequences contained in T1R-like ligand II, or the complementary strand thereof, and/or to nucleotide sequences contained in the deposited plasmid ATCC Deposit No. 97655. In one embodiment, antisense sequence is generated internally by the organism, in another embodiment, the antisense sequence is separately administered (see, for example, O'Connor, J., Neurochem. 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the T1R-like ligand II antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the T1R-like ligand II antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding T1R-like ligand II, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of a T1R-like ligand II gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded T1R-like ligand II antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a T1R-like ligand II RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of the T1R-like ligand II shown in FIGS. 1A–1B could be used in an antisense approach to inhibit translation of endogenous T1R-like ligand II mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of T1R-like ligand II mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci. 84:648-652(1987); PCT Publication No. WO88/09810) or the blood-brain barrier (see, e.g., PCT Publication No. WO89/10134), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5 -(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, $^2$-methylguanine, 3-methylcytosine, 5-methylcytosine, N6-adenine, 7-methylguanine , 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625-6641 (1987)). The oligonucleotide is a 2'-0-methylribonucleotide (Inoue et al., Nucl. Acids Res. 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the T1R-like ligand II coding region sequence could be used, those complementary to the transcribed untranslated region are most preferred.

Potential antagonists according to the invention also include catalytic RNA, or a ribozyme (See, e.g., PCT International Publication WO 90/11364; Sarver et al., Science 247:1222-1225 (1990). While ribozymes that cleave mRNA at site specific recognition sequences can be used to destroy T1R-like ligand II mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of T1R-like ligand II (FIGS. 1A–1B (SEQ ID NO: 1)). Preferably, the ribozyme is engineered so that the cleavage recognition site is located near the 5' end of the T1R-like ligand II mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express T1R-like ligand II in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous T1R-like ligand II messages and inhibit translation. Since ribozymes unlike antisense molecules, are catalytic, a lower intracellular concentration is required for efficiency.

Endogenous gene expression can also be reduced by inactivating or "knocking out" the T1R-like ligand II gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of T1R-like ligand II (e.g., fragments of the T1R-like ligand II shown in FIG. 2 (SEQ ID NO:2) that include the ligand binding domain from the extracellular region of the full length receptor). Such soluble forms of the T1R-like ligand II, which may be naturally occurring or synthetic, antagonize T1R-like ligand II mediated signaling by competing with the cell surface bound forms of the receptor for binding to T1R-like ligand II ligands. Antagonists of the present invention also include T1R-like ligand II Fc fusion proteins.

Antibodies according to the present invention may be prepared by any of a variety of standard methods using T1R-like ligand II receptor immunogens of the present invention. Such T1R-like ligand II receptor immunogens include the T1R-like ligand II protein shown in FIGS. 1A–1B (SEQ ID NO:2) (which may or may not include a leader sequence) and polypeptide fragments of the receptor comprising the ligand binding, extracellular, transmembrane, the intracellular domains of T1R-like ligand II, or any combination thereof.

Polyclonal and monoclonal antibody agonists or antagonists according to the present invention can be raised according to the methods disclosed herein and and/or known in the art, such as, for example, those methods described in Tartaglia and Goeddel, J. Biol. Chem. 267(7):4304-4307(1992)); Tartaglia et al., Cell 73:213-216 (1993)), and PCT Application WO 94/09137 (the contents of each of these three applications are herein incorporated by reference in their entireties), and are preferably specific to polypeptides of the invention having the amino acid sequence of SEQ ID NO:2.

T1R-like Ligand II Related Disorder Diagnosis

For T1R-like ligand II related disorders, it is believed that substantially altered (increased or decreased) levels of T1R-like ligand II gene expression can be detected in tissue or other cells or bodily fluids (e.g., sera, plasma, urine, synovial fluid or spinal fluid) taken from an individual having such a disorder, relative to a "standard" T1R-like ligand II gene expression level, that is, the T1R-like ligand II gene expression level in tissue or bodily fluids from an individual not having the disorder. Thus, the invention provides a diagnostic method useful during diagnosis of an T1R-like ligand II-related disorder, which involves measuring the expression level of the gene encoding the T1R-like ligand II in tissue or other cells or body fluid from an individual and comparing the measured gene expression level with a standard T1R-like ligand II gene expression level, whereby an increase or decrease in the gene expression level compared to the standard is indicative of an T1R-like ligand II related disorder.

T1R-like ligand II-related disorders are believed to include, but are not limited to, leukemia, lymphoma, arteriosclerosis, autoimmune diseases, inflammatory diseases, Alzheimer's disease, ophthalmic diseases, apoptosis, intrauterine growth retardation, preeclampsia, pemphigus and psoriasis.

By individual is intended mammalian individuals, preferably humans. By "measuring the expression level of the gene encoding the T1R-like ligand II" is intended qualitatively or quantitatively measuring or estimating the level of the T1R-like ligand II protein or the level of the mRNA encoding the T1R-like ligand II protein in a first biological sample either directly (e.g., by determining or estimating absolute protein level or mRNA level) or relatively (e.g., by comparing to the T1R-like ligand II protein level or mRNA level in a second biological sample). Preferably, the T1R-like ligand II protein level or mRNA level in the first biological sample is measured or estimated and compared to a standard T1R-like ligand II protein level or mRNA level, the standard being taken from a second biological sample obtained from an individual not having the disorder or being determined by averaging levels from a population of individuals not having the disorder. As will be appreciated in the art, once a standard T1R-like ligand II protein level or mRNA level is known, it can be used repeatedly as a standard for comparison.

By "biological sample" is intended any biological sample obtained from an individual, body fluid, cell line, tissue culture, or other source which contains T1R-like ligand II protein or mRNA. As indicated, biological samples include body fluids (such as sera, plasma, urine, synovial fluid and spinal fluid) which contain secreted mature T1R-like ligand II, or tissue sources found to express T1R-like ligand II protein. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, Anal. Biochem. 162:156-159 (1987). Levels of mRNA encoding an T1R-like ligand II are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. T1R-like ligand II cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., Cell 49.357-367 (1987). To prepare probe DNA for use in S1 mapping, the sense strand of above-described eDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the T1R-like ligand II). Northern blot analysis can be performed as described above.

Preferably, levels of mRNA encoding the T1R-like ligand II are assayed using the RT-PCR method described in Makino et al., Technique 2.295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on apolyacrylamide gel. After drying the gel, the radioactivity of the appropriate bands (corresponding to the mRNA encoding the T1R-like ligand II) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying T1R-like ligand II levels in a biological sample can occur using any art-known method. Preferred for assaying T1R-like ligand II levels in a biological sample are antibody-based techniques. For example, T1R-like ligand II expression in tissues can be studied with classical immuno-histological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of T1R-like ligand II for Western-blot or dot/slot assay (Jalkanen, M., et al., *J. Cell. Biol* 101:976-985 (1985); Jalkanen, M., et al., *J. Cell. Biol.* 105:3087-3096 (1987)). In this technique, which is based on the use of cationic solid phases, quantitation of T1R-like ligand II can be accomplished using isolated T1R-like ligand II as a standard. This technique can also be applied to body fluids. With these samples, a molar concentration of T1R-like ligand II will aid to set standard values of T1R-like ligand II content for different body fluids, like serum, plasma, urine, synovial fluid, spinal fluid, etc. The normal appearance of T1R-like ligand II amounts can then be set using values from healthy individuals, which can be compared to those obtained from a test subject.

Other antibody-based methods useful for detecting T1R-like ligand II levels include immunoassays, such as the enzyme linked immunosorbent assay (ELISA) and the radio-immunoassay (RIA). For example, T1R-like ligand II-specific monoclonal antibodies can be used both as an immunoadsorbent and as an enzyme-labeled probe to detect and quantify the T1R-like ligand II. The amount of T1R-like ligand IL present in the sample can be calculated by reference to the amount present in a standard preparation using a linear regression computer algorithm. Such an ELISA for detecting a tumor antigen is described in Iacobelli et al., *Breast Cancer Research and Treatment* 11:19-30 (1988). In another ELISA assay, two distinct specific monoclonal antibodies can be used to detect T1R-like ligand II in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting T1R-like ligand II with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying T1R-like ligand II levels in a biological sample obtained from an individual, T1R-like ligand II can also be detected in vivo by imaging. Antibody labels or markers for in vivo imaging of T1R-like ligand II include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A T1R-like ligand II-specific antibody or antibody fragment which has been labeled with an appropriate detectable imaging moiety, such as a radioisotope (for example, $^{113}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain T1R-like ligand II. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer,* Burchiel, S. W. and Rhodes, B. A. eds., Masson Publishing Inc., (1982)).

T1R-like ligand II specific antibodies for use in the present invention can be raised against the intact T1R-like ligand II or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to T1R-like ligand II. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these portions are preferred.

The antibodies of the present invention may be prepared by any of a variety of methods. For example, cells expressing the T1R-like ligand II or an antigenic fragment thereof can be administered to an animal in order to induce the production of sera containing polyclonal antibodies. In a preferred method, a preparation of T1R-like ligand II protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or T1R-like ligand II binding fragments thereof). Such monoclonal antibodies can be prepared using hybridoma technology (Colligan, *Current Protocols in Immunology,* Wiley Interscience, New York (1990-1996); Harlow & Lane, Antibodies: A Laboratory Manual, Cold Spring Harbor Press, Cold Spring Harbor, N.Y. (1988), Chapters 6-9, *Current Protocols in Molecular Biology,* Ausubel, infra, Chapter 11, entirely incorporated herein by reference). In general, such procedures involve immunizing an animal (preferably a mouse) with an T1R-like ligand II antigen or, more preferably, with an T1R-like ligand II-expressing cell. Suitable cells can be recognized by their capacity to bind anti-T1R-like ligand II antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection (ATCC) (Rockville, Md., USA). After fusion, the resulting hybridoma cells are selectively maintained in HAT medium, and then cloned by limiting dilution as described by Wands et al., *Gastroenterology* 80:225-232 (1981); Harlow & Lane, infra, Chapter 7. The hybridoma cells obtained through such a selection are then assayed to identify clones which secrete antibodies capable of binding the T1R-like ligand II antigen.

Alternatively, additional antibodies capable of binding to the T1R-like gligand II antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, T1R-like ligand II specific antibodies are used to immunize an animal, preferably a mouse. The splenocytes of such an animal are then used to produce hybridoma cells, and the hybridoma cells are screened to identify clones which produce an antibody whose ability to bind to the T1R-like ligand II-specific antibody can be blocked by the T1R-like ligand II antigen. Such antibodies comprise anti-idiotypic antibodies to the T1R-like ligand II-specific antibody and can be used to immunize an animal to induce formation of further T1R-like ligand I-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, T1R-like ligand II-binding fragments can be produced through the application of recombinant DNA technology or through synthetic chemistry.

Where in vivo imaging is used to detect enhanced levels of T1R-like ligand II for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229.1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the T1R-like ligand II-specific antibodies of the present invention are provided herein. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{52}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{62}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al (*Clin. Chim. Acta* 70:1-31 (1976)), and Schurs et al. (*Clin. Chim. Acta* 81:1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an T1R-like ligand II gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Pharmaceutical Compositions and Therapeutic Administration

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, orpH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used to deliver the compositions of the invention (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

T1R-like ligand II compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919; EP 58,481), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, Science 249:1527-1533 (1990); Treat et al., in Liposomes in the Therapy of Infectious Disease and Cancer, Lopez-Berestein and Fidler (eds.), Liss, New York, pp. 317 - 327 and 353-365 (1989)). Liposomes containing T1R-like ligand II polypeptide may be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal T1R-like ligand II polypeptide therapy.

In a specific embodiment where the compound of the invention is a nucleic acid encoding a polypeptide, antibody, antagonist, agonist, protein, or fragment or variant thereof, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), by direct injection, by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

T1R-like ligand II polynucleotide, polypeptide, antibody, antagonist, agonist, or fragment or variant thereof of the invention may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or supposititorial solid pharmaceutical formulations, decanting or topical applications during surgery, aerosol delivery. Such methods are known in the art. T1R-like ligand II molecules of the invention may be administered as part of a pharmaceutical composition, described in more detail herein. Methods of delivering T1R-like ligand II molecules of the invention are known in the art and described in more detail herein.

The pharmaceutical compositions of the present invention may be administered, for example, by the parenteral, subcutaneous, intravenous, intramuscular, intraperitoneal, transdermal, or buccal routes. Alternatively, or concurrently, administration may be oral. The dosage administered will be dependent upon the age, health, and weight of the recipient, kind of concurrent treatment, if any, frequency of treatment, and the nature of the effect desired.

Compositions within the scope of this invention include all compositions wherein a T1R-like ligand II polynucleotide, polypeptide, antibody, agonist, antagonist or variant or fragment thereof is contained in an amount effective to achieve its intended purpose. While individual needs vary, determination of optimal ranges of effective amounts of each component is within the skill of the art. The effective dose is a function of the individual T1R-like ligand II polynucleotide, polypeptide, antibody, agonist, antagonist or fragment or variant thereof, the presence and nature of a conjugated therapeutic agent (see herein), the patient and his clinical status, and can vary from about 10 ng/kg body weight to about 100 mg/kg body weight. The preferred dosages comprise 0.1 to 10 mg/kg body wt.

Preparations of a T1R-like ligand II polynucleotide, polypeptide, antibody, agonist, antagonist or fragment or variant thereof, for parenteral administration, such as in detectably labeled form for imaging or in a free or conjugated form for therapy, include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. See, generally, *Remington's Pharmaceutical Science,* 16th ed., Mack Publishing Co., Easton, Pa., 1980.

As a general proposition, the total pharmaceutically effective amount of a T1R-like ligand II administered parenterally per dose will be in the range of about 0.01 ng/kg/day to 10 µg/kg/day of patient body weight, although, as noted above, this will be subject to therapeutic discretion. More preferably, this dose is at least 1.0 ng/kg/day, and most preferably for humans between about 1.0 to 100 ng/kg/day. If given continuously, the T1R-like ligand II is typically administered at a dose rate of about 0.01 ng/kg/hour to about 100 ng/kg/hour, either by 1-4 injections per day or by continuous subcutaneous infusions, for example, using a mini-pump. An intravenous bag solution may also be employed.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

A course of T1R-like ligand II polypeptide treatment to affect the immune system appears to be optimal if continued longer than a certain minimum number of days, 7 days in the case of the mice. The length of treatment needed to observe changes and the interval following treatment for responses to occur appears to vary depending on the desired effect.

For parenteral administration, in one embodiment, the T1R-like ligand II polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

The term "parenteral" as used herein refers to modes of administration which include intravenous, intramuscular, intraperitoneal intrasternal, subcutaneous and intraarticular injection and infusion.

Generally, the formulations are prepared by contacting the T1R-like ligand II polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The T1R-like ligand II is typically formulated in such vehicles at a concentration of about 0.001 ng/ml to 500 ng/ml, preferably 0.1-10 ng/ml, at a pH of about 3 to 8. It will be understood that the use of certain of the foregoing excipients, carriers, or stabilizers will result in the formation of T1R-like ligand II salts.

T1R-like ligand II to be used for therapeutic administration must be sterile. Sterility is readily accomplished by filtration through sterile filtration membranes (e.g., 0.2 micron membranes). Therapeutic T1R-like ligand II compositions generally are placed into a container having a sterile access port, for example, an intravenous solution bag or vial having a stopper pierceable by a hypodermic injection needle.

T1R-like ligand II ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous T1R-like ligand II solution, and the resulting mixture is lyophilized. The infusion solution is prepared by reconstituting the lyophilized T1R-like ligand II using bacteriostatic Water-for-Injection.

For example, satisfactory results are obtained by oral administration of a polypeptide having T1R-like ligand II activity in dosages on the order of from 0.05 to 5000 ng/kg/day, preferably 0.1 to 1000 ng/kg/day, more preferably 10 to 100 ng/kg/day, administered once or, in divided doses, 1 to 4 times per day. On administration parenterally, for example by i.v. drip or infusion, dosages on the order of from 0.01 to 500 ng/kg/day, preferably 0.05 to 100 ng/kg/day and more preferably 0.1 to 50 ng/kg/day can be used. Suitable daily dosages for patients are thus on the order of from 2.5 ng to 250 $\mu$g p.o., preferably 5 ng to 50 $\mu$g p.o., more preferably 50 ng to 12.5 $\mu$g p.o., or on the order of from 0.5 ng to 25 $\mu$g i.v., preferably 2.5 ng to 500 $\mu$g i.v. and more preferably 5 ng to 2.5 $\mu$g i.v.

The compositions of the invention may be administered alone or in combination with other therapeutic agents. Therapeutic agents that may be administered in combination with the compositions of the invention, include but not limited to, other members of the IL-1, IL-1R or T1R-like ligand II family, chemotherapeutic agents, antivirals, antibiotics, steroidal and non-steroidal anti-inflammatories, conventional immunotherapeutic agents, cytokines, chemokines and/or growth facotrs. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the compositions of the invention with compounds generally used to treat a plastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243-248 (1981); Kurtz, FEBS Letters, 14a:105-108 (1982); McGonigle et al., Kidney Int., 25:437-444 (1984); and Pavlovic-Kantera, Expt. Hematol., 8(supp. 8) 283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erytbrogenins, See for e.g., Dunn, "Current Concepts in Erythropoiesis", John Wiley and Sons (Chichester, England, 1983); Kalmani, Kidney Int., 22:383-391 (1982); Shahidi, New Eng. J. Med., 289:72-80 (1973); Urabe et al., J. Exp. Med., 149:1314-1325 (1979); Billat et al., Expt. Hematol., 10:133-140 (1982); Naughton et al., Acta Haemat, 69:171-179 (1983); Cognote et al. in abstract 364, Proceedings 7th Intl. Cong. of Endocrinology (Quebec City, Quebec, Jul. 1-7, 1984); and Rothman et al., 1982, J. Surg. Oncol., 20:105-108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{,2}$, folic acid and/or adrenocortical steroids.

In additional prefered embodiments, the compositions of the invention are administered in combination with hematopoietic growth factors. Hematopoietic growth factors that may be administered with the compositions of the invention included, but are not limited to LEUKINE (SARGRAMOSTIM™) and NEUPOGEN (FILGRASTIM™).

In one embodiment, the compositions of the invention are administered in combination with other members of the IL1- and IL1R-like family. Molecules that may be administered with the compositions of the invention include, but are not limited to, IL-1α, IL-1β, IL-1R and IL1-Ra.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, parany line, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15 anti-CD40, CD40L, IFN-gamma and TNF-alpha.

In one embodiment, the compositions of the invention are administered in combination with one or more chemokines. In specific embodiments, the compositions of the invention are administered in combination with an α(CxC) chemokine or nucleic acid encoding an α chemokine selected from the group consisting of γ interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or β(CC) chemokine or nucleic acid encoding a β chemokine selected from the group consisting of: RANTES (regulated on activation, normal T expressed and secreted), macrophage inflammatory protein-1α (MIP-1α), macrophage inflammatory protein-1β (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1γ (MIP-1γ), macrophage inflammatory protein-3α (MIP-3 α), macrophage inflammatory protein-3β (MIP-3β), macrophage inflammatory protein-4 (MIP-4/DC-CK-1/PARC), eotaxin, Exodus, and I-309; and/or the γ(C) chemokine, or nucleic acid encoding the γ chemokine, lymphotactin.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682 110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the compositions of the invention may be administered alone or in combination with other therapeutic regimens, including but not limited to, radiation therapy. Such combinatorial therapy may be administered sequentially and/or concomitantly.

Diagnostic Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell . Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, MO).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Treatment of T1R-like Ligand II Disorders

The invention provides methods of treatment, inhibition and prophylaxis by administration to a subject of an effective amount of a compound or pharmaceutical composition of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

It is believed by the present inventors that T1R-like ligand II polypeptides of the present invention share biological activities with interleukin-1 (IL-1) and the T1R ligand. Thus, the T1R-like ligand II polypeptide, antibody, antagonist, agonist, protein, or fragment or variant thereof, can be exogenously added to cells, tissues, or the body of an individual to produce a therapeutic effect. In particular, disorders caused by a decrease in the standard level of T1R-like ligand II protein activity can be treated by administering an effective amount of a T1R-like ligand II polypeptide or agonist of the invention. Preferably, a pharmaceutical composition is administered comprising an amount of an isolated T1R-like ligand II polypeptide or agonist of the invention effective to increase the T1R-like ligand II protein activity. Disorders where such a therapy would likely be effective are discussed above and herein.

As shown below in Example 18, T1R-like ligand II stimulates proliferation of CD34+ cells. Thus, it is expected that T1R-like ligand II will stimulate other hematopoietic stem cells and cells originating from hematopoietic stem cells.

A hematopoietic stem cell is a developmentally multipotent stem cell found in hematopoietic, or blood-forming tissue. It has the potential to mature into a mature blood cell through synergism between lineage-specific and multilineage growth factors. Tissues containing hematopoietic cells are found in various body locations including for example, bone marrow, spleen, and thymus. In the process of hematopoiesis, distinct populations of progenitor cells arise from more primitive, undifferentiated stem cells. Subsequent developmental eventually results in differentiation of mature classes of blood cells (for example, granulocytes, monocytes, eosinophils, megakaryocytes, and mast cells) from progenitor cells.

One of ordinary skill will appreciate that effective amounts of a T1R-like ligand II polynucleotide, polypeptide, antibody, antagonist, agonist, or fragment or variant thereof can be determined empirically for each condition where administration of a such is indicated. The polypeptide having T1R-like ligand II activity or antibody, agonist, antagonist, or fragment or variant thereof modulating such activity, can be administered in pharmaceutical compositions in combination with one or more pharmaceutically acceptable carriers, diluents and/or excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

The T1R-like ligand II composition to be used in the therapy will also be formulated and dosed in a fashion consistent with good medical practice, taking into account the clinical condition of the individual patient (especially the side effects of treatment with T1R-like ligand II alone), the site of delivery of the T1R-like ligand II composition, the method of administration, the scheduling of administration, and other factors known to practitioners. An "effective amount" of a T1R-like ligand II polypeptide for purposes herein is thus determined by such considerations. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

T1R-Like ligand II polynucleotides and polypeptides of the invention may be used in developing treatments for any disorder mediated (directly or indirectly) by defective, or insufficient amounts of T1R-Like ligand II. T1R-like ligand II polypeptides may be administered to a patient (e.g., mammal, preferably human) afflicted with such a disorder. Alternatively, a gene therapy approach may be applied to treat such disorders. Disclosure herein of T1R-like ligand II nucleotide sequences permits the detection of defective T1R-like ligand II genes, and the replacement thereof with normal T1R-like ligand II encoding genes. Defective genes may be detected in in vitro diagnostic assays, and by comparison of the T1R-Like ligand II nucleotide sequence disclosed herein with that of a T1R-Like ligand II gene derived from a patient suspected of harboring a defect in this gene.

In another embodiment, the polypeptides of the present invention are used as a research tool for studying the biological effects that result from inhibiting T1R-Like ligand II ligand interactions on different cell types. T1R-Like ligand II polypeptides also may be employed in in vitro assays for detecting T1R-like ligand II or T1R-like ligand II ligand or the interactions thereof.

T1R-like ligand II polynucleotides or polypeptides, or agonists or antagonists of T1R-like ligand II, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, T1R-like ligand II polynucleotides or polypeptides, or agonists or antagonists of T1R-Like ligand II, can be used as a marker or detector of a particular immune system disease or disorder. It is believed that T1R-like ligand II stimulates proliferation and/or differentiation of cells of hematopoietic origin, e.g. myeloid (platelets, red blood cells, neutrophils, and macrophages) and lymphoid (B and T lymphocytes) cells. As shown below, T1R-like ligand II polypeptides can be used to stimulate the proliferation of CD34+ cells.

By the invention, disorders caused by enhanced levels of T1R-like ligand II protein activity can be treated by administering an effective amount of an antagonist of a T1R-like ligand II polypeptide of the invention. Therefore, antibodies (preferably monoclonal) or antibody fragments that bind a T1R-like ligand II polypeptide of the present invention are useful in treating T1R-like ligand II-related disorders as are soluble T1R-like ligand II proteins, such as the extracellular domain, which competes with the intact protein for binding to the T1R-like ligand II receptor. Such antibodies and/or soluble T1R-like ligand II proteins are preferably provided in pharmaceutically acceptable compositions.

The antibodies described herein may be advantageously utilized in combination with other monoclonal or chimeric antibodies, or with lymphokines or hemopoietic growth factors, etc., which serve to increase the number or activity of effector cells which interact with the antibodies.

T1R-like ligand II polynucleotides or polypeptides, or agonists or antagonists of T1R-like ligand II, may be useful in treating or detecting deficiencies or disorders of hematopoietic cells. T1R-like Ligand II polynucleotides or polypeptides, or agonists or antagonists of T1R-Like Ligand II, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

In a specific embodiment, polynucleotides and/or polypeptides of the invention and/or angonists and/or antagonists thereof may be used to increase the concentration of blood cells in individuals in need of such increase (i.e., in hematopoietin therapy). Conditions that may be ameliorated by administering the compositions of the invention include, but are not limited to, neutropenia, anemia, and thrombocytopenia.

In a specific embodiment, the polynucleotides and/or polypeptides of the invention (and/or agonists or antagonists thereof) are used in erythropoietin therapy, which is directed toward supplementing the oxygen carrying capacity of blood. Polynucleotides and/or polypeptides of the invention (and/or agonists or antagonists thereof) may be used to treat or prevent diseases or conditions in patients generally requiring blood transfusions, such as, for example, trauma victims, surgical patients, dialysis patients, and patients with a variety of blood composition-affecting disorders, such as, for example, hemophilia, cystic fibrosis, pregnancy, menstrual disorders, early anemia of prematurity, spinal cord injury, aging, various neoplastic disease states, and the like. Examples of patient conditions that require supplementation of the oxygen carrying capacity of blood and which are within the scope of this invention, include, but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

As further described herein, the a polypeptide, polynucleotide, agonist, or antagonist of the present invention may be employed to stimulate growth and differentiation of hematopoietic cells and bone marrow cells either when used alone or when used in combination with other cytokines.

The polynucleotides and/or polypeptides of the invention and/or agonists and/or antagonists thereof, can also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

The polynucleotides and/or polypeptides of the invention and/or agonists and/or antagonists thereof, may also be employed for the expansion of immature hematopoeitic progenitor cells, for example, granulocytes, macrophages or monocytes, by temporarily preventing their differentiation. These bone marrow cells may be cultured in vitro. Thus, T1R-like ligand II polypeptides, polynucleotides, or agonists or antagonists thereof, may be useful as a modulator of hematopoietic stem cells in vitro for the purpose of bone marrow transplantation and/or gene therapy. Since stem cells are rare and are most useful for introducing genes into for gene therapy, T1R-Like ligand II can be used to isolate enriched populations of stem cells. Stem cells can be enriched by culturing cells in the presence of cytotoxins, such as 5-Fu, which kills rapidly dividing cells, where as the stem cells will be protected by T1R-Like Ligand II. These stem cells can be returned to a bone marrow transplant patient or can then be used for transfection of the desired gene for gene therapy. In addition, T1R-like ligand II can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

T1R-like ligand II also may have a role in vesicle trafficking, and thus may be associated with disorders of abnormal vesicle trafficking, including endocrine, secretory, inflammatory, and gastrointestinal disorders, and in the development of cancers, particularly those involving secretory and gastrointestinal tissues.

Therefore, in one embodiment, T1R-like ligand II polynucleotides, polypeptides, antibodies, agonists, antagonists and/or fragments or variants thereof may be administered to a subject to treat disorders associated with abnormal vesicle trafficking. Such disorders may include, but are not limited to, glucose-galactose malabsorption syndrome, hypercholesterolemia, diabetes insipidus, hyper- and hypoglycemia, goiter, Cushing's disease; gastrointestinal disorders including ulcerative colitis, gastric and duodenal ulcers; and other conditions associated with abnormal vesicle trafficking including allergies including hay fever; osteoarthritis; and Chediak-Higashi syndrome.

Cancer cells secrete excessive amounts of hormones or other biologically active peptides. Therefore, in another embodiment, polynucleotides, polypeptides, antibodies, agonists, antagonists and/or fragments or variants thereof of T1R-like ligand II may be administered to a subject to treat or prevent cancer, including, but not limited to, cancers of glands, tissues, and organs involved in secretion or absorption, including prostate, pancreas, lung, tongue, brain, breast, bladder, adrenal gland, thyroid, liver, uterus, kidney, testes, and organs of the gastrointestinal tract including small intestine, colon, rectum, and stomach. In particular, antibodies which are specific for T1R-like ligand II may be used directly as an antagonist, or indirectly as a targeting or delivery mechanism for bringing a pharmaceutical agent to cells or tissue which express T1R-like ligand II.

Additional preferred embodiments of the invention include, but are not limited to, the use of T1R-like ligand II polynucleotides, polypeptides, and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g. IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen. In a specific embodiment, the vaccine adjuvant is a polypeptide described herein. In another specific embodiment, the vaccine adjuvant is a polynucleotide described herein (i.e., the polynucleotide is a genetic vaccine adjuvant). As discussed herein, polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B streptococcus, Shigella spp., Enterotoxigenic *Escherichia coli*, Enterohemorrhagic *E. coli, Borrelia burgdorferi*, and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among immunodeficient individuals. B cell immunodeficiencies that may be ameliorated or treated by administering the polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency. In a specific embodiment, polypeptides or polynucleotides of the invention, or agonists thereof, is administered to treat or ameliorate selective IgA deficiency. In another specific embodiment, polypeptides or polynucleotides of the invention, or agonists thereof, is administered to treat or ameliorate ataxia-telangiectasia. In another specific embodiment, polyppltides or polynucleotides of the invention, or agonists thereof, is administered to treat or ameliorate common variable immunodeficiency. In another specific embodiment, polypeptides or polynucleotides of the invention, or agonists thereof, is administered to treat or ameliorate X-linked agammaglobulinemia. In another specific embodiment, polypeptides or polynucleotides of the invention, or agonists thereof, is administered to treat or ameliorate severe combined immunodeficiency (SCID). In another specific embodiment, polypeptides or polynucleotides of the invention, or agonists thereof, is administered to treat or ameliorate Wiskott-Aldrich syndrome. In another specific embodiment, polypeptides or polynucleotides of the invention, or agonists thereof, is administered to treat or ameliorate severe combined immunodeficiency (SCID). In another specific embodiment, polypeptides or polynucleotides of the invention, or agonists thereof, is administered to treat or ameliorate X-linked Ig deficiency with hyper IgM. T cell immunodeficiencies that may be ameliorated or treated by administering the polypeptides or polynucleotides of the invention, or agonists thereof, include, but are not limited to, DiGeorge anomaly (thymic hypoplasia), chronic mucocutaneous candidiasis, natural killer cell deficiency, idiopathic CD4+ T-lymphocytopenia, immunodeficiency with predominant T-cell defect, and unspecified ummunodeficiency of cell mediated immunity. Phagocyte disorder related immunodeficiencies that may be ameliorated or treated by administering the polypeptides or polynucleotides of the invention, or agonists thereof, include, but are not limited to, Hyperimmunoglobulinemia E syndrome (HIE), leukocyte adhesion defect type 1, chronic granulomatous disease, neutrophil G6PD deficiency, Chediak-Higashi syndrome, splenic deficiency syndromes, and myeloperoxidase deficiency. Complement disorder related immunodeficiencies that may be ameliorated or treated by administering the polypeptides or polynucleotides o the invention, or agonists thereof, include, but are not limited to, 1q deficiency, C1-C9 deficiencies, and C2 deficiencies.

As an agent to boost immunoresponsiveness among individuals having an acquired loss of B cell and/or T cell function. Conditions resulting in an acquired loss of B cell function that may be ameliorated or treated by administering the polypeptides or polynucleotides of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, T cells and/or B-cells. In one embodiment, polypeptides (in soluble, membrane-bound or transmembrane forms) or polynucleotides enhance antigen presentation or antagonize antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As B cell, monocytic cell, and/or T cell specific binding protein to which specific activators or inhibitors of cell growth may be attached. The result would be to focus the activity of such activators or inhibitors onto normal, diseased, or neoplastic cell populations.

As a stimulator of B cell production in pathologies such as AIDS, chronic lymphocyte disorder and/or Common Variable Immunodificiency;

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance T1R-like ligand II mediated responses.

As a means of activating monocytes/macrophages to defend against parasitic diseases that effect monocytes such as Leshmania.

As pretreatment of bone marrow samples prior to transplant. Such treatment would increase B cell and/or T cell representation and thus accelerate recovery.

As a means of regulating secreted cytokines that are elicited by T1R-like ligand II.

As a means to modulate IgE concentrations in vitro or in vivo. Additionally, T1R-like ligand II polypeptides or polynucleotides of the invention, or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of T1R-like ligand II include binding and/or inhibitory antibodies, antisense nucleic acids, ribozymes or soluble forms of the T1R-like ligand II receptor(s). These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the B cell proliferation and/or Ig secretion associated with autoimmune diseases such as idiopathic thrombocytopenic purpura, systemic lupus erythramatosus and MS.

An inhibitor of graft versus host disease or transplant rejection.

A therapy for B cell T cell and/or monocyitic malignancies, such as, for example, ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

T1R-like ligand II polypeptides or polynucleotides of the invention, or antagonists may be used to modulate IgE concentrations in vitro or in vivo. In another embodiment, administration of polypeptides or polynucleotides of the invention, or antagonists thereof, may be used to treat or prevent IgE-mediated allergic reactions including, but not limited to, asthma, rhinitis, and eczema.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described above.

The antagonists may be employed for instance to inhibit the chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hypereosinophilic syndrome by preventing eosinophil production and migration. Endotoxic shock may also be treated by the antagonists by preventing the migration of macrophages and their production of the polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatry arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by. The antagonists may also be employed to treat cases of bone marrow failure, for example, a plastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung. The antagonists may also be employed to treat lymphomas (e.g., one or more of the extensive, but not limiting, list of lymphomas provided herein).

Moreover, T1R-like Ligand II polynucleotides or polypeptides, or agonists or antagonists of T1R-like Ligand II, can also be used to modulate hemostatic (the stopping of bleeding) or thrombolytic activity (clot formation). For example, by increasing hemostatic or thrombolytic activity, T1R-Like Ligand II polynucleotides or polypeptides, or agonists or antagonists of T1R-Like Ligand II, could be used to treat blood coagulation disorders (e.g., afibrinogenemia, factor deficiencies), blood platelet disorders (e.g. thrombocytopenia), or wounds resulting from trauma, surgery, or other causes. Alternatively, T1R-like Ligand II polynucleotides or polypeptides, or agonists or antagonists of T1R-Like Ligand II, that can decrease hemostatic or thrombolytic activity could be used to inhibit or dissolve clotting. These molecules could be important in the treatment of heart attacks (infarction), strokes, or scarring.

T1R-like Ligand II polynucleotides or polypeptides, or agonists or antagonists of T1R-like Ligand II, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of T1R-like Ligand II polynucleotides or polypeptides, or agonists or antagonists of T1R-Like Ligand II, that can inhibit an immune response, particularly the proliferation, differentiation, or chemotaxis of T-cells, may be an effective therapy in treating or preventing autoimmune disorders or conditions associated with these disorders.

Examples of autoimmune disorders that can be treated, prevented or detected using compositions of the invention include, but are not limited, autoimmune diseases such as, for example, autoimmune hemolytic anemia, autoimmune neonatal thrombocytopenia, autoimmunocytopenia, hemolytic anemia, antiphospholipid syndrome, dermatitis, allergic encephalomyelitis, glomerulonephritis, Multiple Sclerosis, Neuritis, Ophthalmia, Polyendocrinopathies, Purpura, Reiter's Disease, Stiff-Man Syndrome, Autoimmune Pulmonary Inflammation, Guillain-Barre Syndrome, insulin dependent diabetes mellitis, and autoimmune inflammatory eye disease.

Additional autoimmune disorders that can be treated, prevented or detected using compositions of the invention include, but are not limited to, autoimmune thyroiditis (i.e., Hashimoto's thyroiditis) (often characterized, e.g., by cell-mediated and humoral thyroid cytotoxicity), systemic lupus erhthematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders that can be treated, prevented or detected using compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders that can be treated, prevented or detected using compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-T1R-like Ligand II.

Similarly, allergic reactions and conditions, such as asthma (particularly allergic asthma) or other respiratory problems, may also be treated by T1R-like Ligand II polynucleotides or polypeptides, or agonists or antagonists of T1R-Like Ligand II. Moreover, these molecules can be used to treat anaphylaxis, hypersensitivity to an antigenic molecule, or blood group incompatibility.

T1R-like Ligand II polynucleotides or polypeptides, or agonists or antagonists of T1R-Like Ligand II, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of T1R-like Ligand II polynucleotides or polypeptides, or agonists or antagonists of T1R-like Ligand II, that inhibits an immune response, particularly the proliferation, differentiation, or chemotaxis of T-cells, may be an effective therapy in preventing organ rejection or GVHD.

Similarly, T1R-Like Ligand II polynucleotides or polypeptides, or agonists or antagonists of T1R-Like Ligand II, may also be used to modulate inflammation. For example, T1R-Like Ligand II polynucleotides or polypeptides, or agonists or antagonists of T1R-Like Ligand II, may inhibit the proliferation and differentiation of cells involved in an inflammatory response. These molecules can be used to treat inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Diseases associated with increased cell proliferation, survival, or the inhibition of apoptosis that could be treated or detected by T1R-Like Ligand II polynucleotides or polypeptides, as well as antagonists or agonists of T1R-like Ligand II, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

Thus, in preferred embodiments T1R-like Ligand II polynucleotides or polypeptides of the invention, or agonists or antagonists thereof, are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment T1R-like Ligand II polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in preferred embodiments, T1R-Like Ligand II polynucleotides, polypeptides, and/or antagonists of the invention are used to inhibit growth, progression, and/or metasis of cancers, in particular those listed above, and in the paragraphs that follow.

Additional diseases or conditions associated with increased cell survival that may be treated or detected by T1R-Like Ligand II polynucleotides or polypeptides, or agonists or antagonists of T1R-like Ligand II, include, but are not limited to, progression, and/or metastases of malignancies and related disorders such as leukemia (including acute leukemias (e.g., acute lympsdhocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), and solid tumors including, but not limited to,, polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased cell death and/or decreased cell numbers that may be treated or detected by T1R-like Ligand II polynucleotides or polypeptides, or agonists or antagonists of T1R-Like Ligand II, include, but are not limited to, AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments T1R-like Ligand II polynucleotides or polypeptides of the invention are used to treat, prevent, and/or diagnose the diseases and disorders listed above and/or medical conditions associated with such disorders.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

T1R-like Ligand II polynucleotides or polypeptides, or agonists or antagonists thereof, can be used in the treatment of infectious agents. For example, by increasing the immune response, particularly increasing the proliferation and/or differentiation of B and/or T cells, infectious diseases may be treated. The immune response may be increased by either enhancing an existing immune response, or by initiating a new immune response. Alternatively, polynucleotides or polypeptides, or agonists or antagonists of, may also directly inhibit the infectious agent, without necessarily eliciting an immune response.

Viruses are one example of an infectious agent that can cause disease or symptoms that can be treated by polynucleotides or polypeptides, or agonists of T1R-like ligand II. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of, can be used to treat or detect any of these symptoms or diseases. In specific embodiments, T1R-like ligand II polynucleotides, polypeptides, or agonists are used to treat: meningitis, Dengue, EBV, and/or hepatitis (e.g., hepatitis B). In an additional specific embodiment T1R-like ligand II polynucleotides, polypeptides, or agonists are used to treat patients nonresponsive to one or more other commercially available hepatitis vaccines. In a further specific embodiment T1R-like ligand II polynucleotides, polypeptides, or agonists are used to treat AIDS.

Similarly, bacterial or fungal agents that can cause disease or symptoms and that can be treated by polynucleotides or polypeptides, or agonists or antagonists of, include, but not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., *Borrelia burgdorferi,* Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g. *Salmonella typhi,* and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerac,* Neisseriaceae (e.g., Acinetobacter, Gonorrhea, Menigococcal), *Meisseria meningitidis,* Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseaes, skin diseases (e.g., cellulitis, dermatocycoses), toxemia, urinary tract infections, wound infections, polynucleotides or polypeptides, or agonists or antagonists of, can be used to treat or detect any of these symptoms or diseases. In specific embodiments, T1R-like ligand II polynucleotides, polypeptides, or agonists thereof are used to treat: tetanus, Diptheria, botulism, and/or meningitis type B.

Moreover, parasitic agents causing disease or symptoms that can be treated by polynucleotides or polypeptides, or agonists of, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis, polynucleotides or polypeptides, or agonists or antagonists of, can be used to treat or detect any of these symptoms or diseases. In specific embodiments, T1R-like ligand II polynucleotides, polypeptides, or agonists thereof are used to treat malaria.

In another embodiment, the invention provides a method of delivering compositions containing the polypeptides of the invention (e.g., compositions containing polypeptides or anti-T1R-like ligand II antibodies associated with heterologous polypeptides, heterologous nucleic acids, toxins, or prodrugs) to targeted cells, such as, for example, cells expressing T1R-like Ligand II receptor, or cells expressing the cell surface bound form of T1R-like Ligand II. T1R-like Ligand II polypeptides or anti-T1R-like Ligand II antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., polypeptides or anti-T1R-like ligand II antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., T1R-like ligand II polypeptides or anti-T1R-like ligand II antibodies) in association with toxins or cytotoxic prodrugs.

In a specific embodiment, the invention provides a method for the specific destruction of cells of B cell lineage (e.g., B cell related leukemias or lymphomas) by administering anti-T1R-like ligand II antibodies and/or soluble T1R-like ligand II in association with toxins or cytotoxic prodrugs.

In a specific embodiment, the invention provides a method for the specific destruction of cells of T cell lineage (e.g., T cell related leukemias or lymphomas) by administering anti-T1R-like ligand II antibodies and/or soluble T1R-like ligand II in association with toxins or cytotoxic prodrugs.

In another specific embodiment, the invention provides a method for the specific destruction of cells of monocytic lineage (e.g., monocytic leukemias or lymphomas) by administering anti-T1R-like ligand II antibodies and/or soluble T1R-like ligand II in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

An additional condition, disease or symptom that can be treated by polynucleotides or polypeptides, or agonists of, is osteomyelitis.

Preferably, treatment using polynucleotides or polypeptides, or agonists of T1R-like ligand II, could either be by administering an effective amount of polypeptide to the patient, or by removing cells from the patient, supplying the cells with polynucleotide, and returning the engineered cells to the patient (ex vivo therapy). Moreover, as further discussed herein, the polypeptide or polynucleotide can be used as an adjuvant in a vaccine to raise an immune response against infectious disease.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

As an agent to direct an individuals immune system towards development of a humoral response (i.e. TH2) as opposed to a TH1 cellular response.

Expected Pleiotropic Biologic Effects of T1R-like Ligand II

The T1R-like ligand II polypeptides of the present invention are expected to have pleiotropic biological effects including many of those shown in Table 3 below. Similar biological effects have been shown for IL-1, particularly those associated with pancreatic endocrine tissue (Mandrup-Poulsen, T., et al., *Cytokine* 5:185 (1993)), thyroid glands (Rasmussen, A. K., Autoimmunity 16:141 (1993)), hypothalamic-pituitary-adrenal axis (Fantuzzi, G., & Ghezzi, P., *Mediator Inflamm.* 2:263 (1993); Rivier, C., *Ann. NY Acad. Sci.* 697:97 (1993); Rivier, C., & Rivest, S., *Ciba. Found. Symp.* 172:204 (1993)), fever (Coceani, F., "Fever: Basic Mechanisms and Management", New York, N.Y., Raven (1991) p. 59), bone metabolism (Tatakis, D. N., *J. Peridontol* 64:416 (1993)), destruction of cartilage in the pathogenesis of rheumatoid arthritis (Arend, W. P., & Dayer, J. M., *Arthritis Rheum* 33:305 (1990); Krane, S. M., et al., *Ann. NY Acad. Sci.* 580:340 (1990)), uterine implantation (Lewis, M. sP., et al., *Placenta* 15: 13 (1994)), and loss of lean body mass (Roubenoff, R., et al., *J. Clin. Invest.* 93:2379 (1994)).

TABLE 3

POSSIBLE BIOLOGIC EFFECTS OF T1R-LIKE LIGAND II

Effects of systemically injected T1R-like ligand II

Fever; increased slow wave sleep; social depression; anorexia
Hypotension; myocardial suppression; tachycardia; lactic acidosis
Increased circulating nitric oxide; hypoaminoacidemia
Hyperinsulinemia; hyperglycemia; hypoglycemia
Stimulation of hypothalamic-pituitary-adrenal axis
Release of hypothalamic monoamines and neuropeptides
Neutrophilia; increased marrow cellularity; increased platelets
Increased hepatic acute phase protein synthesis
Hypoferremia; hypozincemia; increased sodium excretion
Hyperlipidemia; increased muscle protein breakdown
Hypoalbuminemia; decreased drug metabolism
Increased metastases
Increased nonspecific resistance to infection (pretreatment)
Learning defects in offspring after maternal IL-1 treatment Effects of locally injected T1R-like ligand II Infiltration of neutrophils into rabbits knee joint
Increased proteoglycan breakdown in rabbit knee joint
Induction of uveitis following intravitreal injection
Angiogenesis in anterior chamber of eye
Cellular infiltrate and cytokine induction in cerebral ventricles
Neutrophil and albumin influx into lungs after intratracheal instillation Changes in immunologic responses Increased antibody production (adjuvant effect)
Increased lymphokine synthesis (IL-2, -3, -4, -5, -6, -7, -10 and -12)
Increased IL-2 (β) receptor
Development of type 2 human T-cell clones
Inhibition of tolerance to protein antigens
Enhancement of spleen cell mitogenic response to LPS Effects of T1R-like ligand II on cultured cells or tissues Increased expression of ELAM-1, VCAM-1, ICAM-1
Cytotoxicity (apoptosis) of insulin-producing islet β cells
Inhibition of thyroglobulin synthesis in thyrocytes
Cartilage breakdown, release of calcium from bone
Increased release of arachidonic acid, prostanoids, and eicosanoids
Increased mucus production and chloride flux in intestinal cells
Enhancement in chloride flux (GABAA receptor) in brain synaptosomes
Proliferation of fibroblasts, smooth muscle cells, messangial cells
Growth inhibition of hair follicles
Increased corticosterone synthesis by adrenals Assays used: pancreatic endocrine tissue (Mandrup-Poulsen, T., et al, Cytokine 5:185 (1993)), thyroid gland (Rasmussen, A. K., Autoimmunity 16:141 (1993)), hypothalamic-pituitary-adrenal axis (Fantuzzi, G., & Ghezzi, P., Mediator Inflamm. 2:263 (1993); Rivier, C., Ann. NY Acad. Sci. 697:97 (1993); Rivier, C., & Rivest, S., Ciba. Found Symp 172:204 (1993)), fever (Coceani, F., "Fever: Basic Mechanisms and Management", New York, NY, Raven (1991) p. 59), bone metabolism (Tatakis, D.N., J. Pendontol 64:416 (1993)), destruction of cartilage in the pathogenesis of rheumatoid arthritis (Arend, W.P., & Dayer, J.M., Arthritis Rheum 33:305 (1990); Krane, S.M., et al., Ann. NY Acad. Sci., 580:340 (1990)), uterine implantation (Lewis, M.P., et al., Placenta 15:13 (1994)), and loss of lean body mass (Roubenoff, R., et al., J. Clin. Invest. 93:2379 (1994).

Having generally described the invention, the same will be more readily understood by reference to the following examples, which are provided by way of illustration and are not intended as limiting.

EXAMPLES

Example 1

Expression and Purification of T1R-like ligand II in *E. coli*

The DNA sequence encoding the mature, extracellular soluble portion of T1R-like ligand II in the deposited cDNA clone is amplified using PCR oligonucleotide primers specific to the amino terminal sequences of the T1R-like ligand II and to vector sequences 3' to the gene. Additional nucleotides containing restriction sites to facilitate cloning are added to the 5' and 3' sequences respectively.

One of ordinary skill in the art will understand that the full-length, mature T1R-like ligand II protein (amino acid about 1 to about 203 in SEQ ID NO:2) can be expressed in *E. coli* using suitable 5' and 3' oligonucleotide primers.

The cDNA sequence encoding the extracellular domain of the full length T1R-like ligand II in the deposited clone is amplified using PCR oligonucleotide primers corresponding to the 5' and 3' sequences of the gene. The 5' primer contains the sequence 5' CGC <u>CCA TGG</u> CCG GCT TCA CAC CTT CC 3' (SEQ ID NO:4) containing the underlined Nco I site and 17 nucleotides (nucleotides 131-147) of the T1R-like ligand II protein coding sequence in FIGS. 1A–1B (SEQ ID NO:1) beginning immediately after the signal peptide.

The 3' primer has the sequence 5' CGC <u>AAG CTT</u> TCA TCT ATC AAA GTT GCT TTC 3' (SEQ ID NO:5) containing a Hind III restriction site followed by a stop codon and 18 nucleotides reverse and complementary to nucleotides 619-636 of the T1R-like ligand II protein coding sequence in FIGS. 1A–1B (SEQ ID NO:1).

The restriction sites are convenient to restriction enzyme sites in the bacterial expression vector pQE60, which are used for bacterial expression in M15/rep4 host cells in these examples. (Qiagen, Inc., Chatsworth, Calif., 91311). pQE60 encodes ampicillin antibiotic resistance ("Amp<sup>r</sup>") and contains a bacterial origin of replication ("ori"), an IPTG inducible promoter, a ribosome binding site ("RBS"), a 6-His tag and restriction enzyme sites.

The amplified T1R-like ligand II DNA and the vector pQE60 both are digested with Nco I and Hind III and the digested DNAs are then ligated together. Insertion of the T1R-like ligand II DNA into the restricted pQE60 vector placed the T1R-like ligand II coding region downstream of and operably linked to the vector's IPTG-inducible promoter and in-frame with an initiating AUG appropriately positioned for translation of T1R-like ligand II.

The ligation mixture is transformed into competent *E. coli* cells using standard procedures. Such procedures are described in Sambrook et al., *Molecular Cloning: A Laboratory Manual,* 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan<sup>r</sup>"), is used in carrying out the illustrative example described here. This strain, which is only one of many that are suitable for expressing T1R-like ligand II, is available commercially from Qiagen.

Transformants are identified by their ability to grow on LB plates in the presence of ampicillin and kanamycin. Plasmid DNA is isolated from resistant colonies and the identity of the cloned DNA was confirmed by restriction analysis.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS.

Analysis of the preparation by standard methods of polyacrylamide gel electrophoresis reveals that the preparation contains about 95% monomer T1R-like ligand II having the expected molecular weight of approximately 26 kDa.

Example 2

Cloning and Expression of T1R-like ligand II in a Baculovirus Expression System

The cDNA sequence encoding the full length T1R-like ligand II in the deposited clone is amplified using PCR oligonucleotide primers corresponding to the 5' and 3' sequences of the gene:

The 5' primer has the sequence 5' CGC <u>GGA TCC</u> GCC ATC ATG GGC GAC AAG ATC TGG 3' (SEQ ID NO:6) containing the underlined BamHI restriction enzyme site followed by 18 nucleotides (nucleotides 55 to 72) of the sequence of the T1R-like ligand II protein in FIGS. 1A–1B (SEQ ID NO:1). Inserted into an expression vector, as described herein, the 5' end of the amplified fragment encoding T1R-like ligand II provides an efficient signal peptide. An efficient signal for initiation of translation in eukaryotic cells, as described by Kozak, M., *J. Mol. Biol.* 196: 947-950 (1987) is appropriately located in the vector portion of the construct.

The 3' primer has the sequence 5' CGC <u>GGT ACC</u> TCA CAA TGT TAC GTA CTC TAG 3' (SEQ ID NO:7) containing the underlined Asp 718 restriction site followed by a stop codon and 18 nucleotides reverse and complementary to nucleotides 754-771 of the T1R-like ligand II coding sequence set out in FIGS. 1A–1B (SEQ ID NO:1).

The cDNA sequence encoding the extracellular domain of the full length T1R-like ligand II in the deposited clone is amplified using PCR oligonucleotide primers corresponding to the 5' and 3' sequences of the gene:

The 5' primer has the sequence 5' CGC <u>GGA TCC</u> GCC ATC ATG GGC GAC AAG ATC TGG 3' (SEQ ID NO:6) containing the underlined BamHI restriction enzyme site followed by 18 nucleotides (nucleotides 55-72) of the sequence encoding the T1R-like ligand II protein set out in FIGS. 1A–1B (SEQ ID NO:1). Inserted into an expression vector, as described herein, the 5' end of the amplified fragment encoding T1R-like ligand II provides an efficient signal peptide. An efficient signal for initiation of translation in eukaryotic cells, as described by Kozak, M., *J. Mol. Biol.* 196: 947-950 (1987) is appropriately located in the vector portion of the construct.

The 3' primer has the sequence 5' CGC <u>GGT ACC</u> TCA TCT ATC AAA GTT GCT TTC 3' (SEQ ID NO:8) containing the underlined Asp 718 restriction site followed by a stop codon and 18 nucleotides complementary and reverse to nucleotides 619-636 of the T1R-like ligand II coding sequence set out in FIGS. 1A–1B (SEQ ID NO:1).

The amplified fragment is isolated from a 1% agarose gel using a commercially available kit ("Geneclean," BIO 101 Inc., La Jolla, Calif.). The fragment then is digested with BamHI and Asp 718 and again is purified on a 1% agarose gel. This fragment is designated herein F2.

The vector pA2 is used to express the T1R-like ligand II full length and extracellular domains of an T1R-like ligand II in the baculovirus expression system, using standard methods, as described in Summers et al., *A Manual of Methods for Baculovirus Vectors and Insect Cell Culture Procedures,* Texas Agricultural Experimental Station Bulletin No. 1555 (1987). The pA2 vector does not contain a signal peptide coding region. Thus, the T1R-like ligand II signal peptide is relied upon (nucleotides 55-132 in SEQ ID NO:1; amino acids -26 to -1 SEQ ID NO:2).

If the T1R-like ligand II signal peptide does not result in efficient expression of the T1R-like ligand II protein, the pA2-GP vector may be used instead of the pA2 vector. The signal peptide of AcMNPV gp67, including the N-terminal methionine, is located just upstream of a BamHI site. One of ordinary skill in the art will understand that if the pA2-GP expression vector is used, the 5' oligonucleotide used should not contain sequence coding for the T1R-like ligand II signal peptide. Instead, the 5' oligonucleotide should begin at nucleotide 131.

Both the pA2 and pA2-GP expression vectors contain the strong polyhedrin promoter of the *Autographa californica* nuclear polyhedrosis virus (AcMNPV) followed by convenient restriction sites. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2 or pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31-39, among others.

The plasmid is digested with the restriction enzyme BamHI and Asp 718 and then is dephosphorylated using calf intestinal phosphatase, using routine procedures known in the art. The DNA is then isolated from a 1% agarose gel using a commercially available kit ("Geneclean" BIO 101 Inc., La Jolla, Ca.). This vector DNA is designated herein "V2".

Fragment F2 and the dephosphorylated plasmid V2 are ligated together with T4 DNA ligase. *E. coli* HB 101 cells are transformed with ligation mix and spread on culture plates. Bacteria are identified that contain the plasmid with the human T1R-like ligand II gene by digesting DNA from individual colonies using BamHI and Asp 718 and then analyzing the digestion product by gel electrophoresis. The sequence of the cloned fragment is confirmed by DNA sequencing. This plasmid is designated herein pBacT1R-like ligand II.

5 µg of the plasmid pBacT1 R-like ligand II is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413-7417 (1987). 1 µg of BaculoGold™ virus DNA and 5 µg of the plasmid pBacT1R-like ligand II are mixed in a sterile well of a microtiter plate containing 50 µl of serum-free Grace's medium (Life Technologies Inc., Gaithersburg, MD). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. Clones containing properly inserted T1R-like ligand II are identified by DNA analysis including restriction mapping and sequencing. This is designated herein as V-T1R-like ligand II.

Sf9 cells are grown in Grace's medium supplemented with 10% heat-inactivated FBS. The cells are infected with the recombinant baculovirus V-T1R-like ligand II at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in Mammalian Cells

Most of the vectors used for the transient expression of the T1R-like ligand II protein gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLV-I, HIV-I and the early promoter of the cytomegalovirus (CMV). However, cellular signals can also be used (e.g. human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkat cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277-279 (1991); Bebbington et al., Bio/Technology 10: 169-175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438-4470 (March, 1985)) plus a fragment of the CMV-enhancer (Boshart et al., Cell 41:521-530(1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

An expression plasmid is made by cloning a cDNA encoding T1R-like ligand II into the expression vector pcDNAI/Amp (which can be obtained from Invitrogen, Inc.).

The expression vector pcDNAI/amp contains: (Dower, Colotta, F., et al., *Immunol Today* 15:562 (1994)) an *E. coli* origin of replication effective for propagation in *E. coli* and other prokaryotic cells; (Greenfeder, S. A., et al., *J. Biol. Chem.* 270:13757 (1995)) an ampicillin resistance gene for selection of plasmid-containing prokaryotic cells; (Polan, M. L., et al., *Am. J. Obstet. Gynecol.* 170:1000 (1994)) an SV40 origin of replication for propagation in eukaryotic cells; (Carinci, Mora, M., et al., *Prog. Clin. Biol. Res.* 349:205 (1990)) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire T1R-like ligand II precursor and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows.

The T1R-like ligand II cDNA of the deposited clone is amplified using primers that contain convenient restriction sites, much as described above regarding the construction of expression vectors for expression of T1R-like ligand II in *E. coli*. To facilitate detection, purification and characterization of the expressed T1R-like ligand II, one of the primers contains a hemagglutinin tag ("HA tag") as described above.

One of ordinary skill in the art will understand that the full-length T1R-like ligand II protein (amino acid about −26 to about 203 in SEQ ID NO:2) can be expressed in COS cells using suitable 5' and 3' oligonucleotide primers.

The cDNA sequence encoding the extracellular domain of the full length T1R-like ligand II in the deposited clone is amplified using PCR oligonucleotide primers corresponding to the 5' and 3' sequences of the gene. The 5' primer has the following sequence:

5' CGC <u>GGA TCC</u> GCC ATC ATG GGC GAC AAG ATC TGG 3' (SEQ ID NO:6), containing the underlined BamHl site and 18 nucleotides (nucleotides 55 to 72) of the T1R-like ligand II coding sequence set out in FIGS. 1A–1B (SEQ ID NO:1).

The 3' primer has the following sequence:

5' CGC <u>TCT AGA</u> TCA AGC GTA GTC TGG GAC GTC GTA TGG GTA TCT ATC AAA GTT GCT TTC 3' (SEQ ID NO:9), containing the underlined Xba I restriction site, a stop codon, an HA tag, and 18 nucleotides reverse and complementary to nucleotides 619-639 of the TRI-like ligand II coding sequence set out in FIGS. 1A–1B (SEQ ID NO:1).

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037) and the transformed culture is plated on ampicillin media plates which then are incubated to allow growth of ampicillin resistant colonies. Plasmid DNA is isolated from resistant colonies and examined by restriction analysis and gel sizing for the presence of the T1R-like ligand II encoding fragment.

For expression of recombinant T1R-like ligand II, COS cells are transfected with an expression vector, as described above, using DEAE-DEXTRAN, as described, for instance, in Sambrook et al., Molecular Cloning: A Laboratory Manual, Cold Spring Laboratory Press, Cold Spring Harbor, N.Y. (1989). Cells are incubated under conditions for expression of T1R-like ligand II by the vector.

Expression of the T1R-like ligand II HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above.

Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of T1R-like ligand protein. Plasmid pC4 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for the expression of the gene of interest a strong promoter of the long terminal repeat (LTR) of the Rouse Sarcoma Virus (Cullen, et al., Molecular and Cellular biology, March 1985, 438-4470) plus a fragment isolated from the enhancer of the immediate early gene of human cytomegalovirus (CMV) (Boshart et al., *Cell* 41:521-530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other highly efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g. G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding T1R-like ligand II protein is amplified using PCR oligonucleotide primers specific to the amino terminal sequence of the T1R-like ligand II protein and to vector sequences 3' to the gene. Additional nucleotides containing restriction sites to facilitate cloning are added to the 5' and 3' sequences respectively.

The cDNA sequence encoding the full length T1R-like ligand II in the deposited clone is amplified using PCR oligonucleotide primers corresponding to the 5' and 3' sequences of the gene. The 5' primer has the sequence 5' CGC GGATCC GCC ATC ATG GGC GAC AAG ATC TGG 3' (SEQ ID NO:6), containing the underlined BamH I restriction enzyme site followed 18 nucleotides (nucleotides 55-72) of the sequence of T1R like ligand II in FIGS. 1A–1B (SEQ ID NO:1). Inserted into an expression vector, as described herein, the 5' end of the amplified fragment encoding T1R-like ligand II provides an efficient signal peptide. An efficient signal for initiation of translation in eukaryotic cells, as described by Kozak, M., *J. Mol. Biol.* 196: 947-950 (1987) is appropriately located in the vector portion of the construct.

The 3' primer has the sequence 5' GCG GGT ACC TCA CAA TGT TAC GTA CTC TAG 3' (SEQ ID NO: 7), containing the underlined Asp 718 restriction site followed by a stop codon and 18 nucleotides reverse and complementary to nucleotides 754 to 771 of the T1R-like ligand II coding sequence in FIGS. 1A–1B (SEQ ID NO:1). The restriction sites are convenient to restriction enzyme sites in the CHO expression vector PC-4.

The cDNA sequence encoding the extracellular domain of the full length T1R-like ligand II in the deposited clone is amplified using PCR oligonucleotide primers corresponding to the 5' and 3' sequences of the gene.

The 5' primer has the sequence 5' CGC GGA TCC GCC ATC ATG GGC GAC AAG ATC TGG 3' (SEQ ID NO:6) containing the underlined BamHI restriction enzyme site and 18 nucleotides (nucleotides 55 to 72) of the T1R-like ligand II coding sequence in FIGS. 1A–1B (SEQ ID NO:1). Inserted into an expression vector, as described herein, the 5' end of the amplified fragment encoding T1R-like ligand II provides an efficient signal peptide. An efficient signal for initiation of translation in eukaryotic cells, as described by Kozak, M., *J. Mol. Biol.* 196: 947-950 (1987) is appropriately located in the vector portion of the construct.

The 3' primer has the sequence 5' CGC GGT ACC TCA TCT ATC AAA GTT GCT TTC 3' (SEQ ID NO:8) containing the underlined Asp 718 restriction site followed by a stop codon and 18 nucleotides reverse and complementary to nucleotides 619-636 of the T1R-like ligand II coding sequence set out in FIGS. 1A–1B (SEQ ID NO: 1).

The amplified T1R-like ligand II protein DNA are digested with BamHI and Asp 718. The vector pC4 is digested with BamHI and the digested DNAs are then ligated together. The isolated fragment and the dephosphorylated vector are then ligated with T4 DNA ligase. Insertion of the T1R like ligand II protein DNA into the BamHI restricted vector places the T1R like ligand II protein coding region downstream of and operably linked to the vector's promoter. *E. coli* HB101 cells are then transformed and bacteria identified that contained the plasmid pC4 inserted in the correct orientation using the restriction enzyme BamHI. The ligation mixture is transformed into competent *E. coli* cells using standard procedures as described, for example, in Sambrook et al., MOLECULAR CLONING: A LABORATORY MANUAL, 2nd Ed.; Cold Spring Harbor Laboratory Press, Cold Spring Harbor, N.Y. (1989). The transformed culture is plated on ampicillin media plates which then are incubated to allow growth of ampicillin resistant colonies. Plasmid DNA is isolated from resistant colonies and examined by restriction analysis and gel sizing for the presence of the T1R-like ligand II-encoding fragment. The sequence of the inserted gene is confirmed by DNA sequencing.

Example 3(c)

Transfection of CHO-DHFR-cells

Chinese hamster ovary cells lacking an active DHFR enzyme are used for transfection. 5 µg of the expression plasmid C4 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE. Expression of the T1R-like ligand II fusion protein is detected by radiolabelling and immunoprecipitation, using methods described in, for example Harlow et al., *Antibodies. A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Tissue distribution of T1R-like Ligand II Gene Expression

Northern blot analysis is carried out to examine expression levels of the T1R-like ligand II gene in human tissues, using methods described by, among others, Sambrook et al., cited above. A cDNA probe containing the entire T1R-like ligand II nucleotide sequence (SEQ ID NO:1) is labeled with $^{32}$P using the rediprime™ DNA labelling system (Amersham Life Science), according to manufacturer's instructions. After labelling, the probe is purified using a CHROMA SPIN-100™ column (Clontech Laboratories, Inc.), according to manufacturer's protocol number PT1200-1. The purified labelled probe is then used to examine various human tissues for expression of the T1R-like ligand II gene.

Multiple Tissue Northern (MTN) blots containing various human tissues (H) and human immune system tissues (IM) are obtained from Clontech and are examined with labelled probe using ExpressHyb™ Hybridization Solution (Clontech) according to manufacturer's protocol number PT 1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby entirely incorporated by reference.

Example 5

Gene Therapy using Endogenous T1R-like Ligand II Gene

A method of gene therapy according to the present invention involves operably associating the endogenous T1R-like ligand II sequence with a promoter via homologous recombination as described, for example, in U.S. Pat. No. 5,641,670, issued June 24, 1997; International Publication Number WO 96/29411, published September 26,1996; International Publication Number WO 94/12650, published August 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous T1R-like ligand II, flanking the promoter. The targeting sequence will be sufficiently near the 5' end of T1R-like ligand II so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous T1R-like ligand II sequence. This results in the expression of T1R-like ligand II in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the T1R-like ligand II locus, plasmid pUC18 (MBI Fermentas, Amherst, N.Y.) is digested with HindIII. The CMV promoter is amplified by PCR with an XbaI site on the 5' end and a BamHI site on the 3'end. Two T1R-like ligand II non-coding sequences are amplified via PCR: one T1R-like ligand II non-coding sequence (T1R-like ligand II fragment 1) is amplified with a HindIII site at the 5' end and an Xba site at the 3'end; the other T1R-like ligand II non-coding sequence (T1R-like ligand II fragment 2) is amplified with a BamHI site at the 5'end and a HindIII site at the 3'end. The CMV promoter and T1R-like ligand II fragments are digested with the appropriate enzymes (CMV promoter—XbaI and BamHI; T1R-like ligand II fragment 1—XbaI; T1R-like ligand II fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5.×10$^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 11 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 6

Protein Fusions of T1R-Like Ligand II

T1R-like ligand II polypeptides of the invention are optionally fused to other proteins. These fusion proteins can be used for a variety of applications. For example, fusion of T1R-like ligand II polypeptides to His-tag, HA-tag, protein A, IgG domains, and maltose binding protein facilitates purification. (See EP A 394,827; Traunecker, et al., Nature 331:84-86 (1988).) Similarly, fusion to IgG-1, IgG-3, and albumin increases the halflife time in vivo. Nuclear localization signals fused to T1R-like Ligand II polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described herein. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and T1R-like ligand II polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region:

```
GGGATCCGGAGCCCAAATCTTCTGACAAAACTCACACATGCC    (SEQ ID NO: 26)

CACCGTGCCCAGCACCTGAATTCGAGGGTGCACCGTCAGTCTTCCTC

TTCCCCCCAAAACCCAAGGACACCCTCATGATCTCCCGGACTCCTGA

GGTCACATGCGTGGTGGTGGACGTAAGCCACGAAGACCCTGAGGTC

AAGTTCAACTGGTACGTGGACGGCGTGGAGGTGCATAATGCCAAGA

CAAAGCCGCGGGAGGAGCAGTACAACAGCACGTACCGTGTGGTCA

GCGTCCTCACCGTCCTGCACCAGGACTGGCTGAATGGCAAGGAGTA

CAAGTGCAAGGTCTCCAACAAAGCCCTCCCAACCCCCATCGAGAAA
```

```
                      -continued
ACCATCTCCAAAGCCAAAGGGCAGCCCCGAGAACCACAGGTGTACA

CCCTGCCCCCATCCCGGGATGAGCTGACCAAGAACCAGGTCAGCCT

GACCTGCCTGGTCAAAGGCTTCTATCCAAGCGACATCGCCGTGGAG

TGGGAGAGCAATGGGCAGCCGGAGAACAACTACAAGACCACGCCT

CCCGTGCTGGACTCCGACGGCTCCTTCTTCCTCTACAGCAAGCTCAC

CGTGGACAAGAGCAGGTGGCAGCAGGGGAACGTCTTCTCATGCTCC

GTGATGCATGAGGCTCTGCACAACCACTACACGCAGAAGAGCCTCT

CCCTGTCTCCGGGTAAATGAGTGCGACGGCCGCGACTCTAGAGGAT
```

Example 7

Isolation of Antibody Fragments Directed Against Polypeptides of the Present Invention from a Library of scFvs.

Naturally occurring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the Library:

A library of scFvs is constructed from the RNA of human PBLs as described in WO92/01047. To rescue phage displaying antibody fragments, approximately $10^9$ E. coli harbouring the phagemid are used to inoculate 50 ml of 2xTY containing 1% glucose and 100 μg/ml of ampicillin (2xTY-AMP-GLU) and grown to an O.D. of 0.8 with shaking. Five μl ml of this culture is used to innoculate 50 ml of 2xTY-AMP-GLU, $2\times10^8$ TU of delta gene 3 helper phage (M13 Δ gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2xTY containing 100 μg/ml ampicillin and 50 μg/ml kanamycin and grown overnight. Phage are prepared as described in WO92/01047.

M13Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C with shaking. Cells are pelleted (IEC-Centra 8, 4000 revs/min for 10 min), resuspended in 300 ml 2xTY broth containing 100 μg ampicillin/ml and 25 μg kanamycinl/ml (2xTY-AMP-KAN) and grown overnight, shaking at 37 C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately $10^{13}$ transducing units/ml (ampicillin-resistant clones).

Panning of the Library:

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders:

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 8

Production of an Antibody

Hybridoma Technology:

The antibodies of the present invention can be prepared by a variety of methods. (See, Current Protocols, Chapter 2.) As one example of such methods, cells expressing T1R-like ligand II polypeptide(s) are administered to an animal to induce the production of sera containing polyclonal antibodies. In a preferred method, a preparation of T1R-like ligand II polypeptide(s) is prepared and purified to render it substantially free of natural contaminants. Such a preparation is then introduced into an animal in order to produce polyclonal antisera of greater specific activity.

Monoclonal antibodies specific for T1R-like ligand II polypeptide(s) are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with T1R-like ligand II polypeptide(s) or, more preferably, with a secreted T1R-like ligand II polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the T1R-like ligand II polypeptide(s).

Alternatively, additional antibodies capable of binding to T1R-like ligand II polypeptide(s) can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the T1R-like ligand II protein-specific antibody can be blocked by T1R-like ligand II polypeptide(s). Such antibodies comprise anti-idiotypic antibodies to the T1R-like ligand II protein-specific antibody and are used to immunize an animal to induce formation of further T1R-like ligand II protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567. Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 9

Method of Determining Alterations in the T1R-like Ligand II Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of T1R-like Ligand II are also determined and genomic PCR products analyzed to confirm the results. PCR products harboring suspected mutations in T1R-Like Ligand II is then cloned and sequenced to validate the results of the direct sequencing.

PCR products of T1R-like Ligand II are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in T1R-like Ligand II not present in unaffected individuals.

Genomic rearrangements are also observed as a method of determining alterations in the T1R-like Ligand II gene. Genomic clones isolated using techniques known in the art are nick-translated with digoxigenindeoxy-uridine 5'-triphosphate (Boehringer Manheim), and FISH performed as described in Johnson, Cg. et al., Methods Cell Biol. 35:73-99 (1991). Hybridization with the labeled probe is carried out using a vast excess of human cot-I DNA for specific hybridization to the T1R-like Ligand II genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of T1R-like Ligand II (hybridized by the probe) are identified as insertions, deletions, and translocations. These T1R-like Ligand II alterations are used as a diagnostic marker for an associated disease.

Example 10

Method of Detecting Abnormal Levels of T1R-like Ligand II in a Biological Sample T1R-Like Ligand II polypeptides can be detected in a biological sample, and if an increased or decreased level of T1R-like Ligand II is detected, this polypeptide is a marker for a particular phenotype. Methods of detection are numerous, and thus, it is understood that one skilled in the art can modify the following assay to fit their particular needs.

For example, antibody-sandwich ELISAs are used to detect T1R-like Ligand II in a sample, preferably a biological sample. Wells of a microtiter plate are coated with specific antibodies to T1R-Like Ligand II at a final concentration of 0.2 to 10 µg/ml. The antibodies are either monoclonal or polyclonal and are produced using technique known in the art. The wells are blocked so that non-specific binding of T1R-like Ligand II to the well is reduced.

The coated wells are then incubated for >2 hours at RT with a sample containing T1R-Like Ligand II. Preferably, serial dilutions of the sample should be used to validate results. The plates are then washed three times with deionized or distilled water to remove unbounded T1R-like Ligand II.

Next, 50 µl of specific antibody-alkaline phosphatase conjugate, at a concentration of 25-400 ng, is added and incubated for 2 hours at room temperature. The plates are again washed three times with deionized or distilled water to remove unbounded conjugate.

75 μl of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is preparded using the experimental results from serial dilutions of a control sample with the sample concentration plotted on the X-axis (log scale) and fluorescence or absorbance on the Y-axis (linear scale). The T1R-like Ligand II polypeptide concentration in a sample is then interpolated using the standard curve based on the measured flourescence of that sample.

Example 11

Method of Treating Increased Levels of T1R-like Ligand II Using an Antagonist

The present invention relates to a method for treating an individual in need of a decreased level of T1R-like Ligand II biological activity in the body comprising, administering to such an individual a composition comprising a therapeutically effective amount of T1R-like Ligand II antagonist. Preferred antagonists for use in the present invention are T1R-like Ligand II specific antibodies and antisense polynucleotides.

Antisense technology is used to inhibit production of T1R-Like Ligand II. This technology is one example of a method of decreasing levels of T1R-like Ligand II polypeptide, preferably a soluble and/or secreted form, due to a variety of etiologies, such as cancer.

For example, a patient diagnosed with abnormally increased levels of T1R-Like Ligand II is administered intravenously antisense polynucleotides at 0.5, 1.0, 1.5, 2.0 and 3.0 mg/kg day for 21 days. This treatment is repeated after a 7-day rest period if the is determined to be well tolerated.

In another example, a patient with increased levels of T1R-Like Ligand II polypeptide receives a daily dose 0.1-100 ug/kg of an antagonist for six consecutive days. Preferably, the antagonist is in a soluble and/or secreted form.

Example 12

Method of Treating Decreased Levels of T1R-like Ligand II

The present invention also relates to a method for treating an individual in need of an increased level of T1R-Like Ligand II biological activity in the body comprising administering to such an individual a composition comprising a therapeutically effective amount of T1R-Like Ligand II or an agonist thereof.

For example, a patient with decreased levels of T1R-like Ligand II polypeptide receives a daily dose 0.1-100 μg/kg of agonist and/or polypeptide for six consecutive days. Preferably, the agonist and/or polypeptide is in a soluble and/or secreted form.

Example 13

Method of Treatment Using Gene Therapy—Ex Vivo

One method of gene therapy transplants fibroblasts, which are capable of expressing soluble and/or mature T1R-Like Ligand II polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calfintestinal phosphatase. The linear vector is fractionated on agarose gel and purified, using glass beads.

The cDNA encoding T1R-like Ligand II can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform E. coli HB101, which are then plated onto agar containing kanamycin for the purpose of confirming that the vector contains properly inserted T1R-Like Ligand II.

The amphotropic pA317 or GP+am12 packaging cells are grown in tissue culture to confluent densit, in Dulbecco's Modified Eagles Medium (DMEM) with 10% calf serum (CS), penicillin and streptomycin. The MSV vector containing the T1R-like Ligand II gene is then added to the media and the packaging cells transduced with the vector. The packaging cells now produce infectious viral particles containing the T1R-like Ligand II gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether T1R-Like Ligand II protein is produced.

The engineered fibroblasts are then transplanted onto the host, either alone or after having been grown to confluence on cytodex 3 microcarrier beads.

Example 14

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) T1R-like ligand II sequences into an animal to increase or decrease the expression of the T1R-like ligand II polypeptide. The T1R-like ligand II polynucleotide may be operatively linked to a promoter or any other genetic elements necessary for the expression of the T1R-like ligand II polypeptide by the target tissue. Such gene therapy and delivery techniques and methods are known in the art, see, for example, WO90/11092, WO98/11779; U.S. Pat. No. 5,693,622, 5,705,151, 5,580,859; Tabata H. et al., Cardiovasc. Res. 35:470-479 (1997); Chao J. et al. Pharmacol. Res. 35:517-522 (1997); Wolff J. A. Neuromuscul. Disord. 7:314-318 (1997); Schwartz B. et al., Gene Ther. 3:405-411 (1996); Tsurumi Y. et al., Circulation 94:3281-3290 (1996) (incorporated herein by reference).

The T1R-like ligand II polynucleotide constructs may be delivered by any method that delivers injectable materials to the cells of an animal, such as, injection into the interstitial space of tissues (heart, muscle, skin, lung, liver, intestine and the like). The T1R-like ligand II polynucleotide constructs can be delivered in a pharmaceutically acceptable liquid or aqueous carrier.

The term "naked" polynucleotide, DNA or RNA, refers to sequences that are free from any delivers vehicle that acts to assist, promote, or facilitate entry into the cell, including viral sequences, viral particles, liposome formulations, lipofectin or precipitating agents and the like. However, the T1R-like ligand II polynucleotides may also be delivered in liposome formulations (such as those taught in Felgner P. L. et al. (1995) Ann. NY Acad. Sci. 772:126-139 and Abdallah B. et al. (1995) Biol. Cell 85(1): 1-7) which can be prepared by methods well known to those skilled in the art.

The T1R-like ligand II polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The T1R-like ligand II polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed herein. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked T1R-like ligand II polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked T1R-like ligand II polynucleotide constructs can be delivered to arteries during angioplasty by the catheter used in the procedure.

The dose response effects of injected T1R-like ligand II polynucleotide in muscle in vivo is determined as follows. Suitable T1R-like ligand II template DNA for production of mRNA coding for T1R-like Ligand II polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The T1R-like ligand II template DNA is injected in 0.1 ml of carrier in a I cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for T1R-like ligand II protein expression. A time course for T1R-like ligand II protein expression may be done in a similar fashion except that quadriceps from different mice are harvested at different times. Persistence of T1R-like ligand II DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using T1R-like ligand II naked DNA.

Example 15

Bioassay for the Effect of T1R-Like Ligand II on Hematopoietic Progenitor Cells and/or Differentiation Mouse bone marrow cells are used as target cells to examine the effect of T1R-like ligand II polypeptides of the invention on hematopoietic progenitor cells and/or differentiation. Briefly, unfractionated bone marrow cells are first washed 2× with a serum-free IMDM that is supplemented with 10% (V/V) BIT (Bovine serum albumin, Insulin and Transferrin supplement from Stem Cell Technologies, Vancouver, Canada). The washed cells are then resuspended in the same growth medium and plated in the 96-well tissue culture plate (5×104 cells/well) in 0.2 ml of the above medium in the presence or absence of cytokines and T1R-like ligand II. Stem cell factor (SCF) and IL-3 are included as positive mediators of cell proliferation. Cells are allowed to grow in a low oxygen environment (5% $CO_2$, 7% $O_2$, and 88% $N_2$) tissue culture incubator for 6 days. On the sixth day, 0.5 Ci of Tritiated thymidine is added to each well and incubation is continued for an additional 16-18 hours, at which point the cells are harvested. The level of radioactivity incorporated into cellular DNA is determined by scintillation spectrometry and reflects the amount of cell proliferation.

The studies described in this example test the activity of T1R-like ligand II polypeptides of the invention. However, one skilled in the art could easily modify the exemplified studies to test the activity of T1R-like ligand II polynucleotides (e.g., gene therapy), agonists, and/or antagonists of T1R-like Ligand II. Potential agonists would be expected to inhibit hematopoictic cell proliferation in the presence of SCF and/or IL3 and/or to increase the inhibition of cell proliferation in the presence of cytokines and T1R-like ligand II in this assay. Potential antagonists would be expected to reduce the inhibition of cell proliferation in the presence of cytokines and T1R-like ligand II in this assay.

Example 16

Bioassay for the Effect of T1R-like Ligand II on IL-3 and SCF Stimulated Proliferation and Differentiation of Heniatopoietic Progenitor Cells To determine if T1R-like ligand II polypeptides of the invention inhibit specific hematopoietic lineages, mouse bone marrow cells are first washed 2× with a serum-free IMDM that is supplemented with 10% (V/V) BIT (Bovine serum albumin, Insulin and Transferrin supplement from Stem Cell Technologies, Vancouver, Canada). The washed cells are then resuspended in the same growth medium and plated in the 96-well tissue culture plate (5×104 cells/well) in 0.2 ml of the above medium in the presence of IL-3 (1 ng/ml) plus SCF (5 ng/ml) with or without T1R-like ligand II. Cells are allowed to grow in a low oxygen environment (5% $CO_2$, 7% $O_2$, and 88% $N_2$) tissue culture incubator, and after 7 days, analyzed for expression of differentiation antigens by staining with various monoclonal antibodies and FACScan.

The studies described in this example test the activity of T1R-like ligand II polypeptides of the invention. However, one skilled in the art could easily modify the exemplified studies to test the activity of T1R-like ligand II polynucleotides (e.g., gene therapy), agonists, and/or antagonists of T1R-like Ligand II. Potential agonists tested in this assay would be expected to inhibit cell proliferation in the presence of cytokines and/or to increase the inhibition of cell proliferation in the presence of cytokines and T1R-like ligand II. Potential antagonists tested in this assay would be expected to reduce the inhibition of cell proliferation in the presence of cytokines and T1R-like ligand II.

Example 17

Effect of T1R-like Ligand II on IL-3 and SCF Stimulated Proliferation and Differentiation of Lin-population of Bone Marrow Cells A population of mouse bone marrow cells enriched in primitive hematopoietic progenitors can be obtained using a negative selection procedure, where the committed cells of most of the lineages are removed using a panel of monoclonal antibodies (anti cdl 1b, CD4, CD8, CD45R and Gr-1 antigens) and magnetic beads. The resulting population of cells (lineage depleted cells) are plated (5×104 cells/ml) in the presence or absence of T1R-like ligand II polypeptide of the invention (in a range of concentrations) in a growth medium supplemented with IL-3 (5 ng/ml) plus SCF (100 ng/ml). After seven days of incubation at 37° C. in a humidified incubator (5% $CO_2$, 7% 02, and 88% $N_2$ environment), cells are harvested and assayed for the HPP-CFC, and immature progenitors. In addition, cells are analyzed for the expression of certain differentiation antigens by FACScan. Colony data is expressed as mean number of colonies +/−SD) and are obtained from assays performed in six dishes for each population of cells.

Example 18

T1R-like Ligand II Stimulates the Proliferation of Bone Marrow CD34+ Cells.

This assay was based on the ability of human CD34+ to proliferate in presence of hematopoietic growth factors and evaluated the ability of isolated T1R-like ligand II polypeptides expressed in mammalian cells to stimulate proliferation of CD34+ cells.

It has been previously shown that only most mature precursors will respond to a single signal. More immature precursors require at least two signals to respond. Therefore, to test the effect of T I receptor-like ligand II polypeptides on hematopoletic activity of a wide range of progenitor cells, the assay contained T1R-like ligand II in presence or absence of other hematopoietic growth factors. Isolated cells were cultured for 5 days in the presence of Stem Cell Factor (SCF) in combination with tested supernatant. SCF alone has a very limited effect on the proliferation of bone marrow (BM) cells, acting in such conditions only as a "survival" factor. However, combined with any factor exhibiting stimulatory effect on these cells (i.e. IL-3), SCF will cause a synergistic effect. Therefore, if the tested polypeptide has a stimulatory effect on hematopoietic progenitors, such activity can be easily detected. Since normal BM cells have a low level of cycling cells, it is likely that any inhibitory effect of the polypeptides of the invention, or agonists or antagonists thereof, might not be detected, accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+ cells were isolated using methods known in the art. The cells were thawed and resuspended in medium (QBSF 60 serum-free medium with L-glutamine (500 ml) Quality Biological, inc. Gaithersburg, MD, Cat# 160-204-101). After several gentle centrifugation steps at 200× g, they were allowed to rest for one hour. The cell count was then adjusted to $2.5 \times 10^5$ cells/ml. During this time, 100 µl of sterile water was added to the peripheral wells of a 96-well plate. The cytokines that were tested with T1 receptor-like ligand II in this assay were rhSCF (R&D Systems, Minneapolis, Minn., Cat# 255-SC) at 50 ng/ml alone and in combination with rhSCF and rhIL-3 (R&D Systems, Minneapolis, Minn., Cat# 203-ML) at 30 ng/ml. After one hour, 10 µl of prepared cytokines, 50 µl SID (supernatants at 1:2 dilution=50 µl) and 20 µl of diluted cells were added to the media which was already present in the wells to allow for a final total volume of 100 µl. The plates were then placed in a 37° C/5% $CO_2$ incubator for five days.

Eighteen hours before the assay was harvested, 0.5 µCi/well of [3H] Thymidine was added in a 10 µl volume to each well to determine the proliferation rate. The experiment was terminated by harvesting the cells from each 96 well plate to a filtermat using the Tomtec Harvester 96. After harvesting, the filtermats were dried, trimmed and placed into Omni-Filter assemblies consisting of one OmniFilter plate and one OmniFilter Tray. 60 µl Microscint was added to each well and the plate sealed with TopSeal-A press-on sealing film. A bar code 15 sticker was affixed to the first plate for counting. The sealed plates were then loaded and the level of radioactivity determined via the Packard Top Count and the printed data collected for analysis. The level of radioactivity reflected the amount of cell proliferation.

Figure 4:
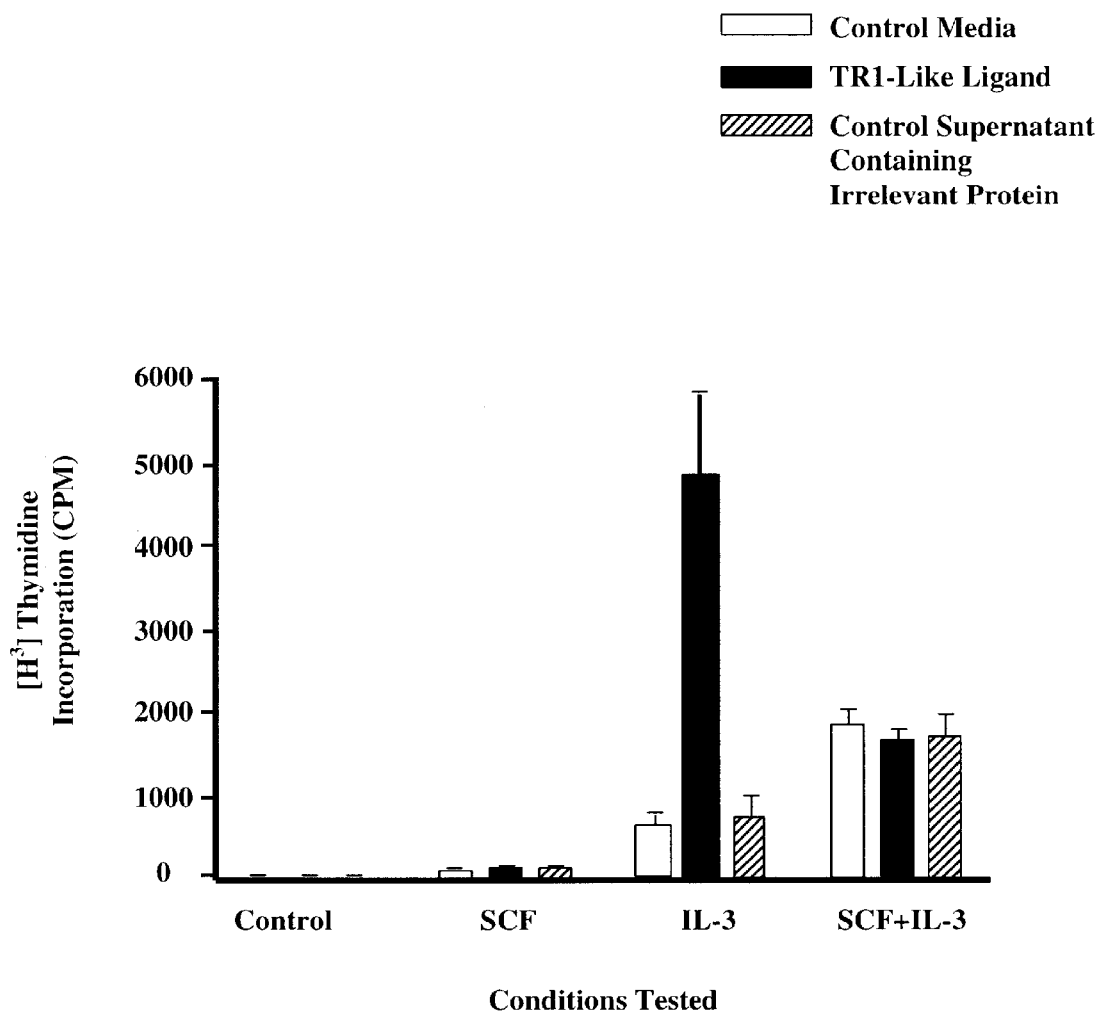
FIG. 4 shows the effect of T1R-like ligand II containing supernatant on CD34+ Bone Marrow Proliferation Assay.

FIG. 4 shows the results of one such assay using isolated T1R-like ligand II polypeptides expressed in mammalian cells. The values were averaged and standard deviations calculated using Microsoft 98 Excel. Hits are determined by averaging all of the mean values for the SID Lite supernatants and controls and adding 1 SD to that value. Any SID Lite supernatants whose average value exceeds this value are considered as hits.

The studies described in the above example test the activity of T1R-like ligand II polypeptides of the invention. However, one skilled in the art could easily modify the exemplified studies to test the activity of T1R-like ligand II polynucleotides (e.g., gene therapy), antibodies, agonists, and/or antagonists and fragments and variants thereof. As a nonlimiting example, potential antagonists tested in this assay would be expected to inhibit cell proliferation in the presence of cytokines and/or to increase the inhibition of cell proliferation in the presence of cytokines and T1R-like ligand II. Potential agonists tested in this assay would be expected to reduce the inhibition of cell proliferation in the presence of cytokines and T1R-like ligand II.

What is claimed is:

1. A method of stimulating bone marrow cell proliferation, comprising contacting said cell with a protein comprising an amino acid sequence selected from the group consisting of:

(a) amino acids 1 to 168 of SEQ ID NO:2;
(b) amino acids 1 to 203 of SEQ ID NO:2;
(c) amino acids −25 to 203 of SEQ ID NO:2;
(d) amino acids −26 to 203 of SEQ ID NO:2;
(e) the mature amino acid sequence encoded by the cDNA contained in ATCC Deposit No. 97655; and
(f) the complete amino acid sequence encoded by the cDNA contained in ATCC Deposit No. 97655.

2. The method of claim 1, wherein said protein comprises amino acids 1 to 168 of SEQ ID NO:2.

3. The method of claim 1, wherein said protein comprises amino acids 1 to 203 of SEQ ID NO:2.

4. The method of claim 1, wherein said protein comprises amino acids −25 to 203 of SEQ ID NO:2.

5. The method of claim 1, wherein said protein comprises amino acids −26 to 203 of SEQ ID NO:2.

6. The method of claim 1, wherein said protein comprises the mature amino acid sequence encoded by the cDNA contained in ATCC Deposit No. 97655.

7. The method of claim 1, wherein said protein comprises the complete amino acid sequence encoded by the cDNA contained in ATCC Deposit No. 97655.

8. The method of claim 1, wherein said contacting occurs in vitro.

9. The method of claim 1, wherein said contacting occurs in vivo.

10. The method of claim 1, wherein said protein is glycosylated.

11. The method of claim 1, wherein said protein is fused to polyethylene glycol.

12. The method of claim 1, wherein said protein comprises an N-terminal Met residue.

13. The method of claim 1, wherein said protein comprises Fc.

14. The method of claim 1, wherein said protein comprises a heterologous polypeptide.

15. A method of stimulating bone marrow cell proliferation, comprising contacting said cell with a protein comprising an amino acid sequence at least 95% identical to a member selected from the group consisting of:

(a) amino acids 1 to 168 of SEQ ID NO:2;
(b) amino acids 1 to 203 of SEQ ID NO:2;
(c) amino acids −25 to 203 of SEQ ID NO:2;
(d) amino acids −26 to 203 of SEQ ID NO:2;
(e) the mature amino acid sequence encoded by the eDNA contained in ATCC Deposit No. 97655; and
(f) the complete amino acid sequence encoded by the cDNA contained in ATCC Deposit No. 97655;
wherein said protein has the activity of stimulating the proliferation of bone marrow cells.

16. The method of claim 15, wherein said protein comprises an amino acid sequence at least 95% identical to amino acids 1 to 168 of SEQ ID NO:2.

17. The method of claim 15, wherein said protein comprises an amino acid sequence at least 95% identical to amino acids 1 to 203 of SEQ ID NO:2.

18. The method of claim 15, wherein said protein comprises an amino acid sequence at least 95% identical to amino acids −25 to 203 of SEQ ID NO:2.

19. The method of claim 15, wherein said protein comprises an amino acid sequence at least 95% identical to amino acids −26 to 203 of SEQ ID NO:2.

20. The method of claim 15, wherein said protein comprises an amino acid sequence at least 95% identical to the mature amino acid sequence encoded by the cDNA contained in ATCC Deposit No. 97655.

21. The method of claim 15, wherein said protein comprises an amino acid sequence at least 95% identical to the complete amino acid sequence encoded by the cDNA contained in ATCC Deposit No. 97655.

22. The method of claim 15, wherein said contacting occurs in vitro.

23. The method of claim 15, wherein said contacting occurs in vivo.

24. The method of claim 15, wherein said protein is glycosylated.

25. The method of claim 15, wherein said protein is fused to polyethylene glycol.

26. The method of claim 15, wherein said protein comprises an N-terminal Met residue.

27. The method of claim 15, wherein said protein comprises Fc.

28. The method of claim 15, wherein said protein comprises a heterologous polypeptide.

29. A method of stimulating bone marrow cell proliferation, comprising contacting said cell with a protein comprising an amino acid sequence which, except for one to five conservative amino acid substitutions, is identical to a member selected from the group consisting of:

(a) amino acids 1 to 168 of SEQ ID NO:2;
(b) amino acids 1 to 203 of SEQ ID NO:2;
(c) amino acids −25 to 203 of SEQ ID NO:2;
(d) amino acids −26 to 203 of SEQ ID NO:2;
(e) the mature amino acid sequence encoded by the cDNA contained in ATCC Deposit No. 97655; and
(f) the complete amino acid sequence encoded by the cDNA contained in ATCC Deposit No. 97655;
wherein said protein has the activity of stimulating the proliferation of bone marrow cells.

30. The method of claim 29, wherein said protein comprises an amino acid sequence which, except for one to five conservative amino acid substitutions, is identical to amino acids 1 to 168 of SEQ ID NO:2.

31. The method of claim 29, wherein said protein comprises an amino acid sequence which, except for one to five conservative amino acid substitutions, is identical to amino acids 1 to 203 of SEQ ID NO:2.

32. The method of claim 29, wherein said protein comprises an amino acid sequence which, except for one to five conservative amino acid substitutions, is identical to amino acids −25 to 203 of SEQ ID NO:2.

33. The method of claim 29, wherein said protein comprises an amino acid sequence which, except for one to five conservative amino acid substitutions, is identical to amino acids −26 to 203 of SEQ ID NO:2.

34. The method of claim 29, wherein said protein comprises an amino acid sequence which, except for one to five conservative amino acid substitutions, is identical to the mature amino acid sequence encoded by the cDNA contained in ATCC Deposit No. 97655.

35. The method of claim 29, wherein said protein comprises an amino acid sequence which, except for one to five conservative amino acid substitutions, is identical to the complete amino acid sequence encoded by the cDNA contained in ATCC Deposit No. 97655.

36. The method of claim 29, wherein said contacting occurs in vitro.

37. The method of claim 29, wherein said contacting occurs in vivo.

38. The method of claim 29, wherein said protein is glycosylated.

39. The method of claim 29, wherein said protein is fused to polyethylene glycol.

40. The method of claim 29, wherein said protein comprises an N-terminal Met residue.

41. The method of claim 29, wherein said protein comprises Fc.

42. The method of claim 29, wherein said protein comprises a heterologous polypeptide.

43. A method of stimulating bone marrow cell proliferation comprising contacting said cell with a protein comprising a fragment of the amino acid sequence of SEQ ID NO:2, wherein said fragment has the activity of stimulating the proliferation of bone marrow cells.

44. The method of claim 43, wherein said contacting occurs in vitro.

45. The method of claim 43, wherein said contacting occurs in vivo.

46. The method of claim 43, wherein said protein is glycosylated.

47. The method of claim 43, wherein said protein is fused to polyethylene glycol.

48. The method of claim 43, wherein said protein comprises an N-terminal Met residue.

49. The method of claim 43, wherein said protein comprises Fc.

50. The method of claim 43, wherein said protein comprises a heterologous polypeptide.

51. A method of stimulating bone marrow cell proliferation comprising contacting said cell with a protein comprising a fragment of the complete amino acid sequence encoded by the eDNA clone contained in ATCC Deposit No. 97655, wherein said fragment has the activity of stimulating the proliferation of bone marrow cells.

52. The method of claim 51, wherein said contacting occurs in vitro.

53. The method of claim 51, wherein said contacting occurs in vivo.

54. The method of claim 51, wherein said protein is glycosylated.

55. The method of claim 51, wherein said protein is fused to polyethylene glycol.

56. The method of claim 51, wherein said protein comprises an N-terminal Met residue.

57. The method of claim 51, wherein said protein comprises Fc.

58. The method of claim 51, wherein said protein comprises a heterologous polypeptide.

* * * * *

SEQUENCE LISTING

```
<160> NUMBER OF SEQ ID NOS: 26

<210> SEQ ID NO 1
<211> LENGTH: 1243
<212> TYPE: DNA
<213> ORGANISM: TIR-Like Ligand II
<220> FEATURE:
<221> NAME/KEY: CDS
<222> LOCATION: (54)..(740)
<221> NAME/KEY: sig_peptide
<222> LOCATION: (54)..(132)
<221> NAME/KEY: mat_peptide
<222> LOCATION: (132)..()

<400> SEQUENCE: 1
acgaggacaa cagtacctga cgcctctttc agcccgggat cgccccagca ggg atg          56
                                                              Met ggc gac aag atc tgg ctg ccc ttc ccc gtg ctc ctt ctg gcc gct ctg         104
Gly Asp Lys Ile Trp Leu Pro Phe Pro Val Leu Leu Leu Ala Ala Leu
-25             -20                 -15                 -10 cct ccg gtg ctg ctg cct ggg gcg gcc ggc ttc aca cct tcc ctc gat         152
Pro Pro Val Leu Leu Pro Gly Ala Ala Gly Phe Thr Pro Ser Leu Asp
            -5                  -1  1               5 agc gac ttc acc ttt acc ctt ccc gcc ggc cag aag gag tgc ttc tac         200
Ser Asp Phe Thr Phe Thr Leu Pro Ala Gly Gln Lys Glu Cys Phe Tyr
            10                  15              20 cag ccc atg ccc ctg aag gcc tcg ctg gag atc gag tac caa gtt tta         248
Gln Pro Met Pro Leu Lys Ala Ser Leu Glu Ile Glu Tyr Gln Val Leu
        25                  30                  35 gat gga gca gga tta gat att gat ttc cat ctt gcc tct cca gaa ggc         296
Asp Gly Ala Gly Leu Asp Ile Asp Phe His Leu Ala Ser Pro Glu Gly
40                  45                  50                  55 aaa acc tta gtt ttt gaa caa aga aaa tca gat gga gtt cac act gta         344
Lys Thr Leu Val Phe Glu Gln Arg Lys Ser Asp Gly Val His Thr Val
                60                  65                  70 gag act gaa gtt ggt gat tac atg ttc tgc ttt gac aat aca ttc agc         392
Glu Thr Glu Val Gly Asp Tyr Met Phe Cys Phe Asp Asn Thr Phe Ser
            75                  80                  85 acc att tct gag aag gtg att ttc ttt gaa tta atc ctg gat aat atg         440
Thr Ile Ser Glu Lys Val Ile Phe Phe Glu Leu Ile Leu Asp Asn Met
        90                  95                  100 gga gaa cag gca caa gaa caa gaa gat tgg aag aaa tat att act ggc         488
```

```
Gly Glu Gln Ala Gln Glu Gln Glu Asp Trp Lys Lys Tyr Ile Thr Gly
        105                 110                 115 aca gat ata ttg gat atg aaa ctg gaa gac atc ctg gaa tcc atc aac    536
Thr Asp Ile Leu Asp Met Lys Leu Glu Asp Ile Leu Glu Ser Ile Asn
120                 125                 130                 135 agc atc aag tcc aga cta agc aaa agt ggg cac ata caa act ctg ctt    584
Ser Ile Lys Ser Arg Leu Ser Lys Ser Gly His Ile Gln Thr Leu Leu
                140                 145                 150 aga gca ttt gaa gct cgt gat cga aac ata caa gaa agc aac ttt gat    632
Arg Ala Phe Glu Ala Arg Asp Arg Asn Ile Gln Glu Ser Asn Phe Asp
            155                 160                 165 aga gtc aat ttc tgg tct atg gtt aat tta gtg gtc atg gtg gtg gtg    680
Arg Val Asn Phe Trp Ser Met Val Asn Leu Val Val Met Val Val Val
        170                 175                 180 tca gcc att caa gtt tat atg ctg aag agt ctg ttt gaa gat aag agg    728
Ser Ala Ile Gln Val Tyr Met Leu Lys Ser Leu Phe Glu Asp Lys Arg
    185                 190                 195 aaa agt aga act taaaactcca aactagagta cgtaacattg aaaaatgagg        780
Lys Ser Arg Thr
200 cataaaaatg ccataaactg ttacagtcca gaccattaat ggtcttctcc aaaatatttt   840 gagatataaa agtaggaaac aggtataatt ttaatgtgaa aattaagtct tcactttctg   900 tgcaagtaat cctgctgatc cagttgtact taagtgtgta acaggaatat tttgcagaat   960 ataggtttaa ctgaatgaag ccatattaat aactgcattt tcctaacttt gaaaattttt  1020 gcaaatgtct taggtgattt aaataaatga gtattgggcc taattgcaac accagtctgt  1080 ttttaacagg ttctattacc cagaactttt ttgtaaatgc ggcagttaca aattaactgt  1140 ggaagttttc agtttaagt tataaatcac ctgagaatta cctaatgatg gattgaataa  1200 atctttagac tacaaaaaaa aaaaaaaaaa aaaaaaaaa aaa                    1243

<210> SEQ ID NO 2
<211> LENGTH: 229
<212> TYPE: PRT
<213> ORGANISM: TIR-Like Ligand II Protein

<400> SEQUENCE: 2

Met Gly Asp Lys Ile Trp Leu Pro Phe Pro Val Leu Leu Ala Ala
    -25                 -20                 -15

Leu Pro Pro Val Leu Leu Pro Gly Ala Ala Gly Phe Thr Pro Ser Leu
-10                 -5                  -1  1                   5

Asp Ser Asp Phe Thr Phe Thr Leu Pro Ala Gly Gln Lys Glu Cys Phe
            10                  15                  20

Tyr Gln Pro Met Pro Leu Lys Ala Ser Leu Glu Ile Glu Tyr Gln Val
        25                  30                  35

Leu Asp Gly Ala Gly Leu Asp Ile Asp Phe His Leu Ala Ser Pro Glu
    40                  45                  50

Gly Lys Thr Leu Val Phe Glu Gln Arg Lys Ser Asp Gly Val His Thr
55                  60                  65                  70

Val Glu Thr Glu Val Gly Asp Tyr Met Phe Cys Phe Asp Asn Thr Phe
                75                  80                  85

Ser Thr Ile Ser Glu Lys Val Ile Phe Phe Glu Leu Ile Leu Asp Asn
            90                  95                  100

Met Gly Glu Gln Ala Gln Glu Gln Glu Asp Trp Lys Lys Tyr Ile Thr
        105                 110                 115

Gly Thr Asp Ile Leu Asp Met Lys Leu Glu Asp Ile Leu Glu Ser Ile
```

-continued

```
                120                 125                 130
Asn Ser Ile Lys Ser Arg Leu Ser Lys Ser Gly His Ile Gln Thr Leu
135                 140                 145                 150

Leu Arg Ala Phe Glu Ala Arg Asp Arg Asn Ile Gln Glu Ser Asn Phe
                155                 160                 165

Asp Arg Val Asn Phe Trp Ser Met Val Asn Leu Val Val Met Val Val
                170                 175                 180

Val Ser Ala Ile Gln Val Tyr Met Leu Lys Ser Leu Phe Glu Asp Lys
            185                 190                 195

Arg Lys Ser Arg Thr
            200

<210> SEQ ID NO 3
<211> LENGTH: 227
<212> TYPE: PRT
<213> ORGANISM: Human putative T1/ST2 receptor binding protein precursor
      mRNA
<300> PUBLICATION INFORMATION:
<308> DATABASE ACCESSION NUMBER: Genbank/U41804
<309> DATABASE ENTRY DATE: 1996-04-02
<313> RELEVANT RESIDUES: (1)..(227)

<400> SEQUENCE: 3

Met Met Ala Ala Gly Ala Ala Leu Ala Leu Ala Leu Trp Leu Leu Met
1               5                   10                  15

Pro Pro Val Glu Val Gly Gly Ala Gly Pro Pro Ile Gln Asp Gly
            20                  25                  30

Glu Phe Thr Phe Leu Leu Pro Ala Gly Arg Lys Gln Cys Phe Tyr Gln
                35                  40                  45

Ser Ala Pro Ala Asn Ala Ser Leu Glu Thr Glu Tyr Gln Val Ile Gly
        50                  55                  60

Gly Ala Gly Leu Asp Val Asp Phe Thr Leu Glu Ser Pro Gln Gly Val
65                  70                  75                  80

Leu Leu Val Ser Glu Ser Arg Lys Ala Asp Gly Val His Thr Val Glu
                85                  90                  95

Pro Thr Glu Ala Gly Asp Tyr Lys Leu Cys Phe Asp Asn Ser Phe Ser
            100                 105                 110

Thr Ile Ser Glu Lys Leu Val Phe Phe Glu Leu Ile Phe Asp Ser Leu
        115                 120                 125

Gln Asp Asp Glu Glu Val Glu Gly Trp Ala Glu Ala Val Glu Pro Glu
130                 135                 140

Glu Met Leu Asp Val Lys Met Glu Asp Ile Lys Glu Ser Ile Glu Thr
145                 150                 155                 160

Met Arg Thr Arg Leu Glu Arg Ser Ile Gln Met Leu Thr Leu Leu Arg
                165                 170                 175

Ala Phe Glu Ala Arg Asp Arg Asn Leu Gln Glu Gly Asn Leu Glu Arg
            180                 185                 190

Val Asn Phe Trp Ser Ala Val Asn Val Ala Val Leu Leu Val Ala
        195                 200                 205

Val Leu Gln Val Cys Thr Leu Lys Arg Phe Phe Gln Asp Lys Arg Pro
    210                 215                 220

Val Pro Thr
225

<210> SEQ ID NO 4
<211> LENGTH: 26
<212> TYPE: DNA
```

<213> ORGANISM: Oligonucleotide Primer

<400> SEQUENCE: 4
cgcccatggc cggcttcaca ccttcc                                    26

<210> SEQ ID NO 5
<211> LENGTH: 30
<212> TYPE: DNA
<213> ORGANISM: Oligonucleotide Primer

<400> SEQUENCE: 5
cgcaagcttt catctatcaa agttgctttc                                30

<210> SEQ ID NO 6
<211> LENGTH: 33
<212> TYPE: DNA
<213> ORGANISM: Oligonucleotide Primer

<400> SEQUENCE: 6
cgcggatccg ccatcatggg cgacaagatc tgg                            33

<210> SEQ ID NO 7
<211> LENGTH: 30
<212> TYPE: DNA
<213> ORGANISM: Oligonucleotide Primer

<400> SEQUENCE: 7
cgcggtacct cacaatgtta cgtactctag                                30

<210> SEQ ID NO 8
<211> LENGTH: 30
<212> TYPE: DNA
<213> ORGANISM: Oligonucleotide Primer

<400> SEQUENCE: 8
cgcggtacct catctatcaa agttgctttc                                30

<210> SEQ ID NO 9
<211> LENGTH: 57
<212> TYPE: DNA
<213> ORGANISM: Oligonucleotide Primer

<400> SEQUENCE: 9
cgctctagat caagcgtagt ctgggacgtc gtatgggtat ctatcaaagt tgctttc   57

<210> SEQ ID NO 10
<211> LENGTH: 24
<212> TYPE: DNA
<213> ORGANISM: Oligonucleotide Primer

<400> SEQUENCE: 10
tgacagaggg actttccgag agga                                      24

<210> SEQ ID NO 11
<211> LENGTH: 390
<212> TYPE: DNA
<213> ORGANISM: HPVAA83R
<220> FEATURE:
<221> NAME/KEY: misc_feature
<222> LOCATION: (35)..(35)
<223> OTHER INFORMATION: n is any nucleotide
<221> NAME/KEY: misc_feature
<222> LOCATION: (364)..(364)
<223> OTHER INFORMATION: n is any nucleotide
<221> NAME/KEY: misc_feature
<222> LOCATION: (378)..(378)
<223> OTHER INFORMATION: n is any nucleotide

<400> SEQUENCE: 11

```
aattcggcac gagcttctac cagcccatgc ccctnaaggc ctcgctggag atcgagtacc    60
aagttttaga tggagcagga ttagatattg atttcccatc ttgcctctcc agaaggcaaa   120
accttagttt ttgaacaaag aaaatcagat ggagttcaca cgtgtataag aagtaaaaat   180
gggccaggca ctgcggttca cgcctataat cccagcactt tccgaggccg agtgtagaga   240
ctgaagttgg tgattacatg ttctgctttg acaatacatt cagcaccatt tctgagaagg   300
tgattttctt tgaattaatc ctggataata tgggaggaca ggcacaagac aagaggtttg   360
gagnatattt actggccnat ttatggtatg                                    390
```

<210> SEQ ID NO 12
<211> LENGTH: 530
<212> TYPE: DNA
<213> ORGANISM: Soares retina N2b4HR
<220> FEATURE:
<221> NAME/KEY: misc_feature
<222> LOCATION: (54)..(54)
<223> OTHER INFORMATION: n is any nucleotide
<221> NAME/KEY: misc_feature
<222> LOCATION: (173)..(173)
<223> OTHER INFORMATION: n is any nucleotide
<221> NAME/KEY: misc_feature
<222> LOCATION: (177)..(177)
<223> OTHER INFORMATION: n is any nucleotide
<300> PUBLICATION INFORMATION:
<308> DATABASE ACCESSION NUMBER: GenBank/AA013099
<309> DATABASE ENTRY DATE: 1996-07-16
<313> RELEVANT RESIDUES: (1)..(530)

<400> SEQUENCE: 12

```
agactccaga tttccctgtc aaccacgagg agtccagaga ggaaacgcgg agangaacaa    60
cagtacctga cgcctctttc agcccgggat cgccccagca gggatgggcg acaagatctg   120 gctgccttc cccgtgctcc ttctggccgc tctgcctccg gtgctgctgc ctngggncgg    180
ccggcttcac accttccctc gatagcgact tcacctttac ccttcccgcc ggccagaagg   240
agtgcttcta ccagcccatg ccctgaagg cctcgctgga gatcgagtac caagttttag   300
atggagcagg attagatatt gatttccatc ttgcctctcc agaaggcaaa accttagttt   360
ttgaacaaag aaaatcagat ggagttcaca ctgtagagac tgaagttggt gattacatgt   420
tctgctttga caatacattc agcaccattt ctgagaaggt gattttcttt gaattaatcc   480
tggataatat gggagaacag gcacaagaac aagaagattg gaagaaatat               530
```

<210> SEQ ID NO 13
<211> LENGTH: 463
<212> TYPE: DNA
<213> ORGANISM: NCI_CGAP_GCB1
<300> PUBLICATION INFORMATION:
<308> DATABASE ACCESSION NUMBER: GenBank/AA251084
<309> DATABASE ENTRY DATE: 1997-01-31
<313> RELEVANT RESIDUES: (1)..(463)

<400> SEQUENCE: 13

```
agactccaga tttccctgtc aaccacgagg agtccagaga ggaaacgcgg agcgcacaac    60
agtacctgac gcctctttca gcccgggatc gccccagcag ggatgggcga caagatctgg   120
ctgcccttcc ccgtgctcct tctggccgct ctgcctccgg tgctgctgcc tggggcggcc   180
ggcttcacac cttccctcga tagcgacttc acctttaccc ttcccgccgg ccagaaggag   240
```

```
tgcttctacc agcccatgcc cctgaaggcc tcgctggaga tcgagtacca agttttagat    300
ggagcaggat tagatattga tttccatctt gcctctccag aaggcaaaac cttagttttt    360
gaacaaagaa aatcagatgg agttcacact gtagagactg aagttggtga ttacatgttc    420
tgctttgaca atacattcag caccatttct gagaaggtga ttt                     463
```

<210> SEQ ID NO 14
<211> LENGTH: 196
<212> TYPE: DNA
<213> ORGANISM: fetal heart
<300> PUBLICATION INFORMATION:
<308> DATABASE ACCESSION NUMBER: GenBank/R58562
<309> DATABASE ENTRY DATE: 1995-05-23
<313> RELEVANT RESIDUES: (1)..(196)

<400> SEQUENCE: 14

```
gcagaatata ggtttaactg aatgaagcca tattaataac tgcatttgcc taacttggaa     60
aagtttggca aatgtcttag gtgatttaaa taaatgagta ttgggcctaa ttgccacacc    120
agtctgtttt gaacaggttc tattacccag aactttttg taaatgcggc agttacaaat    180
taactgttgg aggttt                                                   196
```

<210> SEQ ID NO 15
<211> LENGTH: 520
<212> TYPE: DNA
<213> ORGANISM: Soares melanocyte 2NbHM
<220> FEATURE:
<221> NAME/KEY: misc_feature
<222> LOCATION: (430)..(430)
<223> OTHER INFORMATION: n is any nucleotide
<221> NAME/KEY: misc_feature
<222> LOCATION: (474)..(474)
<223> OTHER INFORMATION: n is any nucleotide
<221> NAME/KEY: misc_feature
<222> LOCATION: (481)..(481)
<223> OTHER INFORMATION: n is any nucleotide
<221> NAME/KEY: misc_feature
<222> LOCATION: (511)..(511)
<223> OTHER INFORMATION: n is any nucleotide
<300> PUBLICATION INFORMATION:
<308> DATABASE ACCESSION NUMBER: GenBank/ N28878
<309> DATABASE ENTRY DATE: 1996-01-04
<313> RELEVANT RESIDUES: (1)..(520)

<400> SEQUENCE: 15

```
gcaaaacctt agttttttgaa caaagaaaat cagatggagt tcacactgta gagactgaag     60
ttggtgatta catgttctgc tttgacaata cattcagcac catttctgag aaggtgattt    120
tctttgaatt aatcctggat aatatgggag aacaggcaca agaacaagaa gattggaaga    180
aatatattac tggcacagat atattggata tgaaactgga agacatcctg gaatccatca    240
acagcatcaa gtccagacta agcaaaagtg ggcacataca aactctgctt agagcatttg    300
aagctcgtga tcgaaacata caagaaagca actttgatag agtcaatttc tggtctatgg    360
ttaatttagt ggtcatggtg gtggtgtcag ccattcaagt ttatatgctg aagagtctgg    420
tttgaagatn aggagggaaa gttggaactt aaaactccca aacttgggta cggnaccttg    480
naaaatgggg ccattaaaaa tgccattaac nggttccagc                         520
```

<210> SEQ ID NO 16
<211> LENGTH: 477
<212> TYPE: DNA
<213> ORGANISM: Soares retina N2b4HR
<220> FEATURE:
<221> NAME/KEY: misc_feature
<222> LOCATION: (176)..(176)

```
<223> OTHER INFORMATION: n is any nucleotide
<300> PUBLICATION INFORMATION:
<308> DATABASE ACCESSION NUMBER: GenBank/AA019348
<309> DATABASE ENTRY DATE: 1996-08-05
<313> RELEVANT RESIDUES: (1)..(477)

<400> SEQUENCE: 16
agactccaga tttccctgtc aaccacgagg agtccagaga ggaaacgcgg agatgaacaa    60
cagtacctga cgcctctttc agcccgggat cgccccagca gggatgggcg acaagatctg   120
gctgcccttc cccgtgctcc ttctggccgc tctgcctccg gtgctgctgc ctgggnggcc   180
ggcttcacac cttccctcga tagcgacttc acctttaccc ttcccgccgg ccagaaggag   240
tgcttctacc agcccatgcc cctgaaggcc tcgctggaga tcgagtacca agttttagat   300
ggagcaggat tagatattga tttccatctt gcctctccag aaggcaaaac cttagttttt   360
gaacaaagaa aatcagatgg gagttcacac tgtaagagac tgaagttggg tgattacatg   420
ttctgctttg acaatacatt cagcaccatt tctgagaagg tgatttcttt ggaatta      477

<210> SEQ ID NO 17
<211> LENGTH: 403
<212> TYPE: DNA
<213> ORGANISM: Soares_multiple_sclerosis_2NbHMSP
<220> FEATURE:
<221> NAME/KEY: misc_feature
<222> LOCATION: (322)..(322)
<223> OTHER INFORMATION: n is any nucleotide
<300> PUBLICATION INFORMATION:
<308> DATABASE ACCESSION NUMBER: GenBank/N49615
<309> DATABASE ENTRY DATE: 1996-02-14
<313> RELEVANT RESIDUES: (1)..(403)

<400> SEQUENCE: 17
gtagtctaaa gatttattca atccatcatt aggtaattct caggtgattt ataacttaaa    60
actgaaaact tccacagtta atttgtaact gccgcattta caaaaaagtt ctgggtaata   120
gaacctgtta aaaacagact ggtgttgcaa ttaggcccaa tactcattta tttaaatcac   180
ctaagacatt tgcaaaattt ttcaaagtta ggaaaatgca gttattaata tggcttcatt   240
cagttaaacc tatattctgc aaaatattcc tgttacacac ttaaggtaca actggatcag   300
caggattact tgcacagaaa gntgaagact taatttttcac attaaaatta tacctggttt   360 cctacttta tatcncaaaa tattttggga gaagaccatt aat                     403

<210> SEQ ID NO 18
<211> LENGTH: 396
<212> TYPE: DNA
<213> ORGANISM: Stratagene HeLa cell s3 937216
<220> FEATURE:
<221> NAME/KEY: misc_feature
<222> LOCATION: (111)..(111)
<223> OTHER INFORMATION: n is any nucleotide
<221> NAME/KEY: misc_feature
<222> LOCATION: (177)..(177)
<223> OTHER INFORMATION: n is any nucleotide
<221> NAME/KEY: misc_feature
<222> LOCATION: (191)..(191)
<223> OTHER INFORMATION: n is any nucleotide
<221> NAME/KEY: misc_feature
<222> LOCATION: (204)..(204)
<223> OTHER INFORMATION: n is any nucleotide
<300> PUBLICATION INFORMATION:
<308> DATABASE ACCESSION NUMBER: GenBank/AA112675
<309> DATABASE ENTRY DATE: 1996-11-27
<313> RELEVANT RESIDUES: (1)..(403)

<400> SEQUENCE: 18
```

```
tacctgacgc ctctttcagc ccgggatcgc cccagcagga atgggcgaca agatctggct    60
gcccttcccg tgctccttct ggccgctctg ctccggtgct gctgctggg nggccggctt   120 cacaccttcc ctcgatagcg acttcacctt taccttccgc cggcagaagg agtgctncta   180
ccagccatgc ncctgaaggc ctcnctggag atcgagtacc aagttttaga tggagcagga   240
ttagatattg atttccatct tgcctctcca agaaaggcaa aaccttaagt tttttgaacaa   300 agaaatcaga tggagttcac actgtagaga ctgaaagttg gtgattacat gttctgcttt   360
gacaatacat tcaagaacca tttctgagaa ggtgat                             396

<210> SEQ ID NO 19
<211> LENGTH: 309
<212> TYPE: DNA
<213> ORGANISM: Stratagene endothelial cell 937223
<300> PUBLICATION INFORMATION:
<308> DATABASE ACCESSION NUMBER: GenBank/AA082161
<309> DATABASE ENTRY DATE: 1996-06-24
<313> RELEVANT RESIDUES: (1)..(396)

<400> SEQUENCE: 19
ccagaaggag tgcttctacc agcccatgcc ccgtgaaggc ctcgctggag atcgagtacc    60
aagttttaga tggagcagga ttagatattg atttccatct tgcctctcca gaaggcaaaa   120
ccttagtttt tgaacaaaga aaatcagatg gagttcacac tgtagagact gaagttggtg   180
attacatgtt ctgctttgac aatacattca gcaccatttc tgagaaggtg attttctttg   240
aattaatcct ggataatatg ggagaacaag gcacaagaac aagaagattg gaagaaatat   300
attactggc                                                           309

<210> SEQ ID NO 20
<211> LENGTH: 462
<212> TYPE: DNA
<213> ORGANISM: Soares placenta Nb2HP
<220> FEATURE:
<221> NAME/KEY: misc_feature
<222> LOCATION: (461)..(461)
<223> OTHER INFORMATION: n is any nucleotide
<300> PUBLICATION INFORMATION:
<308> DATABASE ACCESSION NUMBER: GenBank/H03613
<309> DATABASE ENTRY DATE: 1995-06-20
<313> RELEVANT RESIDUES: (1)..(462)

<400> SEQUENCE: 20
attgatttcc atcttgcctc tccagaaggc aaaaccttag ttttttgaaca agaaaatca    60 gatggagttc acactgtaga gactgaagtt ggtgattaca tgttctgctt tgacaataca   120
ttcagcacca tttctgagaa ggtgattttc tttgaattaa tcctggataa tatgggagaa   180
caggcacaag aacaagaaga ttggaagaaa tatattactg gcacagatat attggatatg   240
aaactggaag acatcctggg aatccatcaa cagcatcaag tccagactaa ggcaaaagtg   300
gggcacatac aaactctgct taggagcatt tggaaggctc gtggatccga acattacaa   360 ggaaaggcaa ctttggatta ggagtccaat ttctgggtct atgggttaat ttagtgggtc   420
atggtggtgg tgttcagcct tcagtttata tggctggagg nt                      462

<210> SEQ ID NO 21
<211> LENGTH: 423
<212> TYPE: DNA
<213> ORGANISM: Soares breast 2NbHBst
<220> FEATURE:
<221> NAME/KEY: misc_feature
<222> LOCATION: (10)..(10)
<223> OTHER INFORMATION: n is any nucleotide
```

<221> NAME/KEY: misc_feature
<222> LOCATION: (419)..(419)
<223> OTHER INFORMATION: n is any nucleotide
<300> PUBLICATION INFORMATION:
<308> DATABASE ACCESSION NUMBER: GenBank/R54717
<309> DATABASE ENTRY DATE: 1995-05-22
<313> RELEVANT RESIDUES: (1)..(423)

<400> SEQUENCE: 21

```
gcgcggagan ggacaacagt acctgacgcc tctttcagcc cggatcgcc ccaccaggga      60
atgggcgaca agatctggct gcccttcccc gtgctccttc tggccgctct gcctccggtg    120
ctgctgcctg gggggccggc ttcacacctt ccctcgatag cgacttcacc tttacccttc    180
ccgccggcca gaaggagtgc ttctaccagc ccatgcccct gaaggcctcg ctgggagatc    240
gagtaccaag ttttagatgg agcaggatta gatattgatt ccatcttgc ctctccagaa     300
gggcaaaacc ttagtttttg gaacaaagga aaatcaggtg ggagtttcac antgtaggag    360
gattgaagtt gggtggattt acatgtttct ggttttgac aattacattt caggcaccnt     420
ttt                                                                  423
```

<210> SEQ ID NO 22
<211> LENGTH: 450
<212> TYPE: DNA
<213> ORGANISM: Soares breast 2NbHBst
<220> FEATURE:
<221> NAME/KEY: misc_feature
<222> LOCATION: (11)..(11)
<223> OTHER INFORMATION: n is any nucleotide
<221> NAME/KEY: misc_feature
<222> LOCATION: (419)..(419)
<223> OTHER INFORMATION: n is any nucleotide
<221> NAME/KEY: misc_feature
<222> LOCATION: (431)..(431)
<223> OTHER INFORMATION: n is any nucleotide
<300> PUBLICATION INFORMATION:
<308> DATABASE ACCESSION NUMBER: GenBank/H27167
<309> DATABASE ENTRY DATE: 1995-06-12
<313> RELEVANT RESIDUES: (1)..(450)

<400> SEQUENCE: 22

```
cgcggagacg natcaacagt acctgacgcc tctttcagcc ccggatcgcc ccagcaggat     60
tgggcgacaa gatctggctg cccttccccg tgctccttct ggccgctctg cctccggtgc   120
tgctgcctgg ggggccggct tcacaccttc cctcgatagc gacttcacct ttacccttcc   180
cgccggccag aaggagtgct tctaccagcc catgcccctg aaggcctcgc tgggagatcg   240
agtaccaagt tttagatggg agcaggatta gatattgatt ttccatcttg cctctccaga   300
agggcaaaac cttagttttt tgaacaaagg aaaatcaggt ggggagtttc acaatgtagg   360
aggattgaag tttgggtgat ttacatgttt ttgcttttga acaattacat ttcaggcanc   420
atttttgagg nagggtgaat tttctttgga                                     450
```

<210> SEQ ID NO 23
<211> LENGTH: 402
<212> TYPE: DNA
<213> ORGANISM: Stratagene HeLa cell s3 937216
<300> PUBLICATION INFORMATION:
<308> DATABASE ACCESSION NUMBER: GenBank/AA188741
<309> DATABASE ENTRY DATE: 1997-01-06
<313> RELEVANT RESIDUES: (1)..(402)

<400> SEQUENCE: 23

```
taataactgc attttcctaa ctttgaaaaa ttttgcaaat gtcttaggtg atttaaataa     60
atgagtattg ggcctaattg caacaccagt ctgtttttaa caggttctat tacccagaac   120
```

-continued

```
tttttttgtaa atgcggcagt tacaaattaa ctgtggaagt tttcagtttt aagttataaa    180
tcacctgaga attacctaat gatggattga ataaatcttt agactacaaa agcccaactt    240
ttctctattt acatatgcat ctctcctata atgtaaatag aataatagct ttgaaataca    300
attaggtttt tgagatttt ataaccaaat acatttcagt gtaacatatt agcagaaagc    360
attagtcctt ggactttgct tacattccca aaagctgaca tt                       402
```

<210> SEQ ID NO 24
<211> LENGTH: 309
<212> TYPE: DNA
<213> ORGANISM: Human fetal heart, Lambda ZAP Express
<300> PUBLICATION INFORMATION:
<308> DATABASE ACCESSION NUMBER: GenBank/AA094735
<309> DATABASE ENTRY DATE: 1996-10-25
<313> RELEVANT RESIDUES: (1)..(309)

<400> SEQUENCE: 24

```
ttccatcttg cctctccaga aggcaaaacc ttagtttttg aacaaagaaa atcagatgga     60
gttcacactg tagagactga agttggtgat tacatgttct gctttgacaa tacattcagc    120
accatttctg agaaggtgat tttctttgaa ttaatcctgg ataatatggg agaacaggca    180
caggaacaag aggattggga ggaatatatt actggcacag atatattgga tatgaactgg    240
agacatctgg atcatcacag catcagtcca gactagcaaa gtgggcacat caactctctt    300
aggcatttg                                                            309
```

<210> SEQ ID NO 25
<211> LENGTH: 286
<212> TYPE: DNA
<213> ORGANISM: NCI_CGAP_GCB1
<300> PUBLICATION INFORMATION:
<308> DATABASE ACCESSION NUMBER: GenBank/AA285143
<309> DATABASE ENTRY DATE: 1997-03-17
<313> RELEVANT RESIDUES: (1)..(286)

<400> SEQUENCE: 25

```
agactccaga tttccctgtc aaccacgagg agtccagaga gaaaacgcgg agatgagcaa     60
gcagtacctg acgcctcttt cagcccggga tcgccccagc agggatgggc gacaagatct    120
ggctgccctt ccccgtgctc cttctggccg ctctgcctcc ggtgctgctg cctgggcggc    180
cggcttcaca ccttccctcg atagcgactt cacctttacc cttcccgccg gccagaagga    240
gtgcttctac cagcccatgc gcctgaaagc ctctcttgag atcgag                   286
```

<210> SEQ ID NO 26
<211> LENGTH: 733
<212> TYPE: DNA
<213> ORGANISM: Human IgG FC Region

<400> SEQUENCE: 26

```
gggatccgga gcccaaatct tctgacaaaa ctcacacatg cccaccgtgc ccagcacctg     60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta acagcacg taccgtgtgg tcagcgtcct caccgtcctg caccaggact    300
ggctgaatgg caaggagtac aagtgcaagg tctccaacaa agcccctccca accccatcg    360 agaaaaccat ctccaaagcc aaagggcagc ccgagaacc acaggtgtac accctgcccc    420
```

-continued

```
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```